US012735658B2

(12) United States Patent
Namanja-Magliano et al.

(10) Patent No.: US 12,735,658 B2
(45) Date of Patent: Sep. 15, 2026

(54) CLEANING COMPOSITION COMPRISING AN ENGINEERED FATTY ACID ALPHA-DIOXYGENASE

(71) Applicant: The Procter & Gamble Company, Cincinnati, OH (US)

(72) Inventors: Hilda Namanja-Magliano, Loveland, OH (US); Jean Luc Philippe Bettiol, Etterbeek Brussels (BE); Spencer Christopher Rupard, Birmingham, AL (US); Juan Esteban Velasquez, Jersey City, NJ (US); Denis Alfred Gonzales, Brussels (BE); Emma Louise Barnard, Tyronne (GB); Derek John Quinn, Newtownards (GB); Thomas Shaw Moody, Ballymena (GB); Daniel Fernando Andrade Ribeiro Dourado, Vila do Conde (PT)

(73) Assignee: The Procter & Gamble Company, Cincinnati, OH (US)

( * ) Notice: Subject to any disclaimer, the term of this patent is extended or adjusted under 35 U.S.C. 154(b) by 1120 days.

(21) Appl. No.: 17/847,504

(22) Filed: Jun. 23, 2022

(65) Prior Publication Data

US 2023/0089159 A1 Mar. 23, 2023

Related U.S. Application Data

(60) Provisional application No. 63/244,855, filed on Sep. 16, 2021.

(51) Int. Cl.

| | |
|---|---|
| ***C11D 3/386*** | (2006.01) |
| ***A61K 8/66*** | (2006.01) |
| ***A61Q 5/02*** | (2006.01) |
| ***C11D 1/83*** | (2006.01) |
| ***C12N 9/02*** | (2006.01) |
| ***C12P 7/64*** | (2022.01) |
| *C11D 1/29* | (2006.01) |
| *C11D 1/72* | (2006.01) |
| *C11D 1/75* | (2006.01) |

(52) U.S. Cl.

CPC ............ *C11D 3/38636* (2013.01); *A61K 8/66* (2013.01); *A61Q 5/02* (2013.01); *C11D 1/83* (2013.01); *C12N 9/0069* (2013.01); *C12P 7/64* (2013.01); *C12Y 113/11* (2013.01); *C11D 1/29* (2013.01); *C11D 1/72* (2013.01); *C11D 1/75* (2013.01)

(58) Field of Classification Search

CPC ......... C11D 3/38636; C11D 1/83; C11D 1/29; A61K 8/66; C12N 9/0069

See application file for complete search history.

(56) References Cited

U.S. PATENT DOCUMENTS

| | | | | |
|---|---|---|---|---|
| 5,223,169 | A | 6/1993 | El-sayed | |
| 5,576,282 | A | 11/1996 | Miracle | |
| 5,705,465 | A | 1/1998 | Angevaare et al. | |
| 5,789,362 | A | 8/1998 | Baeck | |
| 5,851,973 | A | 12/1998 | Foley | |
| 6,306,812 | B1 | 10/2001 | Perkins | |
| 6,326,348 | B1 | 12/2001 | Vinson | |
| 6,369,011 | B1 | 4/2002 | Rai | |
| 6,372,708 | B1 | 4/2002 | Kasturi | |
| 6,492,316 | B1 | 12/2002 | Herbots | |
| 6,699,828 | B1 | 3/2004 | De Buzzaccarini | |
| 7,264,954 | B2 | 9/2007 | Sugio | |
| 7,321,025 | B2 | 1/2008 | Feussner | |
| 7,456,001 | B2 | 11/2008 | Christensen | |
| 8,137,477 | B2 | 3/2012 | Wittorff | |
| 8,293,697 | B2 | 10/2012 | Boutique | |
| 8,940,677 | B2 | 1/2015 | Boutique | |
| 9,834,798 | B2 | 12/2017 | Piatesi | |
| 10,526,565 | B2 | 1/2020 | Lant | |
| 10,689,603 | B2 | 6/2020 | Lant | |
| 10,858,616 | B2 | 12/2020 | Lant | |
| 11,072,764 | B2 * | 7/2021 | Bettiol | C11D 1/94 |
| 2003/0162681 | A1 | 8/2003 | Hage | |
| 2003/0166485 | A1 | 9/2003 | Hage | |
| 2003/0191043 | A1 | 10/2003 | Becker | |
| 2005/0203213 | A1 | 9/2005 | Pommiers et al. | |
| 2006/0073994 | A1 | 4/2006 | Hage | |
| 2007/0169741 | A1 | 7/2007 | Vachon | |
| 2007/0173430 | A1 | 7/2007 | Souter et al. | |
| 2009/0142821 | A1 | 6/2009 | Cirino | |
| 2009/0203568 | A1 | 8/2009 | Souter | |

(Continued)

FOREIGN PATENT DOCUMENTS

| | | | |
|---|---|---|---|
| CN | 106753834 | A | 5/2017 |
| EP | 0399681 | A2 | 1/1991 |

(Continued)

OTHER PUBLICATIONS

Ankur Gupta et al.,"Evidence for Protein Radical-Mediated Nuclear Tunneling in Fatty Acid α-Oxygenase", Department of Chemistry, Johns Hopkins University, Department of Biological Chemistry, Yamaguchi University, vol. 130, No. 34, Jun. 4, 2008, pp. 11274-11275.

(Continued)

*Primary Examiner* — Erin M. Bowers

(74) *Attorney, Agent, or Firm* — Kathleen Y. Carter; James E. Oehlenschlager

(57) ABSTRACT

Cleaning compositions having engineered fatty acid alpha-dioxygenases and methods of using said compositions to provide a benefit by converting long chain fatty acids present in soils into 2-hydroperoxy fatty acids or terminal aldehydes.

10 Claims, No Drawings

Specification includes a Sequence Listing.

(56) References Cited

U.S. PATENT DOCUMENTS

| | | | | |
|---|---|---|---|---|
| 2011/0015109 | A1 | 1/2011 | Brooker | |
| 2012/0157717 | A1 | 6/2012 | Rude | |
| 2012/0227120 | A1 | 9/2012 | Hitchman | |
| 2013/0175196 | A1 | 7/2013 | Dale | |
| 2014/0073547 | A1 | 3/2014 | Meek | |
| 2014/0322770 | A1 | 10/2014 | Landvik | |
| 2015/0184208 | A1 | 7/2015 | Oestergaard | |
| 2016/0230195 | A1 | 8/2016 | Osterhout | |
| 2017/0321161 | A1 | 11/2017 | Lant | |
| 2017/0321162 | A1 | 11/2017 | Lant | |
| 2019/0144789 | A1 | 5/2019 | Bettiol | |
| 2019/0144790 | A1 * | 5/2019 | Bettiol | C11D 9/40 510/392 |
| 2019/0144791 | A1 | 5/2019 | Bettiol | |
| 2019/0144794 | A1 | 5/2019 | Velasquez | |
| 2021/0054311 | A1 | 2/2021 | Lant et al. | |
| 2022/0112446 | A1 | 4/2022 | Velasquez et al. | |

FOREIGN PATENT DOCUMENTS

| | | | |
|---|---|---|---|
| EP | 2975107 | A1 | 1/2016 |
| EP | 3243898 | B1 | 2/2019 |
| EP | 3556834 | B1 | 10/2020 |
| GB | 2247025 | A | 2/1992 |
| GB | 2288408 | A | 10/1995 |
| WO | 9526393 | A1 | 10/1995 |
| WO | 9817767 | A1 | 4/1998 |
| WO | 9855634 | A1 | 12/1998 |
| WO | 9903962 | A1 | 1/1999 |
| WO | 9905082 | A1 | 2/1999 |
| WO | 9905084 | A1 | 2/1999 |
| WO | 9905241 | A1 | 2/1999 |
| WO | 9905242 | A1 | 2/1999 |
| WO | 9905243 | A1 | 2/1999 |
| WO | 9905244 | A1 | 2/1999 |
| WO | 9907656 | A2 | 2/1999 |
| WO | 0023548 | A1 | 4/2000 |
| WO | 0023549 | A1 | 4/2000 |
| WO | 0029540 | A1 | 5/2000 |
| WO | 02086114 | A1 | 10/2002 |
| WO | 2006002643 | A2 | 1/2006 |
| WO | 2006090335 | A1 | 8/2006 |
| WO | 2007144857 | A1 | 12/2007 |
| WO | 2008007320 | A2 | 1/2008 |
| WO | 2008014965 | A1 | 2/2008 |
| WO | 2008015443 | A1 | 2/2008 |
| WO | 2008084093 | A2 | 7/2008 |
| WO | 2008087497 | A1 | 7/2008 |
| WO | 2009069077 | A2 | 6/2009 |
| WO | 2009101593 | A2 | 8/2009 |
| WO | 2009154933 | A2 | 12/2009 |
| WO | 2010003934 | A1 | 1/2010 |
| WO | 2010056652 | A1 | 5/2010 |
| WO | 2011072117 | A1 | 6/2011 |
| WO | 2011140316 | A1 | 11/2011 |
| WO | 2012000846 | A1 | 1/2012 |
| WO | 2012019844 | A2 | 2/2012 |
| WO | 2012019849 | A2 | 2/2012 |
| WO | 2012054835 | A1 | 4/2012 |
| WO | 2012166768 | A1 | 12/2012 |
| WO | 2013033318 | A1 | 3/2013 |
| WO | 2013116261 | A2 | 8/2013 |
| WO | 2013171241 | A1 | 11/2013 |
| WO | 2014081700 | A1 | 5/2014 |
| WO | 2014089386 | A1 | 6/2014 |
| WO | 2015074072 | A1 | 5/2015 |
| WO | 2019094531 | A1 | 5/2019 |
| WO | 2019094532 | A1 | 5/2019 |
| WO | 2019094898 | A1 | 5/2019 |

OTHER PUBLICATIONS

Arnab Mukherjee et al.,"Catalytic Mechanism of a Heme and TyrosylRadical-Containing Fatty Acid α-(Di)oxygenase", Department of Chemistry, Johns Hopkins University,vol. 133, No. 2, May 14, 2010, pp. 227-238.

Christopher C. Goulah et al., "The Crystal Structure of α-Dioxygenase Provides Insight into Diversity in the Cyclooxygenase-Peroxidase Superfamily", Hauptman-Woodward Medical Research Institute and Department of Structural Biology, vol. 52, Feb. 1, 2013, pp. 1364-1372.

Gregory S. Huff et al., "Experimental and Computational Investigations of OxygenReactivity in a Heme and Tyrosyl Radical-Containing Fatty Acidα-(Di)oxygenase", Department of Chemistry, Johns Hopkins University, Department of Chemistry and Supercomputing Institute, University of Minnesota, vol. 50, Jul. 26, 2011, pp. 7375-7389.

Guangyu Zhu et al.,"Crystal structures of α-dioxygenase from *Oryza sativa*: Insights into substrate binding and activation by hydrogen peroxide",Hauptman-Woodward Medical Research Institute, Buffalo, New York,Department of Structural Biology, The State University of New York at Buffalo, Buffalo, New York, vol. 22, Aug. 12, 2013, pp. 1432-1438.

Wei Shaohua et al., "Expression, Purification and Activity Identification of *Arabidopsis thaliana* Alpha-dioxygenase 2 (AtDOX2)in Pichia pastoris", College of Life Sciences, Northwest Agriculture and Forestry University, vol. 19, No. 1, Jul. 8, 2010, pp. 51-56.

Wen Liu et al.,"Characterization of the Heme Environment in *Arabidopsis thaliana* Fatty Acid α-Dioxygenase-1*", Department of Biochemistry and Cell Biology, Rice University, Houston, vol. 279, No. 28, Jul. 9, 2004, pp. 1-31.

Belcher, James, et al.—Structure and Biochemical Properties of the Alkene Producing Cytochrome P450 OleT JE (CYP152L1) from the *Jeotgalicoccus* sp. 8456 Bacterium*—The Journal of Biological Chemistry, vol. 289, No. 10, pp. 6535-6550, Mar. 7, 2014.

Bevers, Loes E., et al.—Oleate Hydratase Catalyzes the Hydration of a Nonactivated Carbon-Carbon Bond—Journal of Bacteriology, Aug. 1, 2009, pp. 5010-5012, vol. 191, No. 15.

Davis, S. Christopher, et al.—Oxidation of w-Oxo Fatty Acids by Cytochrome P450 BM-3 (CYP102)—Archives of Biochemistry and Biophysics, vol. 328, No. 1, Apr. 1, 1996, pp. 35-42.

Engleder, Matthias, et al.—Structure-Based Mechanism of Oleate Hydratase from Elizabethkingia Meningoseptica—Chembiochem—A European Journal of Chemical Biology, Aug. 17, 2015, pp. 1730-1734, vol. 16, No. 12.

Girvan, Hazel M., et al.—Applications of Microbial Cytochrome P450 Enzymes in Biotechnology and Synthetic Biology—Current Opinion in Chemical Biology 2016, 31:136-145, www.sciencedirect.com.

Rude, Matthew A., et al.—Terminal Olefin Biosynthesis by a Novel P450 Fatty Acid Decarboxylase from *Jeotgalicoccus* Species—Applied and Environmental Microbiology, Mar. 2011, pp. 1718-1727, vol. 77, No. 5.

Yesiloglu, Yesim, et al.—Lipase-Catalized Esterification of Glycerol and Oleic Acid—Journal of the American Oil Chemists Society, Mar. 1, 2004, pp. 281-284, vol. 81, No. 3.

Branden et al., Introduction to Protein Structure, Garland Publishing Inc., New York, Year 1991, 3 Pages.

Database UniProt [Online] , "SubName: Full=Uncharacterized protein ;", retrieved from EBI accession No. Uniprot:Q0URU2, Database accession No. Q0URU2; Dated Sep. 5, 2006, 2 pages.

Eriel Martinez et. al. "Biochemical Characterization of the Oxygenation of Unsaturated Fatty Acids by the Dioxygenase andHydroperoxide Isomerase of Pseudomonas aeruginosa 42A2", The Journal of Biological Chemistry vol. 285, Issue No. 13, Dated Mar. 26, 2010, pp. 9339-9345.

Estupinan, Monica, et al., "Unveiling the Genes Responsible for the Unique Pseudomonas Aeruginosa Oleate-diol Synthase Activity", Biochimica et Biophysica Acta (BBA) Molecular and Cell Biology of Lipids, vol. 1841, No. 10, Dated Oct. 1, 2014, 12 pages.

Gallagher, S. Protocols in Molecular Biology, Gallagher, S., Current Protocols in Molecular Biology, One-Dimensional SOS Gel Electrophoresis of Proteins, vol. 75, issue 1, Dated Jul. 2006, pp. 10.2.1-10.2A.37.

(56) References Cited

OTHER PUBLICATIONS

Gilbert, Nathaniel, et al., "A Covalent Linker Allows for Membrane Targeting of an Oxylipin Biosynthetic Complex", Biochemistry, vol. 47, No. 40, Dated Oct. 7, 2008, 12 pages.
Gottesman, S., Annual Reviews of Genetics 30, Year 1996, pp. 465-506.
Hamberg, Mats, et al., "Fatty Acid $\alpha$-Dioxygenases", Prostaglandins & other Lipid Mediators, vol. 68-69, Year 2002, pp. 363-374.
Liu et al., "*Arabidopsis thaliana* fatty acid alpha-dioxygenase-1: evaluation of substrates, inhibitors and amino-terminal function", Plant Physiology and Biochemistry, vol. 44, Issues 5-6, Year 2006, pp. 284-293.
Noordermeer, Minke A., et al., "Development of a Biocatalytic Process for the Production of C6-Aldehydes from Vegetable Oils by Soybean Lipoxygenase and Recombinant Hydroperoxide Lyase", Journal of Agricultural and Food Chemistry, vol. 50, No. 15, Dated Jul. 1, 2002, 5 pages.
Raha et al. Journal of Bacteriology 17 4(20), Year 1992, pp. 6644-6652.
Sadowski et al., Current Opinion in Structural Biology 19, Year 2009, pp. 357-362.
Seffemick et al., J. Bacterial. 183(8) , Year 2001, pp. 2405-2410.
Tang et al., Phil Trans R Soc B 368:Mar. 18, 2012, Year 2013, pp. 1-10.
Witkowski et al., Biochemistry 38, Year 1999, pp. 11643-11650.
PCT Search Report and Written Opinion for PCT/US2022/073870 dated Dec. 19, 2022, 22 pages.

* cited by examiner

CLEANING COMPOSITION COMPRISING AN ENGINEERED FATTY ACID ALPHA-DIOXYGENASE

REFERENCE TO A SEQUENCE LISTING

This application contains a Sequence Listing in computer readable form. The computer readable form is incorporated herein by reference.

FIELD OF THE INVENTION

The present invention relates to methods of transforming soil comprising fatty acids and cleaning compositions comprising an engineered fatty acid alpha-dioxygenase enzymes.

BACKGROUND OF THE INVENTION

Cleaning compositions, such as those for cleaning surfaces or garments, should usually have a good soil and/or grease cleaning and/or suds profile especially in the presence of greasy soils. Users usually see cleaning performance and suds profiles as indicators of the quality of the cleaning composition. Moreover, the user of a cleaning composition may also use the suds profile and the appearance of the suds (e.g., density, whiteness) as an indicator that the wash solution still contains active cleaning ingredients. Accordingly, it is desirable for certain cleaning composition to provide "good sudsing profile", which includes good suds height and/or density as well as good suds duration during the initial mixing of the composition with water and/or during the entire washing operation.

It has been found that some types of soil, in particular greasy soils comprising fatty acids, can act as a suds suppressor in the presence of hard water, triggering consumers to replace the product more frequently than is necessary. As such there is a need to provide cleaning compositions with desirable suds properties, especially in the presence of greasy soils, even more in the presence of greasy soils comprising fatty acids, and that at the same time provide good soil and grease removal.

There is also a desire to utilize less surfactant materials in cleaning compositions. However, using less surfactant can decrease the suds generation and/or cleaning performance of the cleaning composition.

There remains a desire to provide cleaning compositions which provide effective suds generation and/or cleaning performance in the presence of soils comprising fatty acids, especially when the cleaning composition contains relatively low amounts of surfactant in the composition.

SUMMARY OF THE INVENTION

The present invention relates to engineered fatty acid alpha-dioxygenase comprising a polypeptide sequence having at least about 70% identity to SEQ ID NO: 1 and its functional fragments thereof; wherein said polypeptide sequence comprises at least one amino acid substitution at position: L53, N54, R57, S72, G74, D117, S121, Q153, V156, H157, D158, M160, D199, G200, T210, W212, D214, S216, E224, R225, K232, K248, E249, E285, E286, T316, L319, L320, K323, M325, A328, M329, N332, T344, L356, H382, E399, A400, F453, S508, K510, K540, F549, F552, I553, S557, or mixtures thereof; wherein said positions are numbered with reference to SEQ ID NO: 1; and wherein said engineered fatty acid alpha-dioxygenase catalyzes the conversion a fatty acid that is at least one of: stearic acid, oleic acid, linoleic acid, linolenic acid, or mixtures thereof.

The present invention further relates to a method of cleaning a surface having disposed thereon a soil comprising one or more fatty acids, the method comprising the steps of: a) contacting said soil disposed on said surface with a cleaning composition comprising an engineered fatty acid alpha-dioxygenase; and b) converting said one or more fatty acid of said soil on said surface into one or more materials selected from the group consisting of 2-hydroperoxy fatty acids, 2-hydroperoxy fatty acid derivatives, and mixtures thereof.

DETAILED DESCRIPTION OF THE INVENTION

Definitions

As used herein, the articles "a" and "an" when used in a claim, are understood to mean one or more of what is claimed or described.

As used herein, the term "substantially free of" or "substantially free from" means that the indicated material is present in an amount of no more than about 5 wt %, preferably no more than about 2%, and more preferably no more than about 1 wt % by weight of the composition.

As used therein, the term "essentially free of" or "essentially free from" means that the indicated material is present in an amount of no more than about 0.1 wt % by weight of the composition, or preferably not present at an analytically detectible level in such composition. It may include compositions in which the indicated material is present only as an impurity of one or more of the materials deliberately added to such compositions.

All percentages and ratios used hereinafter are by weight of total composition, unless otherwise indicated. All percentages, ratios, and levels of ingredients referred to herein are based on the actual amount of the ingredient, and do not include solvents, fillers, or other materials with which the ingredient may be combined as a commercially available product, unless otherwise indicated.

As used herein, the terms "protein," "polypeptide," and "peptide" are used interchangeably herein to denote a polymer of at least two amino acids covalently linked by an amide bond, regardless of length or post-translational modification (e.g., glycosylation, phosphorylation, lipidation, myristoylation, ubiquitination, etc.). Included within this definition are D- and L-amino acids, and mixtures of D- and L-amino acids.

As used herein, "polynucleotide" and "nucleic acid" refer to two or more nucleosides that are covalently linked together. The polynucleotide may be wholly comprised ribonucleosides (i.e., an RNA), wholly comprised of 2' deoxyribonucleosides (i.e., a DNA) or mixtures of ribo- and 2' deoxyribonucleosides. While the nucleosides will typically be linked together via standard phosphodiester linkages, the polynucleotides may include one or more non-standard linkages. The polynucleotide may be single-stranded or double-stranded, or may include both single-stranded regions and double-stranded regions. Moreover, while a polynucleotide will typically be composed of the naturally occurring encoding nucleobases (i.e., adenine, guanine, uracil, thymine, and cytosine), it may include one or more modified and/or synthetic nucleobases (e.g., inosine, xanthine, hypoxanthine, etc.). Such modified or synthetic nucleobases can be encoding nucleobases.

As used herein, "coding sequence" refers to that portion of a nucleic acid (e.g., a gene) that encodes an amino acid sequence of a protein.

As used herein, "naturally occurring," "wild-type," and "WT" refer to the form found in nature. For example, a naturally occurring or wild-type polypeptide or polynucleotide sequence is a sequence present in an organism that can be isolated from a source in nature and which has not been intentionally modified by human manipulation.

As used herein, "non-naturally occurring" or "engineered" or "recombinant" when used in the present invention, refers to a material (e.g., a cell, nucleic acid, or polypeptide), or a material corresponding to the natural or native form of the material, that has been modified in a manner that would not otherwise exist in nature, or is identical or substantially similar thereto but produced or derived from synthetic materials and/or by manipulation using recombinant techniques. Non-limiting examples include, among others, recombinant cells expressing genes that are not found within the native (non-recombinant) form of the cell or express native genes that are otherwise expressed at a different level.

As used herein the term "identity" means the identity between two or more sequences (for example RNA, DNA, or protein sequences) and is expressed in terms of the identity or similarity between the sequences as calculated over the entire length of a sequence aligned against the entire length of the reference sequence. Sequence identity can be measured in terms of percentage identity; the higher the percentage, the more shared sequences there are. The percentage identity is calculated over the length of comparison between the sequences. For example, the identity is typically calculated over the entire length of a sequence aligned against the entire length of the reference sequence. Methods of alignment of sequences for comparison are well known in the art and identity can be calculated by many known methods. Various programs and alignment algorithms are described in the art. It should be noted that the terms 'sequence identity' and 'sequence similarity' can be used interchangeably.

As used herein, "percentage of sequence identity," "percent identity," and "percent identical" refer to comparisons between polynucleotide sequences or polypeptide sequences, and are determined by comparing two optimally aligned sequences over a comparison window, wherein the portion of the polynucleotide or polypeptide sequence in the comparison window may comprise additions or deletions (i.e., gaps) as compared to the reference sequence for optimal alignment of the two sequences. The percentage is calculated by determining the number of positions at which either the identical nucleic acid base or amino acid residue occurs in both sequences or a nucleic acid base or amino acid residue is aligned with a gap to yield the number of matched positions, dividing the number of matched positions by the total number of positions in the window of comparison and multiplying the result by 100 to yield the percentage of sequence identity.

As used herein, the term "variant" of fatty acid alpha-dioxygenase enzyme means a modified fatty acid alpha-dioxygenase enzyme amino acid sequence by or at one or more amino acids (for example 1, 2, 3, 4, 5, 6, 7, 8, 9 or 10 or more amino acid modifications) selected from substitutions, insertions, deletions and combinations thereof. The variant may have "conservative" substitutions, wherein a substituted amino acid has similar structural or chemical properties to the amino acid that replaces it, for example, replacement of leucine with isoleucine. A variant may have "non-conservative" changes, for example, replacement of a glycine with a tryptophan. Variants may also include sequences with amino acid deletions or insertions, or both. Guidance in determining which amino acid residues may be substituted, inserted, or deleted without abolishing the activity of the protein may be found using computer programs well known in the art. Variants may also include truncated forms derived from a wild-type fatty acid alpha-dioxygenase enzyme, such as for example, a protein with a truncated N-terminus. Variants may also include forms derived by adding an extra amino acid sequence to a wild-type protein, such as for example, an N-terminal tag, a C-terminal tag or an insertion in the middle of the protein sequence.

As used herein, "reference sequence" refers to a defined sequence to which another sequence is compared. A reference sequence may be a subset of a larger sequence, for example, a segment of a full-length gene or polypeptide sequence. Generally, a reference sequence is at least about 20 nucleotide or amino acid residues in length, at least about 25 residues in length, at least about 50 residues in length, or the full length of the nucleic acid or polypeptide. Since two polynucleotides or polypeptides may each (1) comprise a sequence (i.e., a portion of the complete sequence) that is similar between the two sequences, and (2) may further comprise a sequence that is divergent between the two sequences, sequence comparisons between two (or more) polynucleotides or polypeptide are typically performed by comparing sequences of the two polynucleotides over a comparison window to identify and compare local regions of sequence similarity. The term "reference sequence" is not intended to be limited to wild-type sequences, and can include engineered or altered sequences. For example, a "reference sequence" can be a previously engineered or altered amino acid sequence.

As used herein, "comparison window" refers to a conceptual segment of at least about 20 contiguous nucleotide positions or amino acids residues wherein a sequence may be compared to a reference sequence of at least about 20 contiguous nucleotides or amino acids and wherein the portion of the sequence in the comparison window may comprise additions or deletions (i.e., gaps) of about 20 percent or less as compared to the reference sequence (which does not comprise additions or deletions) for optimal alignment of the two sequences. The comparison window can be longer than about 20 contiguous residues, and includes, optionally about 30 contiguous residues, 40 contiguous residues, 50 contiguous residues, 100 contiguous residues, or longer contiguous residues windows.

As used herein, "corresponding to", "reference to" or "relative to" when used in the context of the numbering of a given amino acid or polynucleotide sequence refers to the numbering of the residues of a specified reference sequence when the given amino acid or polynucleotide sequence is compared to the reference sequence. In other words, the residue number or residue position of a given polymer is designated with respect to the reference sequence rather than by the actual numerical position of the residue within the given amino acid or polynucleotide sequence. For example, a given amino acid sequence, such as that of an engineered fatty acid alpha-dioxygenase, can be aligned to a reference sequence by introducing gaps to optimize residue matches between the two sequences. In these cases, although the gaps are present, the numbering of the residue in the given amino acid or polynucleotide sequence is made with respect to the reference sequence to which it has been aligned.

As used herein, "increased enzymatic activity" and "increased activity" refer to an improved property of a wild-type or an engineered enzyme, which can be represented by an increase in specific activity (e.g., product produced/time/weight protein) or an increase in percent conversion of the substrate to the product (e.g., percent conversion of starting amount of substrate to product in a specified time period using a specified amount of fatty acid alpha-dioxygenase) as compared to a reference enzyme. Any property relating to enzyme activity may be affected, including the classical enzyme properties of Km, Vmax or kcat, changes of which can lead to increased enzymatic activity. The fatty acid alpha-dioxygenase activity can be measured by any one of standard assays used for measuring fatty acid alpha-dioxygenases, such as change in substrate or product concentration. Comparisons of enzyme activities are made using a defined preparation of enzyme, a defined assay under a set condition, and one or more defined substrates, as further described in detail herein. Generally, when enzymes in cell lysates are compared, the numbers of cells and the amount of protein assayed are determined as well as use of identical expression systems and identical host cells to minimize variations in amount of enzyme produced by the host cells and present in the lysates.

As used herein, "conversion" refers to the enzymatic transformation of a substrate to the corresponding product.

As used herein "percent conversion" refers to the percent of the substrate that is converted to the product within a period of time under specified conditions. Thus, for example, the "enzymatic activity" or "activity" of a fatty acid alpha-dioxygenase polypeptide can be expressed as "percent conversion" of the substrate to the product.

As used herein, "amino acid difference" or "residue difference" refers to a difference in the amino acid residue at a position of a polypeptide sequence relative to the amino acid residue at a corresponding position in a reference sequence. The positions of amino acid differences generally are referred to herein as "Xn", where n refers to the corresponding position in the reference sequence upon which the residue difference is based. For example, a "residue difference at position X53 as compared to SEQ ID NO: 1" refers to a difference of the amino acid residue at the polypeptide position corresponding to position 53 of SEQ ID NO:1. Thus, if the reference polypeptide of SEQ ID NO:1 has a leucine at position 53, then a "residue difference at position X53 as compared to SEQ ID NO:1" refers to an amino acid substitution of any residue other than leucine at the position of the polypeptide corresponding to position 53 of SEQ ID NO:1. In most instances herein, the specific amino acid residue difference at a position is indicated as "XnY" where "Xn" specified the corresponding position as described above, and "Y" is the single letter identifier of the amino acid found in the engineered polypeptide (i.e., the different residue than in the reference polypeptide). In some instances, the present invention also provides specific amino acid differences denoted by the conventional notation "AnB", where A is the single letter identifier of the residue in the reference sequence, "n" is the number of the residue position in the reference sequence, and B is the single letter identifier of the residue substitution in the sequence of the engineered polypeptide. In some instances, a polypeptide of the present invention can include at least one amino acid residue difference relative to a reference sequence, which is indicated by a list of the specified positions where residue differences are present relative to the reference sequence. In embodiments, where more than one amino acid can be used in a specific residue position of a polypeptide, the various amino acid residues that can be used are separated by a "/" (e.g., X53A/F). The present invention includes engineered polypeptide sequences comprising at least one amino acid difference that includes either/or both conservative and non-conservative amino acid substitutions. The amino acid sequences of the specific recombinant fatty acid alpha-dioxygenase polypeptides included in the Sequence Listing of the present invention include an initiating methionine (M) residue (i.e., M represents residue position 1). The skilled artisan, however, understands that this initiating methionine residue can be removed by biological processing machinery, such as in a host cell or in vitro translation system, to generate a mature protein lacking the initiating methionine residue, but otherwise retaining the enzyme's properties. Consequently, the term "amino acid residue difference relative to SEQ ID NO:1 at position Xn" as used herein may refer to position "Xn" or to the corresponding position (e.g., position (X−1)n) in a reference sequence that has been processed so as to lack the starting methionine.

The term "amino acid substitution set" or "substitution set" refers to a group of amino acid substitutions in a polypeptide sequence, as compared to a reference sequence. A substitution set can have 2, 3, 4, 5, 6, 7, 8, 9, 10, 11, 12, 13, 14, 15, or more amino acid substitutions. In embodiments, a substitution set refers to the set of amino acid substitutions that is present in any of the variant fatty acid alpha-dioxygenases.

As used herein, the phrase "conservative amino acid substitutions" refers to the interchangeability of residues having similar side chains, and thus typically involves substitution of the amino acid in the polypeptide with amino acids within the same or similar defined class of amino acids. As such, an amino acid with an aliphatic side chain can be substituted with another aliphatic amino acid (e.g., alanine, valine, leucine, and isoleucine); an amino acid with a hydroxyl side chain can be substituted with another amino acid with a hydroxyl side chain (e.g., serine and threonine); an amino acids having aromatic side chains can be substituted with another amino acid having an aromatic side chain (e.g., phenylalanine, tyrosine, tryptophan, and histidine); an amino acid with a basic side chain can be substituted with another amino acid with a basic side chain (e.g., lysine and arginine); an amino acid with an acidic side chain can be substituted with another amino acid with an acidic side chain (e.g., aspartic acid or glutamic acid); and/or a hydrophobic or hydrophilic amino acid can be replaced with another hydrophobic or hydrophilic amino acid, respectively. The appropriate classification of any amino acid or residue will be apparent to those of skill in the art, especially in light of the detailed invention provided herein.

As used herein, the phrase "non-conservative substitution" refers to substitution of an amino acid in the polypeptide with an amino acid with significantly differing side chain properties. Non-conservative substitutions may use amino acids between, rather than within, the defined groups and affects (a) the structure of the peptide backbone in the area of the substitution (e.g., proline for glycine) (b) the charge or hydrophobicity, or (c) the bulk of the side chain. By way of example and not limitation, an exemplary non-conservative substitution can be an acidic amino acid substituted with a basic or aliphatic amino acid; an aromatic amino acid substituted with a small amino acid; and a hydrophilic amino acid substituted with a hydrophobic amino acid.

As used herein, "deletion" refers to modification of the polypeptide by removal of one or more amino acids from the reference polypeptide. Deletions can comprise removal of 1 or more amino acids, 2 or more amino acids, 5 or more amino acids, 10 or more amino acids, 15 or more amino acids, or 20 or more amino acids, up to 10% of the total number of amino acids, or up to 20% of the total number of amino acids making up the polypeptide while retaining enzymatic activity and/or retaining the improved properties of an engineered enzyme. Deletions can be directed to the internal portions and/or terminal portions of the polypeptide. The deletion can comprise a continuous segment or can be discontinuous.

As used herein, "insertion" refers to modification of the polypeptide by addition of one or more amino acids to the reference polypeptide. In embodiments, the improved engineered fatty acid alpha-dioxygenase enzymes comprise insertions of one or more amino acids to the naturally occurring fatty acid alpha-dioxygenase polypeptide as well as insertions of one or more amino acids to engineered fatty acid alpha-dioxygenase polypeptides. Insertions can be in the internal portions of the polypeptide, or to the carboxy or amino terminus. Insertions as used herein include fusion proteins as is known in the art. The insertion can be a contiguous segment of amino acids or separated by one or more of the amino acids in the naturally occurring polypeptide.

As used herein, "fragment" refers to a polypeptide that has an amino-terminal and/or carboxy-terminal deletion, but where the remaining amino acid sequence is identical to the corresponding positions in the sequence. Fragments can typically have about 80%, about 90%, about 95%, about 98%, or about 99% of the full-length fatty acid alpha-dioxygenase polypeptide, for example, the polypeptide of SEQ ID NO: 1. In embodiments, the fragment is "biologically active" (i.e., it exhibits the same enzymatic activity as the full-length sequence).

A "functional fragment", or a "biologically active fragment", used interchangeably, herein refers to a polypeptide that has an amino-terminal and/or carboxy-terminal deletion(s) and/or internal deletions, but where the remaining amino acid sequence is identical to the corresponding positions in the sequence to which it is being compared and that retains substantially all of the activity of the full-length polypeptide.

As used herein, "isolated polypeptide" refers to a polypeptide which is substantially separated from other contaminants that naturally accompany it (e.g., protein, lipids, and polynucleotides). The term embraces polypeptides which have been removed or purified from their naturally occurring environment or expression system (e.g., host cell or in vitro synthesis). The improved fatty acid alpha-dioxygenase enzymes may be present within a cell, present in the cellular medium, or prepared in various forms, such as lysates or isolated preparations. As such, in embodiments, the wild-type or engineered fatty acid alpha-dioxygenase polypeptides of the present invention can be an isolated polypeptide.

As used herein, "substantially pure polypeptide" refers to a composition in which the polypeptide species is the predominant species present (i.e., on a molar or weight basis it is more abundant than any other individual macromolecular species in the composition), and is generally a substantially purified composition when the object species comprises at least about 50 percent of the macromolecular species present by mole or % weight. Generally, a substantially pure wild-type or engineered fatty acid alpha-dioxygenase polypeptide composition will comprise about 60% or more, about 70% or more, about 80% or more, about 90% or more, about 91% or more, about 92% or more, about 93% or more, about 94% or more, about 95% or more, about 96% or more, about 97% or more, about 98% or more, or about 99% of all macromolecular species by mole or % weight present in the composition. Solvent species, small molecules (<500 Daltons), and elemental ion species are not considered macromolecular species. In embodiments, the isolated improved fatty acid alpha-dioxygenase polypeptide is a substantially pure polypeptide composition.

As used herein, when used with reference to a nucleic acid or polypeptide, the term "heterologous" refers to a sequence that is not normally expressed and secreted by an organism (e.g., a wild-type organism). The term can encompass a sequence that comprises two or more subsequences which are not found in the same relationship to each other as normally found in nature, or is recombinantly engineered so that its level of expression, or physical relationship to other nucleic acids or other molecules in a cell, or structure, is not normally found in nature. For instance, a heterologous nucleic acid is typically recombinantly produced, having two or more sequences from unrelated genes arranged in a manner not found in nature (e.g., a nucleic acid open reading frame (ORF) of the invention operatively linked to a promoter sequence inserted into an expression cassette, such as a vector). "Heterologous polynucleotide" can refer to any polynucleotide that is introduced into a host cell by laboratory techniques, and includes polynucleotides that are removed from a host cell, subjected to laboratory manipulation, and then reintroduced into a host cell.

As used herein, "codon optimized" refers to changes in the codons of the polynucleotide encoding a protein to those preferentially used in a particular organism such that the encoded protein is efficiently expressed in the organism of interest. In embodiments, the polynucleotides encoding the fatty acid alpha-dioxygenase enzymes may be codon optimized for optimal production from the host organism selected for expression.

As used herein, "suitable reaction conditions" refer to those conditions in the biocatalytic reaction solution (e.g., ranges of enzyme loading, substrate loading, temperature, pH, buffers, co-solvents, etc.) under which a fatty acid alpha-dioxygenase polypeptide of the present invention is capable of converting a substrate compound to a product compound (e.g., conversion of one compound to another compound).

As used herein, "substrate" in the context of a biocatalyst mediated process refers to the compound or molecule acted on by the biocatalyst.

As used herein "product" in the context of a biocatalyst mediated process refers to the compound or molecule resulting from the action of the biocatalyst.

By "cleaning composition", as used herein, it is meant compositions for treating hair (human, dog, and/or cat), including bleaching, coloring, dyeing, conditioning, growing, removing, retarding growth, shampooing, and styling; personal cleansing; color cosmetics; products relating to treating skin (human, dog, and/or cat), including creams, lotions, ointments, and other topically applied products for consumer use; products relating to orally administered materials for enhancing the appearance of hair, skin, and/or nails (human, dog, and/or cat); shaving; body sprays; fine fragrances such as colognes and perfumes; compositions for treating fabrics, hard surfaces and any other surfaces in the area of fabric and home care, including air care, car care, dishwashing, fabric conditioning (including softening), fabric freshening, laundry detergents, laundry and rinse additive and/or care, hard surface cleaning and/or treatment, and other cleaning for consumer or institutional use; products relating to disposable absorbent and/or non-absorbent articles including adult incontinence garments, bibs, diapers, training pants, infant and toddler care wipes; hand soaps; products relating to oral care compositions including toothpastes, tooth gels, mouth rinses, denture adhesives, and tooth whitening; personal health care medications; products relating to grooming including shave care compositions and composition for coating, or incorporation into, razors or other shaving devices; and compositions for coating, or incorporation into, wet or dry bath tissue, facial tissue, disposable handkerchiefs, disposable towels and/or wipes, incontinence pads, panty liners, sanitary napkins, and tampons and tampon applicators; and combinations thereof; preferably a detergent composition.

As used herein, the term "detergent composition" refers to a composition or formulation designed for cleaning soiled surfaces. Such compositions include but are not limited to, dishwashing compositions, laundry detergent compositions, fabric softening compositions, fabric enhancing compositions, fabric freshening compositions, laundry pre-wash, laundry pretreat, laundry additives, spray products, dry cleaning agent or composition, laundry rinse additive, wash additive, post-rinse fabric treatment, ironing aid, hard surface cleaning compositions, unit dose formulation, delayed delivery formulation, detergent contained on or in a porous substrate or nonwoven sheet, and other suitable forms that may be apparent to one skilled in the art in view of the teachings herein. Such compositions may be used as a pre-cleaning treatment, a post-cleaning treatment, or may be added during the rinse or wash cycle of the cleaning process. The detergent compositions may have a form selected from liquid, powder, single-phase or multi-phase unit dose or pouch form, tablet, gel, paste, bar, fiber, foam, or flake. Preferably the composition is for manual-washing. Preferably, the detergent composition of the present invention is a dishwashing detergent. Preferably the composition is in the form of a liquid.

As used herein the term "improved suds longevity" means an increase in the duration of visible suds in a washing process cleaning soiled articles using the composition comprising enzymes of use in the compositions of the present invention, compared with the suds longevity provided by the same composition and process in the absence of the enzyme.

As used herein, the term "soiled surfaces" refers non-specifically to any type of flexible material consisting of a network of natural or artificial fibers, including natural, artificial, and synthetic fibers, such as, but not limited to, cotton, linen, wool, polyester, nylon, silk, acrylic, and the like, as well as various blends and combinations. Soiled surfaces may further refer to any type of hard surface, including natural, artificial, or synthetic surfaces, such as, but not limited to, tile, ceramic, granite, grout, glass, composite, vinyl, hardwood, metal, cooking surfaces, plastic, and the like, as well as blends and combinations, as well as dishware. Key targeted soiled surfaces by this application are soiled dishware.

As used herein, the term "water hardness" or "hardness" means uncomplexed cation ions (i.e., $Ca^{2+}$ or $Mg^{2+}$) present in water that have the potential to precipitate with anionic surfactants or any other anionically charged detergent actives under alkaline conditions, and thereby diminishing the surfactancy and cleaning capacity of surfactants. Further, the terms "high water hardness" and "elevated water hardness" can be used interchangeably and are relative terms for the purposes of the present invention, and are intended to include, but not limited to, a hardness level containing at least 12 grams of calcium ion per gallon water (gpg, "American grain hardness" units).

Engineered Fatty Acid Alpha-Dioxygenases

Fatty acids can be oxidized in the presence of molecular oxygen ($O_2$) by fatty acid alpha-dioxygenases (αDOX), which convert saturated and unsaturated fatty acids to their corresponding 2-hydroperoxy fatty acids via stereoselective oxygenation at the alpha carbon. The resulting 2-hydroperoxy fatty acids can undergo spontaneous decarboxylation to shorter aldehydes or can be reduced to 2-hydroxy fatty acids in the presence of a reducing agent. αDOX are generally encoded by different species of plants and fungi, where they are up-regulated during the host defense response against pathogen attack, but homologs are also found in bacteria. Alpha-dioxygenases are grouped under the InterPRO family IPR034815 and members of such family are included as part of the current invention.

Crystal structures of *Oryza sativa* αDOX (SEQ ID NO: 1; PDB ID: 4KVJ, 4KVK, and 4KVL) have been published, revealing the substrate binding site and the active site residues. These structures, together with sequence alignments, suggest that several amino acids may contribute to and/or define the active site of the enzyme. For instance, in SEQ ID NO: 1, the residues H311, Y379, H382 and R559, which are highly conserved in the family, are important for catalysis. Residues N145, (H/R)157, W213, D214, S216, Y219, G220, R230, G256, G264, H276, N277, A308, K309, H311, W315, F375, Y379, R380, H382, S435, G437, N448, Y520, G532, F549, F552, R559, and G579 are also highly conserved, but their roles in catalysis have not been well established.

In embodiments of the present invention, the engineered fatty acid alpha-dioxygenase comprises a polypeptide sequence comprising the amino acids H311, Y379, H382 and R559, wherein said positions are numbered with reference to SEQ ID NO: 1. In embodiments of the present invention, the engineered fatty acid alpha-dioxygenase comprises a polypeptide sequence comprising the amino acids N145, (H/R)157, W213, D214, S216, Y219, G220, R230, G256, G264, H276, N277, A308, K309, H311, W315, F375, Y379, R380, H382, S435, G437, N448, Y520, G532, F549, F552, R559, and G579, wherein said positions are numbered with reference to SEQ ID NO: 1.

In embodiments, the engineered fatty acid alpha-dioxygenase comprises a polypeptide sequence comprising one or more sequence motifs selected from the group consisting of: FGRN, N-$(X)_2$-T-X-WWD-X-S, WD-X-S-$(X)_2$-YG, F-$(X)_2$-EHN-$(X)_2$-CD, ANW-X-G, AK-X-H, YR-X-H, PYS-X-TE-X-F-$(X)_2$-VYR-X-H-X-L, R-X-RER-X-V-X-RYN-X-FRR, MA-X-RRL-$(X)_2$-DRF, and combinations thereof; wherein X represents any amino acid. In embodiments, the engineered fatty acid alpha-dioxygenase comprises a polypeptide sequence comprising the sequence motifs: FGRN, N-$(X)_2$-T-X-WWD-X-S, WD-X-S-$(X)_2$-YG, F-$(X)_2$-EHN-$(X)_2$-CD, ANW-X-G, AK-X-H, YR-X-H, PYS-X-TE-X-F-$(X)_2$-VYR-X-H-X-L, R-X-RER-X-V-X-RYN-X-FRR, and MA-X-RRL-$(X)_2$-DRF; wherein X represents any amino acid.

Not wishing to be bound by theory, in several alpha-dioxygenases, the pro-R hydrogen covalently bound to carbon two of a fatty acid is removed utilizing a tyrosyl radical, followed by addition of molecular oxygen to generate a 2-hydroperoxy fatty acid. In *Oryza sativa* αDOX (SEQ ID NO 1), such tyrosyl radical is generated from Tyr379. Alternatively, a cysteine thiyl radical could catalyze such reaction. In embodiments of the present invention, the engineered fatty acid alpha-dioxygenase comprises a polypeptide sequence comprising a tyrosine or a cysteine at position 379, wherein said position is numbered with reference to SEQ ID NO: 1.

In embodiments of the present invention, the cleaning composition comprises engineered fatty acid alpha-dioxygenases. Preferred engineered fatty acid alpha-dioxygenases exhibit at least 20%, preferably at least 30%, preferably at least 40%, preferably at least 50%, preferably at least 60%, preferably at least 70%, preferably at least 80%, preferably at least 90%, preferably at least 95%, preferably at least 98% or preferably even 100% identity as calculated over the entire length of a sequence aligned against the entire length of SED ID NO: 1, and its functional fragments thereof.

Identity, or homology, percentages as mentioned herein in respect of the present invention are those that can be calculated, for example, with AlignX obtainable from Thermo Fischer Scientific or with the alignment tool from Uniprot (https://www.uniprot.org/align/). Alternatively, a manual alignment can be performed. For enzyme sequence comparison the following settings can be used: Alignment algorithm: Needleman and Wunsch, J. Mol. Biol. 1970, 48: 443-453. As a comparison matrix for amino acid similarity the Blosum62 matrix is used (Henikoff S. and Henikoff J. G., P.N.A.S. USA 1992, 89: 10915-10919). The following gap scoring parameters are used: Gap opening penalty: −10, gap extension penalty: −1.

Preferably the engineered fatty acid alpha-dioxygenases are present in an amount of from 0.0001 wt % to 1 wt %, by weight of the composition, based on active protein in the composition. More preferably the engineered fatty acid alpha-dioxygenases are present in the amounts of from 0.001 wt % to 0.2 wt %, by weight of the composition, based on active protein in the composition.

In embodiments of the present invention, the fatty acids being converted by the engineered fatty acid alpha-dioxygenases are selected from the group consisting of: mono unsaturated fatty acids, di unsaturated fatty acids, tri unsaturated fatty acids, tetra unsaturated fatty acids, penta unsaturated fatty acids, hexa unsaturated fatty acids, saturated fatty acids, and mixtures thereof; preferably myristoleic acid, myristic acid, pentadecanoic acid, palmitoleic acid, palmitic acid, sapienic acid, margaric acid, oleic acid, elaidic acid, vaccenic acid, linoleic acid, linoelaidic acid, α-linolenic acid, γ-linolenic acid, stearic acid, gadoleic acid, arachidic acid, behenic acid, α-eleostearic acid, β-eleostearic acid, ricinoleic acid, eicosenic acid, arachidonic acid, eicosapentaenoic acid, erucic acid, docosadienoic acid, docosahexaenoic acid, tetracosenoic acid, and mixtures thereof, preferably palmitic acid, stearic acid, oleic acid, and linoleic acid, and mixtures thereof.

The present invention includes engineered fatty acid alpha-dioxygenases, as previously described. Engineered fatty acid alpha-dioxygenases include polypeptide sequences resulting from modification of a wild-type fatty acid alpha-dioxygenase at one or more amino acids. An engineered fatty acid alpha-dioxygenase includes a "modified enzyme" or a "mutant enzyme" which encompasses proteins having at least one substitution, insertion, and/or deletion of an amino acid. A modified enzyme may have 1, 2, 3, 4, 5, 6, 7, 8, 9 or 10 or more amino acid modifications (selected from substitutions, insertions, deletions and combinations thereof).

In embodiments of the present invention, the engineered fatty acid alpha-dioxygenase comprises a polypeptide sequence having at least about 70% identity to SEQ ID NO: 1 and its functional fragments thereof; wherein said polypeptide sequence comprises at least one amino acid substitution at positions selected from the group consisting of: L53, N54, R57, S72, G74, D117, S121, Q153, V156, H157, D158, M160, D199, G200, T210, W212, D214, S216, E224, R225, K232, K248, E249, E285, E286, T316, L319, L320, K323, M325, A328, M329, N332, T344, L356, H382, E399, A400, F453, S508, K510, K540, F549, F552, I553, S557, and mixtures thereof; wherein said positions are numbered with reference to SEQ ID NO: 1; and wherein said engineered fatty acid alpha-dioxygenase catalyzes the conversion of at least one fatty acid selected from the group consisting of: stearic acid, oleic acid, linoleic acid, linolenic acid, and mixtures thereof.

In embodiments, the engineered fatty acid alpha-dioxygenase comprises a polypeptide sequence comprising at least one amino acid substitution selected from the group consisting of: L53A, L53F, L53I, L53M, N54A, N54G, N54I, N54L, N54V, R57A, R57H, R57I, R57M, R57V, S72P, G74P, G74R, G74S, G74Y, D117A, D117E, D117K, D117P, S121K, Q153H, Q153N, V156I, V156L, V156N, V156T, H157G, H157K, H157P, H157R, H157Y, D158A, D158E, D158G, D158N, D158V, M160F, M160I, M160L, M160T, M160V, D199E, D199F, D199P, D199Y, G200A, G200D, G200N, G200P, G200Q, G200S, T210A, T210S, T210V, W212A, W212Q, W212R, D214A, D214E, D214N, D214V, S216A, S216G, S216T, E224D, E224N, R225T, R225V, K232D, E242A, K248A, K248D, K248L, K248N, K248S, K248T, K248V, E249K, E249P, E249S, E285K, E285R, E286A, E286D, E286K, T316S, L319F, L319I, L319M, L319V, L319W, L320F, L320I, L320M, K323D, M325I, M325L, M325V, A328G, A328I, A328V, M329A, M329I, M329L, N332A, N332I, N332L, N332V, T344A, T344I, T344L, T344N, T344S, T344V, L356F, L356I, H382T, E399G, A400N, A400P, A400Q, A400S, F453L, F453M, S508D, S508E, S508N, S508P, K510E, K510P, K540P, F549A, F549I, F549M, F552A, F552I, F552M, I553L, S557A, S557T, S557V, and mixtures thereof; preferably N54V (SEQ ID NO: 4), S72P (SEQ ID NO: 5), G74P (SEQ ID NO: 6), D117K (SEQ ID NO: 7), V156I (SEQ ID NO: 8), M160I (SEQ ID NO: 9), M160T (SEQ ID NO: 10), G200D (SEQ ID NO: 11), R225V (SEQ ID NO: 12), K248S (SEQ ID NO: 13), K248T (SEQ ID NO: 14), M329L (SEQ ID NO: 15), T344N (SEQ ID NO: 16), T344S (SEQ ID NO: 17), D399G (SEQ ID NO: 18), A400P (SEQ ID NO: 19), and S508D (SEQ ID NO: 20), and mixtures thereof; more preferably G74P, G200D, K248T, T344N, and mixtures thereof; wherein said positions are numbered with reference to SEQ ID NO: 1.

In embodiments of the present invention, the engineered fatty acid alpha-dioxygenase comprises a polypeptide sequence comprising at least the amino acid substitutions selected from the group consisting of: N54G/A328G, N54G/F552A, N54G/A328G/L356F, M325L/I553L/N54G/A328G, M325L/I553L/N54G/A328G/K323D, M325L/I553L/N54G/A328G/L356F/K323D, N54G/A328G, S557V/N332V, N54G/A328G, S557V/N332V, S557A/N332A, N332V/R57A, N332V/S557A, N332V/S557A/L320M, N332V/S557A/L319M, N332V/S557A/L356I, N332V/S557A/R57A, N332V/S557V/L319M, N332V/S557V/R57A, V156I/M160T, V156I/M160F, V156T/M160F, V156I/M160I, H157K/F453M, H157R/F453L, Q153H/H157P, Q153N/H157K, D199P/G200P, S72P/G74P, E399G/A400P, G74P/G200N/T344V, K248D/E249K, G74P/E399G/A400P, E285K/E399G/A400P, G74P/E285K/T344V, D158N/T210S/S216G, T210S/S216A, D158N/S216T, T210S/W212R, D158G/T210S, T210A/S216A, D158A/T210S, T210A/W212A, D158A/D214A, D158A/T210S, and mixtures thereof; preferably S72P/G74P (SEQ ID NO: 21), V156I/M160T (SEQ ID NO: 22), and G74P/D399G/A400P (SEQ ID NO: 23); wherein said positions are numbered with reference to SEQ ID NO: 1.

In embodiments of the present invention, the engineered fatty acid alpha-dioxygenase comprises a polypeptide sequence comprising at least the amino acid substitutions selected from the group consisting of: V156I/M160S, M329L/K248D, M329L/G200D, M329L/G200E, M329L/G74P, M329L/K248T, M329L/R225I, V156I/M160T/K508D, M329L/G200D/K508D, M329L/G74P/K508D, M329L/S72P/G74P/K508D, V156I/M160T/M329L/G74P/G200D, V156I/M160T/M329L/G200D/K508D, V156I/M160T/M329L/S72P/G74P/G200D/K508D, V156I/M160T/M329L/G74P/G200D/K508D, V156I/M160T/M329L/S72P/G74P/D399G/A400P, S72P/G74P/D399G/A400P/G200D/K508D, V156I/M160T/M329L/G74P/D399G/A400P/G200D/K508D, V156I/M160T/G200D/S72P/G74P, V156I/M160T/G74P/G200D, V156I/M160T/S72P/G74P/D399G/A400P, V156I/M160T/G74P/G200D/K508D, V156I/M160T/K248D/G200D, V156I/M160T/K248T/R225V, V156I/M160T/G74P/G200D/K508D, V156I/M160T/G74P/G200D/R225V, V156I/M160T/G74P/G200D/K248T/K508D, V156I/M160T/S72P/G74P/D399G/A400P/K248T/K508D, V156I/M160T/S72P/G74P/G200D/K248T/K508D, V156I/M160T/G74P/D399G/A400P, M329L/G74P/G200D/K508D, V156I/M160T/G200D, V156I/M160T/K508D, M329L/G74P/D399G/A400P, and M329L/S72P/G74P/D399G/A400P; wherein said positions are numbered with reference to SEQ ID NO: 1.

The engineered fatty acid alpha-dioxygenases may have "conservative" substitutions, replacement of an amino acid by another that has similar biochemical properties. Suitable examples of conservative substitution include one conservative substitution in the enzyme, such as a conservative substitution in SEQ ID NO: 1 and its functional fragments thereof. Other suitable examples include 10 or fewer conservative substitutions in the protein, such as five or fewer. An enzyme of the invention may therefore include 1, 2, 3, 4, 5, 6, 7, 8, 9, 10 or more conservative substitutions. An enzyme can be produced to contain one or more conservative substitutions by manipulating the nucleotide sequence that encodes that enzyme using, for example, standard procedures such as site-directed mutagenesis or PCR. Examples of amino acids which may be substituted for an original amino acid in an enzyme and which are regarded as conservative substitutions include: Ser for Ala; Lys for Arg; Gln or His for Asn; Glu for Asp; Asn for Gln; Asp for Glu; Pro for Gly; Asn or Gln for His; Leu or Val for Ile; Ile or Val for Leu; Arg or Gln for Lys; Leu or Ile for Met; Met, Leu or Tyr for Phe; Thr for Ser; Ser for Thr; Tyr for Trp; Trp or Phe for Tyr; and Ile or Leu for Val.

It is important that engineered enzymes retain and preferably improve the ability of the wild-type protein to catalyze the conversion of the fatty acids. Some performance drop in a given property of the engineered enzymes may of course be tolerated, but the engineered enzymes should retain and preferably improve suitable properties for the relevant application for which they are intended. Screening of engineered enzymes of one of the wild-types can be used to identify whether they retain and preferably improve appropriate properties.

The engineered fatty acid alpha-dioxygenase polypeptides described herein are not restricted to the genetically encoded amino acids. Thus, in addition to the genetically encoded amino acids, the polypeptides described herein may be comprised, either in whole or in part, of naturally-occurring and/or synthetic non-encoded amino acids. Certain commonly encountered non-encoded amino acids of which the polypeptides described herein may be comprised include, but are not limited to: the D-stereoisomers of the genetically-encoded amino acids; 2,3-diaminopropionic acid (Dpr); α-aminoisobutyric acid (Aib); ε-aminohexanoic acid (Aha); δ-aminovaleric acid (Ava); N-methylglycine or sarcosine (MeGly or Sar); ornithine (Orn); citrulline (Cit); t-butylalanine (Bua); t-butylglycine (Bug); N-methylisoleucine (MeIle); phenylglycine (Phg); cyclohexylalanine (Cha); norleucine (Nle); naphthylalanine (Nal); 2-chlorophenylalanine (Oct); 3-chlorophenylalanine (Mcf); 4-chlorophenylalanine (Pcf); 2-fluorophenylalanine (Off); 3-fluorophenylalanine (Mff); 4-fluorophenylalanine (Pff); 2-bromophenylalanine (Obf); 3-bromophenylalanine (Mbf); 4-bromophenylalanine (Pbf); 2-methylphenylalanine (Omf); 3-methylphenylalanine (Mmf); 4-methylphenylalanine (Pmf); 2-nitrophenylalanine (Onf); 3-nitrophenylalanine (Mnf); 4-nitrophenylalanine (Pnf); 2-cyanophenylalanine (Ocf); 3-cyanophenylalanine (Mcf); 4-cyanophenylalanine (Pcf); 2-trifluoromethylphenylalanine (Otf); 3-trifluoromethylphenylalanine (Mtf); 4-trifluoromethylphenylalanine (Ptf); 4-aminophenylalanine (Paf); 4-iodophenylalanine (Pif); 4-aminomethylphenylalanine (Pamf); 2,4-dichlorophenylalanine (Opcf); 3,4-dichlorophenylalanine (Mpcf); 2,4-difluorophenylalanine (Opff); 3,4-difluorophenylalanine (Mpff); pyrid-2-ylalanine (2pAla); pyrid-3-ylalanine (3pAla); pyrid-4-ylalanine (4pAla); naphth-1-ylalanine (1nAla); naphth-2-ylalanine (2nAla); thiazolylalanine (taAla); benzothienylalanine (bAla); thienylalanine (tAla); furylalanine (fAla); homophenylalanine (hPhe); homotyrosine (hTyr); homotryptophan (hTrp); pentafluorophenylalanine (5ff); styrylkalanine (sAla); authrylalanine (aAla); 3,3-diphenylalanine (Dfa); 3-amino-5-phenylpentanoic acid (Afp); penicillamine (Pen); 1,2,3,4-tetrahydroisoquinoline-3-carboxylic acid (Tic); β-2-thienylalanine (Thi); methionine sulfoxide (Mso); N(w)-nitroarginine (nArg); homolysine (hLys); phosphonomethylphenylalanine (pmPhe); phosphoserine (pSer); phosphothreonine (pThr); homoaspartic acid (hAsp); homoglutamic acid (hGlu); 1-aminocyclopent-(2 or 3)-ene-4 carboxylic acid; pipecolic acid (PA), azetidine-3-carboxylic acid (ACA); 1-aminocyclopentane-3-carboxylic acid; allylglycine (aOly); propargylglycine (pgGly); homoalanine (hAla); norvaline (nVal); homoleucine (hLeu), homovaline (hVal); homoisoleucine (hIle); homoarginine (hArg); N-acetyl lysine (AcLys); 2,4-diaminobutyric acid (Dbu); 2,3-diaminobutyric acid (Dab); N-methylvaline (MeVal); homocysteine (hCys); homoserine (hSer); hydroxyproline (Hyp) and homoproline (hPro). Additional non-encoded amino acids of which the polypeptides described herein may be comprised will be apparent to those of skill in the art. These amino acids may be in either the L- or D-configuration.

The invention also includes engineered enzymes in the form of truncated forms or fragments derived from a wild-type enzyme, such as a protein with a truncated N-terminus or a truncated C-terminus. In embodiments, the present invention also provides engineered fatty acid alpha-dioxygenases that comprise a fragment of any of the alpha-dioxygenase polypeptides described herein that retain the functional alpha-dioxygenase activity and/or an improved property of an engineered fatty acid alpha-dioxygenase polypeptide. Accordingly, in embodiments, the present invention provides a polypeptide fragment having alpha-dioxygenase activity (e.g., capable of converting substrate to product under suitable reaction conditions), wherein the fragment comprises at least about 80%, 90%, 95%, 98%, or 99% of a full-length amino acid sequence of an engineered polypeptide of the present invention. Some enzymes may include an N-terminal signal peptide that is likely removed upon secretion by the cell. The present invention includes variants without the N-terminal signal peptide. Bioinformatic tools, such as SignalP ver 4.1 (Petersen T N., Brunak S., von Heijne G. and Nielsen H. (2011), Nature Methods, 8:785-786), can be used to predict the existence and length of such signal peptides.

In embodiments, the present invention provides an engineered fatty acid alpha-dioxygenase having an amino acid sequence comprising an insertion as compared to any one of the alpha-dioxygenase polypeptide sequences described herein. Thus, for each and every embodiment of the alpha-dioxygenase polypeptides of the invention, the insertions can comprise one or more amino acids, 2 or more amino acids, 3 or more amino acids, 4 or more amino acids, 5 or more amino acids, 6 or more amino acids, 8 or more amino acids, 10 or more amino acids, 15 or more amino acids, or 20 or more amino acids, where the associated functional activity and/or improved properties of the alpha-dioxygenase described herein is maintained. The insertions can be to the amino or carboxy terminus, or internal portions of the alpha-dioxygenase polypeptide. The invention also includes variants derived by adding an extra amino acid sequence, such as an N-terminal tag or a C-terminal tag. Non-limiting examples of tags are maltose binding protein (MBP) tag, glutathione S-transferase (GST) tag, thioredoxin (Trx) tag, His-tag, and any other tags known by those skilled in art. Tags can be used to improve solubility and expression levels during fermentation or as a handle for enzyme purification.

Enzymes can also be modified by a variety of chemical techniques to produce derivatives having essentially the same or preferably improved activity as the unmodified enzymes, and optionally having other desirable properties. For example, carboxylic acid groups of the protein, whether carboxyl-terminal or side chain, may be provided in the form of a salt of a pharmaceutically-acceptable cation or esterified, for example to form a C1-C6 alkyl ester, or converted to an amide, for example of formula CONR1R2 wherein R1 and R2 are each independently H or C1-C6 alkyl, or combined to form a heterocyclic ring, such as a 5- or 6-membered ring. Amino groups of the enzyme, whether amino-terminal or side chain, may be in the form of a pharmaceutically-acceptable acid addition salt, such as the HCl, HBr, acetic acid, benzoic acid, toluene sulfonic acid, maleic acid, tartaric acid and other organic acid addition salts, or may be modified to C1-C20 alkyl or dialkyl amino or further converted to an amide. Hydroxyl groups of the protein side chains may be converted to alkoxy or ester groups, for example C1-C20 alkoxy or C1-C20 alkyl ester, using well-recognized techniques. Phenyl and phenolic rings of the protein side chains may be substituted with one or more halogen atoms, such as F, Cl, Br or I, or with C1-C20 alkyl, C1-C20 alkoxy, carboxylic acids and esters thereof, or amides of such carboxylic acids. Methylene groups of the protein side chains can be extended to homologous C2-C4 alkylenes. Thiols can be protected with any one of a number of well-recognized protecting groups, such as acetamide groups. Those skilled in the art will also recognize methods for introducing cyclic structures into the proteins of this disclosure to select and provide conformational constraints to the structure that result in enhanced stability.

In embodiments, the enzymes can be provided on a solid support, such as a membrane, resin, solid carrier, or other solid phase material. A solid support can be composed of organic polymers such as polystyrene, polyethylene, polypropylene, polyfluoroethylene, polyethyleneoxy, and polyacrylamide, as well as co-polymers and grafts thereof. A solid support can also be inorganic, such as glass, silica, controlled pore glass (CPG), reverse phase silica or metal, such as gold or platinum. The configuration of a solid support can be in the form of beads, spheres, particles, granules, a gel, a membrane or a surface. Surfaces can be planar, substantially planar, or non-planar. Solid supports can be porous or non-porous, and can have swelling or non-swelling characteristics. A solid support can be configured in the form of a well, depression, or other container, vessel, feature, or location.

In embodiments, the polypeptides having alpha-dioxygenase activity are bound or immobilized on the solid support such that they retain at least a portion of their improved properties relative to a reference polypeptide (e.g., SEQ ID NO: 1). Accordingly, it is further contemplated that any of the methods of using the alpha-dioxygenase polypeptides of the present invention can be carried out using the same alpha-dioxygenase polypeptides bound or immobilized on a solid support.

The alpha-dioxygenase polypeptide can be bound non-covalently or covalently. Various methods for conjugation and immobilization of enzymes to solid supports (e.g., resins, membranes, beads, glass, etc.) are well known in the art. Other methods for conjugation and immobilization of enzymes to solid supports (e.g., resins, membranes, beads, glass, etc.) are well known in the art (See, e.g., Yi et al., Proc. Biochem., 42: 895-898 [2007]; Martin et al., Appl. Microbiol. Biotechnol., 76: 843-851 [2007]; Koszelewski et al. J. Mol. Cat. B: Enz., 63: 39-44 [2010]; Truppo et al., Org. Proc. Res. Develop., published online: dx.doi.org/10.1021/op200157c; and Mateo et al., Biotechnol. Prog., 18:629-34 [2002], etc.). Solid supports useful for immobilizing the alpha-dioxygenase polypeptides of the present invention include, but are not limited to, beads or resins comprising polymethacrylate with epoxide functional groups, polymethacrylate with amino epoxide functional groups, styrene/DVB copolymer or polymethacrylate with octadecyl functional groups.

The enzymes may be incorporated into the cleaning compositions via an additive particle, such as an enzyme granule or in the form of an encapsulate or may be added in the form of a liquid formulation. Encapsulating the enzymes promote the stability of the enzymes in the composition and helps to counteract the effect of any hostile compounds present in the composition, such as bleach, protease, surfactant, chelant, etc. The engineered fatty acid alpha-dioxygenases may be the only enzymes in the additive particle or may be present in the additive particle in combination with one or more additional co-enzymes.

In embodiments, the cleaning composition comprises an engineered fatty acid alpha-dioxygenase, wherein said engineered fatty acid alpha-dioxygenase is present in an amount of from 0.0001 wt % to 1 wt %, preferably from 0.001 wt % to 0.2 wt %, by weight of the cleaning composition, based on active protein.

In embodiments, the consumer product further comprises one or more co-enzymes selected from the group consisting of: fatty-acid peroxidases (EC 1.11.1.3), unspecific peroxygenases (EC 1.11.2.1), plant seed peroxygenases (EC 1.11.2.3), fatty acid peroxygenases (EC1.11.2.4), linoleate diol synthases (EC 1.13.11.44), 5,8-linoleate diol synthases (EC 1.13.11.60 and EC 5.4.4.5), 7,8-linoleate diol synthases (EC 1.13.11.60 and EC 5.4.4.6), 9,14-linoleate diol synthases (EC 1.13.11.B1), 8,11-linoleate diol synthases, oleate diol synthases, other linoleate diol synthases, unspecific monooxygenase (EC 1.14.14.1), alkane 1-monooxygenase (EC 1.14.15.3), oleate 12-hydroxylases (EC 1.14.18.4), fatty acid amide hydrolases (EC 3.5.1.99), fatty acid photodecarboxylases (EC 4.1.1.106), oleate hydratases (EC 4.2.1.53), linoleate isomerases (EC 5.2.1.5), linoleate (10E,12Z)-isomerases (EC 5.3.3.B2), P450 fatty acid decarboxylases (OleT-like), non-heme fatty acid decarboxylases (UndA-like), amylases, lipases, proteases, cellulases, and mixtures thereof; preferably fatty-acid peroxidases (EC 1.11.1.3), unspecific peroxygenases (EC 1.11.2.1), plant seed peroxygenases (EC 1.11.2.3), and fatty acid peroxygenases (EC1.11.2.4), non-heme fatty acid decarboxylases (UndA-like), fatty acid decarboxylases (OleT-like), and mixtures thereof.

Where necessary, the composition comprises, provides access to, or forms in situ any additional substrate necessary for the effective functioning of the enzyme. For example, molecular oxygen can be provided as an additional substrate for fatty acid alpha-dioxygenases. Molecular oxygen can be obtained from the atmosphere or from a precursor that can be transformed to produce oxygen in situ. In many applications, oxygen from the atmosphere can be present in sufficient amounts. In embodiments, the cleaning composition may be supplemented with heme and/or a source of iron to enhance or facilitate the conversion of the fatty acids.

In embodiments, the engineered fatty acid alpha-dioxygenase may comprise a heme cofactor selected from the group comprising: heme a, heme b, heme c, heme d, heme i, heme m, heme o, heme s, their derivatives, and mixtures thereof; preferably heme b. In other embodiments, the heme cofactor is covalently attached to the engineered fatty acid alpha-dioxygenases.

In some embodiments, the engineered fatty acid alpha-dioxygenase may comprise a heme cofactor comprising: a) a porphyrin group and b) a metal. Non-limiting examples of porphyrin groups are: protoporphyrin IX, N-methyl protoporphyrin IX, protoporphyrin IX monomethyl ester, protoporphyrin IX dimethyl ester, protoporphyrin IX diamide, protoporphyrin IX bis thiosulfate, porphin, phthalocyanine, octaethylporphyrin, tetraphenylporphyrin, and their derivatives; preferably protoporphyrin IX. Non-limiting examples of metals are: Mg, Al, V, Cr, Mn, Fe, Co, Ni, Cu, Zn, Ga, Ge, Mo, Tc, Ru, Rh, Pd, Ag, Cd, In, Sn, Sb, W, Re, Os, Ir, Pt, Au, Hg, Tl, Pb, Bi, and mixtures thereof; preferably Fe. In some embodiments, the fatty acid alpha-dioxygenase comprises a heme cofactor comprising a cation selected from the group consisting of: $Mg^{2+}$, $Cr^{3+}$, $Mn^{3+}$, $Fe^{3+}$, $Co^{3+}$, $Ni^{2+}$, $Cu^{2+}$, $Zn^{2+}$, $Ga^{3+}$, $Rh^{2+}$, $Pd^{2+}$, $Ag^{2+}$, $In^{3+}$, $Sn^{4+}$, $VO^{2+}$, and mixtures thereof; preferably $Fe^{3+}$. In some embodiments, the fatty acid alpha-dioxygenase comprises a heme cofactor comprising an axially bound ligand. Non-limiting examples of ligands are: chloride, methyl group, carbonyl group, hydroxide group, and tetrahydrofuran.

Polynucleotides and Plasmids

In another aspect, the present invention provides polynucleotides encoding the engineered fatty acid alpha-dioxygenases. The polynucleotides may be operatively linked to one or more heterologous regulatory sequences that control gene expression to create a recombinant polynucleotide capable of expressing the polypeptide. Expression constructs containing a heterologous polynucleotide encoding the engineered fatty acid alpha-dioxygenase can be introduced into appropriate host cells to express the corresponding engineered fatty acid alpha-dioxygenase polypeptide.

Due to the degeneracy of the genetic code, where the same amino acids are encoded by alternative or synonymous codons, a large number of nucleic acids that encode the engineered fatty acid alpha-dioxygenases disclosed herein can be produced. Those skilled in the art could make any number of different nucleic acids by simply modifying the sequence of one or more codons in a way which does not change the amino acid sequence of the protein. In this regard, the present invention specifically contemplates each and every possible variation of polynucleotides that could be made by selecting combinations based on the possible codon choices, and all such variations are to be considered specifically disclosed for any polypeptide disclosed herein. In various embodiments, the codons are preferably selected to fit the host cell in which the protein is being produced. For example, preferred codons used in bacteria are used to express the gene in bacteria; preferred codons used in yeast are used for expression in yeast; and preferred codons used in mammals are used for expression in mammalian cells.

The polynucleotides encoding the enzyme can be prepared by standard methods, such as solid-phase methods. In embodiments, fragments of up to about 100 bases can be individually synthesized, then joined (e.g., by enzymatic or chemical ligation methods or polymerase mediated methods) to form any desired continuous sequence. For example, polynucleotides and oligonucleotides of the invention can be prepared by chemical synthesis (e.g., using the classical phosphoramidite method described by Beaucage et al., Tet. Lett., 22:1859-69 [1981], or the method described by Matthes et al., EMBO J., 3:801-05 [1984], as it is typically practiced in automated synthetic methods). According to the phosphoramidite method, oligonucleotides are synthesized (e.g., in an automatic DNA synthesizer), purified, annealed, ligated and cloned in appropriate vectors.

In embodiments, the polynucleotide encodes an engineered fatty acid alpha-dioxygenase polypeptide sequence having at least about 70% identity to SEQ ID NO: 1 and its functional fragments thereof; wherein said polypeptide sequence comprises at least one amino acid substitution at positions selected from the group consisting of: L53, N54, R57, 572, G74, D117, S121, Q153, V156, H157, D158, M160, D199, G200, T210, W212, D214, S216, E224, R225, K232, K248, E249, E285, E286, T316, L319, L320, K323, M325, A328, M329, N332, T344, L356, H382, E399, A400, F453, S508, K510, K540, F549, F552, I553, S557, and mixtures thereof; wherein said positions are numbered with reference to SEQ ID NO: 1; and wherein said engineered fatty acid alpha-dioxygenase catalyzes the conversion of at least one fatty acid selected from the group consisting of: stearic acid, oleic acid, linoleic acid, linolenic acid, and mixtures thereof.

An isolated polynucleotide encoding an engineered fatty acid alpha-dioxygenase polypeptide may be manipulated in a variety of ways to provide for expression of the polypeptide. Manipulation of the isolated polynucleotide prior to its insertion into a vector may be desirable or necessary depending on the expression vector. The techniques for modifying polynucleotides and nucleic acid sequences utilizing recombinant DNA methods are well known in the art.

For bacterial host cells, suitable promoters for directing transcription of the nucleic acid constructs of the present invention, include the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (See, e.g., Villa-Kamaroff et al., Proc. Natl. Acad. Sci. USA 75: 3727-3731 [1978]), as well as the tac promoter (See, e.g., DeBoer et al., Proc. Natl Acad. Sci. USA 80: 21-25 [1983]). Additional suitable promoters are known to those in the art.

For filamentous fungal host cells, suitable promoters for directing the transcription of the nucleic acid constructs of the present invention include promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (WO 96/00787), as well as the NA2-tpi promoter (a hybrid of the promoters from the genes for *Aspergillus niger* neutral alpha-amylase and *Aspergillus oryzae* triose phosphate isomerase), and mutant, truncated, and hybrid promoters thereof.

In a yeast host, useful promoters include, but are not limited to those from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase, as well as other useful promoters for yeast host cells (See, e.g., Romanos, et al., Yeast 8:423-488 [1992]).

A transcription terminator sequence, a sequence recognized by a host cell to terminate transcription, can be operably linked to the 3' terminus of the nucleic acid sequence encoding the polypeptide. Any terminator that is functional in the host cell of choice may be used in the present invention. For example, exemplary transcription terminators for filamentous fungal host cells can be obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease. Exemplary terminators for yeast host cells can be obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase, as well as other useful terminators for yeast host cells known in the art (See, e.g. Romanos et al., supra).

A leader sequence, a nontranslated region of an mRNA that is important for translation by the host cell, can be operably linked to the 5' terminus of the nucleic acid sequence encoding the polypeptide. Any leader sequence that is functional in the host cell of choice may be used. Exemplary leaders for filamentous fungal host cells are obtained from the genes for *Aspergillus oryzae* TAKA amylase and *Aspergillus nidulans* triose phosphate isomerase. Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

Any polyadenylation sequence which is functional in the host cell of choice may be used in the present invention. A polyadenylation sequence is a sequence operably linked to the 3' terminus of the nucleic acid sequence and which, when transcribed, is recognized by the host cell as a signal to add polyadenosine residues to transcribed mRNA. Exemplary polyadenylation sequences for filamentous fungal host cells can be from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase., as well as additional useful polyadenylation sequences for yeast host cells known in the art (See, e.g., Guo et al., Mol. Cell. Biol., 15:5983-5990 [1995]).

The 5' end of the coding sequence of the nucleic acid sequence may inherently contain a signal peptide coding region naturally linked in translation reading frame with the segment of the coding region that encodes the secreted polypeptide. A signal peptide coding region encodes for an amino acid sequence linked to the amino terminus of a polypeptide and directs the encoded polypeptide into the cell's secretory pathway. Alternatively, the 5' end of the coding sequence may contain a signal peptide coding region that is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used in the present invention.

Effective signal peptide coding regions for bacterial host cells are the signal peptide coding regions obtained from the genes for *Bacillus* NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA, as well as additional signal peptides known in the art (See, e.g., Simonen et al., Microbiol. Rev., 57: 109-137 [1993]). Effective signal peptide coding regions for filamentous fungal host cells include, but are not limited to the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase. Useful signal peptides for yeast host cells can be from the genes for *Saccharomyces cerevisiae* alpha-factor and *Saccharomyces cerevisiae* invertase, as well as additional useful signal peptide coding regions (See, e.g., Romanos et al., 1992, supra).

A propeptide coding region encodes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* lactase (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences, which allow the regulation of the expression of the polypeptide relative to the growth of the host cell. Examples of regulatory systems are those which cause the expression of the gene to be turned on or off in response to a chemical or physical stimulus, including the presence of a regulatory compound. In prokaryotic host cells, suitable regulatory sequences include the lac, tac, and trp operator systems. In yeast host cells, suitable regulatory systems include, as examples, the ADH2 system or GAL1 system. In filamentous fungi, suitable regulatory sequences include the TAKA alpha-amylase promoter, *Aspergillus niger* glucoamylase promoter, and *Aspergillus oryzae* gluco amylase promoter.

Other examples of regulatory sequences are those which allow for gene amplification. In eukaryotic systems, these include the dihydrofolate reductase gene, which is amplified in the presence of methotrexate, and the metallothionein genes, which are amplified with heavy metals. In these cases, the nucleic acid sequence encoding the alpha-dioxygenase polypeptide of the present invention would be operably linked with the regulatory sequence.

In embodiments, the present invention may also be directed to a recombinant expression vector comprising a polynucleotide encoding an engineered fatty acid alpha-dioxygenase polypeptide or a variant thereof, and one or more expression regulating regions such as a promoter and a terminator, a replication origin, etc., depending on the type of hosts into which they are to be introduced. The various nucleic acid and control sequences described above may be joined together to produce a recombinant expression vector, which may include one or more convenient restriction sites to allow for insertion or substitution of the nucleic acid sequence encoding the polypeptide at such sites. Alternatively, the nucleic acid sequence of the present invention may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus), which can be conveniently subjected to recombinant DNA procedures and can bring about the expression of the polynucleotide sequence. The choice of the vector will typically depend on the compatibility of the vector with the host cell into which the vector is to be introduced. The vectors may be linear or closed circular plasmids. The expression vector may be an autonomously replicating vector (i.e., a vector that exists as an extrachromosomal entity), the replication of which is independent of chromosomal replication, (e.g., a plasmid, an extrachromosomal element, a minichromosome, or an artificial chromosome). The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used. In another aspect, the present invention provides a plasmid comprising at least one recombinant polynucleotide encoding the engineered fatty acid alpha-dioxygenases.

The expression vector of the present invention preferably contains one or more selectable markers, which permit easy selection of transformed cells. A selectable marker can be a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers, which confer antibiotic resistance such as ampicillin, kanamycin, chloramphenicol, or tetracycline resistance. Suitable markers for yeast host cells are ADE2, HIS3, LEU2, LYS2, MET3, TRP1, and URA3.

Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Embodiments for use in an *Aspergillus* cell include the amdS and pyrG genes of *Aspergillus nidulans* or *Aspergillus oryzae* and the bar gene of *Streptomyces hygroscopicus*.

The expression vectors of the present invention can contain one or more element(s) that permit integration of the vector into the host cell's genome or autonomous replication of the vector in the cell independent of the genome. For integration into the host cell genome, the vector may rely on the nucleic acid sequence encoding the polypeptide or any other element of the vector for integration of the vector into the genome by homologous or nonhomologous recombination.

Alternatively, the expression vector may contain additional nucleic acid sequences for directing integration by homologous recombination into the genome of the host cell. The additional nucleic acid sequences enable the vector to be integrated into the host cell genome at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Non-limiting examples of bacterial origins of replication are P15A on or the origins of replication of plasmids pBR322, pUC19, pACYC177 (which plasmid has the P15A ori), or pACYC184 permitting replication in *E. coli*, and pUB110, pE194, or pTA1060, permitting replication in *Bacillus*. Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes it's functioning temperature-sensitive in the host cell (See, e.g., Ehrlich, Proc. Natl. Acad. Sci. USA 75:1433 [1978]).

More than one copy of a nucleic acid sequence of the present invention may be inserted into a host cell to increase production of the gene product. An increase in the copy number of the nucleic acid sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent.

Many of the expression vectors for use in the present invention are commercially available. Suitable commercial expression vectors include, but are not limited to, p3×FLAG™ expression vectors (Sigma-Aldrich), which include a CMV promoter and hGH polyadenylation site for expression in mammalian host cells and a pBR322 origin of replication and ampicillin resistance markers for amplification in *E. coli*. Other commercially available suitable expression vectors include but are not limited to the pBluescriptII SK(−) and pBK-CMV vectors (Stratagene), and plasmids derived from pBR322 (Gibco BRL), pUC (Gibco BRL), pREP4, pCEP4 (Invitrogen) or pPoly (See, Lathe et al., Gene 57:193-201 [1987]).

The skilled person will appreciate that, upon production of an enzyme, in particular, depending upon the cell line used and the particular amino acid sequence of the enzyme, post-translational modifications may occur. For example, such post-translational modifications may include the cleavage of certain leader sequences, the addition of various sugar moieties in various glycosylation and phosphorylation patterns, deamidation, oxidation, disulfide bond scrambling, isomerisation, C-terminal lysine clipping, and N-terminal glutamine cyclisation. The present invention encompasses the use of alpha-dioxygenase enzymes that have been subjected to, or have undergone, one or more post-translational modifications. Thus, the alpha-dioxygenases of the invention include one which has undergone a post-translational modification, such as described herein.

Deamidation is an enzymatic reaction primarily converting asparagine (N) to iso-aspartic acid (iso-aspartate) and aspartic acid (aspartate) (D) at approximately 3:1 ratio. This deamidation reaction is, therefore, related to isomerization of aspartate (D) to iso-aspartate. The deamidation of asparagine and the isomerisation of aspartate, both involve the intermediate succinimide. To a much lesser degree, deamidation can occur with glutamine residues in a similar manner. Oxidation can occur during production and storage (i.e., in the presence of oxidizing conditions) and results in a covalent modification of a protein, induced either directly by reactive oxygen species, or indirectly by reaction with secondary by-products of oxidative stress. Oxidation happens primarily with methionine residues, but may occur at tryptophan and free cysteine residues. Disulfide bond scrambling can occur during production and basic storage conditions. Under certain circumstances, disulfide bonds can break or form incorrectly, resulting in unpaired cysteine residues (—SH). These free (unpaired) sulfhydryls (—SH) can promote shuffling. N-terminal glutamine (Q) and glutamate (glutamic acid) (E) in the alpha-dioxygenases are likely to form pyroglutamate (pGlu) via cyclization. Most pGlu formation happens in manufacturing, but it can be formed non-enzymatically, depending upon pH and temperature of processing and storage conditions. C-terminal lysine clipping is an enzymatic reaction catalyzed by carboxypeptidases and is commonly observed in enzymes. Variants of this process include removal of lysine from the enzymes from the recombinant host cell. In the present invention, the post-translational modifications and changes in primary amino acid sequence described above do not result in significant changes in the activity of the alpha-dioxygenase enzymes.

Host Cells for Expression of Engineered Fatty Acid Alpha-Dioxygenase Polypeptides In another aspect, the present invention provides a host cell comprising a polynucleotide encoding an engineered fatty acid alpha-dioxygenase polypeptide of the present invention, the polynucleotide being operatively linked to one or more control sequences for expression of the engineered fatty acid alpha-dioxygenase the host cell. In embodiments, the host cell are selected from eukaryotic and prokaryotic organisms. Host cells for use in expressing the engineered fatty acid alpha-dioxygenase polypeptides encoded by the expression vectors of the present invention are well known in the art and include but are not limited to bacterial cells, (e.g. *E. coli, Bacillus subtilis, Geobacillus stearothermophilus, Pseudomonas aeruginosa, Lactobacillus kefir, Lactobacillus brevis, Lactobacillus minor, Mycobacterium tuberculosis, Streptomyces coelicolor* and *Salmonella typhimurium*), fungal cells (e.g. *Trichoderma reesei* and *Aspergillus niger*), yeast cells (e.g., *Saccharomyces cerevisiae, Kluyveromyces lactis* or *Pichia pastoris*), insect cells (e.g. *Drosophila* S2 and *Spodoptera* Sf9), animal cells (e.g. CHO, COS, BHK, 293, and Bowes melanoma cells), and plant cells (e.g. *Nicotiana* genus and *Zea mays*). Appropriate culture media and growth conditions for the above-described host cells are well known in the art.

Host cells of the present invention may also include, for example, host cells that produce excess quantities of free fatty acids. Host cells that produce excess quantities of free fatty acids may be modified to produce excess quantities of free fatty acids as compared to a corresponding unmodified host cell. The modification may be, for example, genetic modification. Where the modification is a genetic modification, a corresponding unmodified host cell may be, for example, a host cell that lacks the same genetic modification facilitating the production of excess quantities of free fatty acids in the modified host cell. Host cells that produce excess quantities of free fatty acids, as well as methods of making such host cells, are known in the art. In embodiments, beta-oxidation may be eliminated in the host cell, which leads to reduced utilization of fatty acids. Elimination of beta-oxidation in a host cell such as, for example, *E. coli*, may be accomplished via a ΔfadD deletion, or deletion of a homolog of fadD. In embodiments, the host cell is engineered to encourage production of fatty acids from precursors. This may be accomplished, for example, by the overexpression of one or more thioesterases such as, for example, TesA' and FatB1, from *Cinnamomum* camphorum. In embodiments, the host cell is engineered to encourage production of malonyl-coA, which is involved in elongating fatty acid chains. This may be accomplished, for example, by the overexpression of an acetyl-coA carboxylase (ACC) such as, for example, the acetyl-coA carboxylase (ACC) from *E. coli*. In embodiments, the host cell is engineered to limit the fatty acid yield to shorter chain fatty acids in the C12-C14 range. This may be accomplished, for example, by the overexpression of the thioesterase from *Umbellularia californica* (UcTE) (Lennen et al., Trends in Cell Biology 30:12, pp. 659-667, 2012). In embodiments, the host cell is engineered for reverse beta-oxidation. Host cells such as, for example, *E. coli*, may be engineered for reverse beta-oxidation by, for example, reducing or eliminating the activity of the fadR, atoC(c), crp, arcA, adhE, pta, frdA, fucO, yghD, and fadD genes or homologs thereof, as well as overexpressing FadBA and at least one thioesterase from the group including TesA TesB, FadM, and YciA, or homologs thereof. The particular thioesterase overexpressed may impact the chain length distribution of the final products (Dellomonaco et al., Nature 475, pp. 355-359, 2011). In embodiments, host cells of the present disclosure may overexpress a FatB2 protein from *Umbellularia californica*, which may be codon-optimized.

Polynucleotides for expression of the engineered fatty acid alpha-dioxygenase may be introduced into cells by various methods known in the art. Techniques include among others, electroporation, biolistic particle bombardment, liposome mediated transfection, calcium chloride transfection, and protoplast fusion. Various methods for introducing polynucleotides into cells will be apparent to the skilled artisan.

Methods of Producing Engineered Fatty Acid Alpha-Dioxygenase Polypeptides

In embodiments, methods for producing at least one engineered fatty acid alpha-dioxygenase are provided, wherein said methods comprise culturing the host cell under conditions such that said engineered fatty acid alpha-dioxygenase is produced by said host cell. In embodiments, the methods further comprise the step of recovering said engineered fatty acid alpha-dioxygenase. In other embodiments, the methods further comprise the step of purifying said engineered fatty acid alpha-dioxygenase.

Standard methods of culturing organisms such as, for example, bacteria and yeast, for production of enzymes are well-known in the art and are described herein. For example, host cells may be cultured in a standard growth media under standard temperature and pressure conditions, and in an aerobic environment. Standard growth media for various host cells are commercially available and well-known in the art, as are standard conditions for growing various host cells.

Engineered fatty acid alpha-dioxygenase enzymes expressed in a host cell can be recovered from the cells and or the culture medium using any one or more of the well-known techniques for protein purification, including, among others, lysozyme treatment, sonication, filtration, salting-out, ultra-centrifugation, and chromatography. Suitable solutions for lysing and the high efficiency extraction of proteins from bacteria, such as *E. coli*, are commercially available under the trade name CelLytic B (Sigma-Aldrich). Chromatographic techniques for isolation of the engineered fatty acid alpha-dioxygenase polypeptide include, among others, reverse phase chromatography high performance liquid chromatography (HPLC), ion exchange chromatography, gel electrophoresis, and affinity chromatography. Conditions for purifying a particular enzyme will depend, in part, on factors such as net charge, hydrophobicity, hydrophilicity, molecular weight, molecular shape, etc., and will be apparent to those having skill in the art.

The engineered fatty acid alpha-dioxygenases may also be prepared and used in the form of cells expressing the enzymes, as crude extracts, or as isolated or purified preparations. The engineered fatty acid alpha-dioxygenases may be prepared as lyophilizates, in powder form (e.g., acetone powders), or prepared as enzyme solutions. In embodiments, the engineered fatty acid alpha-dioxygenases can be in the form of substantially pure preparations.

Cleaning Compositions

In certain embodiments, the present invention relates to cleaning product compositions comprising an engineered fatty acid alpha-dioxygenase. The cleaning compositions, when used to contact soiled surfaces having disposed thereon soils comprising fatty acid, can convert the fatty acid of the soil into an enzymatic product, such as a 2-hydroperoxy fatty acid. In this regard, the cleaning compositions of the present invention can exhibit improved cleaning performance, or equivalent cleaning performance while utilizing lower levels of surfactant in the cleaning composition. Preferred fatty acids are stearic acid, oleic acid, linoleic acid, and linolenic acid.

Cleaning compositions of the present invention include, but are not limited to, compositions for treating hair (human, dog, and/or cat), including, bleaching, coloring, dyeing, conditioning, growing, removing, retarding growth, shampooing, styling; deodorants and antiperspirants; personal cleansing; products, and/or methods relating to treating skin (human, dog, and/or cat), including application of creams, lotions, and other topically applied products for consumer use; shaving; body sprays; compositions for treating fabrics, hard surfaces and any other surfaces in the area of fabric and home care, including: air care, car care, dishwashing, fabric conditioning (including softening), laundry detergency, laundry and rinse additive and/or care, hard surface cleaning and/or treatment, and other cleaning for consumer or institutional use; hand soaps, shampoos, lotions, oral care implements; products such as wet or dry bath tissue, facial tissue, disposable handkerchiefs, disposable towels, and/or wipes. In preferred aspects, the cleaning composition is a detergent composition.

Preferred cleaning compositions herein include fabric cleaning compositions, hard surface cleaning compositions, dishwashing compositions, and hair cleaning compositions. Such compositions typically comprise a consumer product adjunct ingredient(s).

A cleaning composition of the present invention may be a manual dishwashing composition, preferably in liquid form. It typically contains from 30% to 95%, preferably from 40% to 90%, more preferably from 50% to 85% by weight of the composition of a liquid carrier in which the other essential and optional components are dissolved, dispersed or suspended. One preferred component of the liquid carrier is water.

The pH of a cleaning composition of the present invention, measured as a 10% product concentration in demineralized water at 20° C., may be adjusted to between 3 and 14, more preferably between 4 and 13, more preferably between 6 and 12 and most preferably between 8 and 10. The pH of the cleaning composition can be adjusted using pH modifying ingredients known in the art.

The cleaning composition herein may optionally comprise a number of other cleaning adjunct ingredients such as enzyme stabilizers, surfactants, co-enzymes, salts, hydrotropes, chelants, builders, dispersants, dye transfer inhibitors, bleach, stabilizers/thickeners, perfume, conditioning agents, hueing agents, structurants, solvents, aqueous carrier, and mixtures thereof. Consumer product adjunct ingredients also include scrubbing particles, malodor control agents, pigments, dyes, opacifiers, pH adjusters and buffering means (e.g., carboxylic acids such as citric acid, HCl, NaOH, KOH, alkanolamines, phosphoric and sulfonic acids, carbonates such as sodium carbonates, bicarbonates, sesquicarbonates, borates, silicates, phosphates, imidazole and alike).

In embodiments, the cleaning composition comprises one or more engineered fatty acid alpha-dioxygenases in an amount of from 0.0001 wt % to 1 wt %, preferably from 0.001 wt % to 0.2 wt %, by weight of the cleaning composition, based on active protein.

Enzyme Stabilizers

The composition of the present invention may comprise an enzyme stabilizer, selected from the group consisting of chemical and physical stabilizers, preferably the physical stabilizer comprises encapsulating the enzyme. Suitable enzyme stabilizers may be selected from the group consisting of (a) univalent, bivalent and/or trivalent cations preferably selected from the group of inorganic or organic salts of alkaline earth metals, alkali metals, aluminum, iron, copper and zinc, preferably alkali metals and alkaline earth metals, preferably alkali metal and alkaline earth metal salts with halides, sulfates, sulfites, carbonates, hydrogencarbonates, nitrates, nitrites, phosphates, formates, acetates, propionates, citrates, maleates, tartrates, succinates, oxalates, lactates, and mixtures thereof. In a preferred embodiment the salt is selected from the group consisting of sodium chloride, calcium chloride, potassium chloride, sodium sulfate, potassium sulfate, sodium acetate, potassium acetate, sodium formate, potassium formate, calcium lactate, calcium nitrate and mixtures thereof. Most preferred are salts selected from the group consisting of calcium chloride, potassium chloride, potassium sulfate, sodium acetate, potassium acetate, sodium formate, potassium formate, calcium lactate, calcium nitrate, and mixtures thereof, and in particular potassium salts selected from the group of potassium chloride, potassium sulfate, potassium acetate, potassium formate, potassium propionate, potassium lactate and mixtures thereof. Most preferred are potassium acetate and potassium chloride. Preferred calcium salts are calcium formate, calcium lactate and calcium nitrate including calcium nitrate tetrahydrate. Calcium and sodium formate salts may be preferred. These cations are present at at least about 0.01 wt %, preferably at least about 0.03 wt %, more preferably at least about 0.05 wt %, most preferably at least about 0.25 wt % up to 2 wt % or even up to 1 wt % by weight of the total composition. These salts are formulated from 0.1 wt % to 5 wt %, preferably from 0.2 wt % to 4 wt %, more preferably from 0.3 wt % to 3 wt %, most preferably from 0.5 wt % to 2 wt % relative to the total weight of the composition. Further enzyme stabilizers can be selected from the group (b) carbohydrates selected from the group consisting of oligosaccharides, polysaccharides and mixtures thereof, such as a monosaccharide glycerate as described in WO201219844; (c) mass efficient reversible protease inhibitors selected from the group consisting of phenyl boronic acid and derivatives thereof, preferably 4-formyl phenylboronic acid; (d) alcohols such as 1,2-propane diol, propylene glycol; (e) peptide aldehyde stabilizers such as tripeptide aldehydes such as Cbz-Gly-Ala-Tyr-H, or disubstituted alaninamide; (f) carboxylic acids such as phenyl alkyl dicarboxylic acid as described in WO2012/19849 or multiply substituted benzyl carboxylic acid comprising a carboxyl group on at least two carbon atoms of the benzyl radical such as described in WO2012/19848, phthaloyl glutamine acid, phthaloyl asparagine acid, aminophthalic acid and/or an oligoamino-biphenyl-oligocarboxylic acid; and (g) mixtures thereof.

Antioxidants

Antioxidant compounds and free radical scavengers can generally protect enzyme from degradation by preventing excessive generation of singlet oxygen and peroxy radicals that promote alteration of enzyme structure leading to short TON of Enzymes. Not to be limited by theory, a general discussion of the mode of action for antioxidants and free radical scavengers is disclosed in Kirk Othmer, The Encyclopedia of Chemical Technology, Volume 3, pages 128-148, Third Edition (1978).

The composition may optionally contain an anti-oxidant present from about 0.001 to about 2% by weight. Preferably the antioxidant is present at a concentration in the range 0.01 to 0.1% by weight. Mixtures of anti-oxidants may be used and in some embodiments, may be preferred. One or more antioxidants may be incorporated the composition.

One class of anti-oxidants used in the present invention is alkylated phenols, having the general formula:

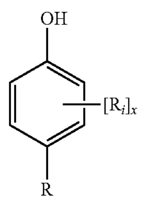

wherein R is C1-C22 linear or branched alkyl, preferably methyl or branched C3-C6 alkyl, C1-C6 alkoxy, preferably methoxy, or CH2CH2C(O)OR', wherein R' is H, a charge balancing counterion or C1-C22 linear or branched alkyl; Ri is a C3-C6 branched alkyl, preferably tert-butyl; x is 1 or 2. Hindered phenolic compounds are a preferred type of alkylated phenols having this formula. A preferred hindered phenolic compound of this type is 3,5-di-tert-butyl-4-hydroxytoluene (BHT).

Furthermore, the anti-oxidant used in the composition may be selected from the group consisting of a-, b-, g-, d-tocopherol, ethoxyquin, 2,2 4-trimethyl-1,2-dihydroquinoline, 2,6-di-tert-butyl hydroquinone, tert-butyl hydroxyanisole, lignosulphonic acid and salts thereof, and mixtures thereof. It is noted that ethoxyquin (1,2-dihydro-6-ethoxy-2,2,4-trimethylquinoline) is marketed under the name Raluquin™ by the company Raschig™. Other types of anti-oxidants that may be used in the composition are 6-hydroxy-2, 5,7,8-tetramethylchroman-2-carboxylic acid (Trolox™) and 1,2-benzisothiazoline-3-one (Proxel GXL™).

A further class of anti-oxidants which may be suitable for use in the composition is a benzofuran or benzopyran derivative having the formula:

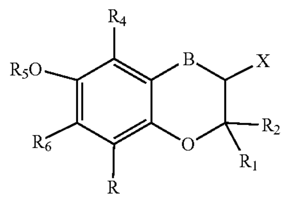

wherein R1 and R2 are each independently linear or branched C1-C22 alkyl or R1 and R2 can be taken together to form a C5-C6 cyclic hydrocarbyl moiety; B is absent or CH2; R4 is C1-C4 alkyl; R5 is hydrogen or —C(O)R3 wherein R3 is hydrogen or C1-C19 alkyl; R6 is C1-C4 alkyl; R7 is hydrogen or C1-C4 alkyl; X is —CH2OH, or —CH2A wherein A is a nitrogen comprising unit, phenyl, or substituted phenyl. Preferred nitrogen comprising A units include amino, pyrrolidino, piperidino, morpholino, piperazino, and mixtures thereof.

Anti-oxidants such as tocopherol sorbate, butylated hydroxyl benzoic acids and their salts, gallic acid and its alkyl esters, ascorbic, citric, tartric, uric acid and its salts, sorbic acid and its salts, and dihydroxyfumaric acid and its salts may also be used. In one aspect, the most preferred types of anti-oxidant for use in the composition are 3,5-di-tert-butyl-4-hydroxytoluene (BHT), a-, b-, g-, d-tocopherol, 1,2-benzisothiazoline-3-one (Proxel GXL™) anthocyanins, carotene, catechins, flavonoids, lutein, lycopene and mixtures thereof. In another aspect, the most preferred types of anti-oxidant for use in the composition are hindered phenols, diarylamines (including phenoxazines with a maximum molar extinction coefficient in the wavelength range from 400 to 750 nm of less than 1,000 $M^{-1}$ $cm^{-1}$), and mixtures thereof. In preferred mixtures, the number of equivalents of hindered phenol initially formulated will normally be greater than or equal to the number of equivalents of diarylamine.

Surfactants

The cleaning compositions of the present invention may comprise greater than about 0.1% by weight of a surfactant or mixture of surfactants. Surfactant levels cited herein are on a 100% active basis, even though common raw materials such as sodium lauryl sulphate may be supplied as aqueous solutions of lower activity. In embodiments of the present invention, a cleaning composition may include surfactant in an amount of from about 1 wt % to about 60 wt %, from about 5 wt % to about 50 wt %, by weight of the cleaning composition.

Suitable surfactants for use herein include anionic surfactants, nonionic surfactants, zwitterionic surfactants, amphoteric surfactants, cationic surfactants, and mixtures thereof. In embodiments, the cleaning composition comprises one or more anionic surfactants and one or more co-surfactants selected from the group consisting of amphoteric surfactant, zwitterionic surfactant, and mixtures thereof.

Useful anionic surfactants herein include the water-soluble salts of alkyl sulphates and alkyl ether sulphates having from 10 to 18 carbon atoms in the alkyl radical and the water-soluble salts of sulphonated monoglycerides of fatty acids having from 10 to 18 carbon atoms. Sodium lauryl sulphate and sodium coconut monoglyceride sulphonates are examples of anionic surfactants of this type.

Suitable cationic surfactants useful in the present invention can be broadly defined as derivatives of aliphatic quaternary ammonium compounds having one long alkyl chain containing from about 8 to 18 carbon atoms such as lauryl trimethylammonium chloride; cetyl pyridinium chloride; benzalkonium chloride; cetyl trimethylammonium bromide; di-isobutylphenoxyethyl-dimethylbenzylammonium chloride; coconut alkyltrimethyl-ammonium nitrite; cetyl pyridinium fluoride; etc. Certain cationic surfactants can also act as germicides in the compositions disclosed herein.

Suitable nonionic surfactants that can be used in the compositions of the present invention can be broadly defined as compounds produced by the condensation of alkylene oxide groups (hydrophilic in nature) with an organic hydrophobic compound which may be aliphatic and/or aromatic in nature. Examples of suitable nonionic surfactants include the poloxamers; sorbitan derivatives, such as sorbitan di-isostearate; ethylene oxide condensates of hydrogenated castor oil, such as PEG-30 hydrogenated castor oil; ethylene oxide condensates of aliphatic alcohols or alkyl phenols; products derived from the condensation of ethylene oxide with the reaction product of propylene oxide and ethylene diamine; long chain tertiary amine oxides; long chain tertiary phosphine oxides; long chain dialkyl sulphoxides and mixtures of such materials. These materials are useful for stabilising foams without contributing to excess viscosity build for the cleaning composition.

Zwitterionic surfactants can be broadly described as derivatives of aliphatic quaternary ammonium, phosphonium, and sulphonium compounds, in which the aliphatic radicals can be straight chain or branched, and wherein one of the aliphatic substituents contains from about 8 to 18 carbon atoms and one contains an anionic water-solubilising group, e.g., carboxy, sulphonate, sulphate, phosphate or phosphonate.

Surfactants can provide a desirable foaming quality. Suitable surfactants are those which are reasonably stable and foam throughout a wide pH range. The surfactant may be anionic, nonionic, amphoteric, zwitterionic, cationic, or mixtures thereof. Anionic surfactants useful herein include the water-soluble salts of alkyl sulfates having from 8 to 20 carbon atoms in the alkyl radical (e.g., sodium alkyl sulfate) and the water-soluble salts of sulfonated monoglycerides of fatty acids having from 8 to 20 carbon atoms. Sodium lauryl sulfate and sodium coconut monoglyceride sulfonates are examples of anionic surfactants of this type. Other suitable anionic surfactants are sarcosinates, such as sodium lauroyl sarcosinate, taurates, sodium lauryl sulfoacetate, sodium lauroyl isethionate, sodium laureth carboxylate, and sodium dodecyl benzenesulfonate. Mixtures of anionic surfactants can also be employed. Many suitable anionic surfactants are disclosed by Agricola et al., U.S. Pat. No. 3,959,458, issued May 25, 1976, incorporated herein in its entirety by reference. Nonionic surfactants which can be used in the compositions of the present invention can be broadly defined as compounds produced by the condensation of alkylene oxide groups (hydrophilic in nature) with an organic hydrophobic compound which may be aliphatic or alkyl-aromatic in nature. Examples of suitable nonionic surfactants include poloxamers (sold under trade name Pluronic), polyoxyethylene, polyoxyethylene sorbitan esters (sold under trade name Tweens), fatty alcohol ethoxylates, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides, and mixtures of such materials. The amphoteric surfactants useful in the present invention can be broadly described as derivatives of aliphatic secondary and tertiary amines in which the aliphatic radical can be a straight chain or branched and wherein one of the aliphatic substituents contains from about 8 to about 18 carbon atoms and one contains an anionic water-solubilizing group, e.g., carboxylate, sulfonate, sulfate, phosphate, or phosphonate. Other suitable amphoteric surfactants are betaines, specifically cocamidopropyl betaine. Mixtures of amphoteric surfactants can also be employed. Many of these suitable nonionic and amphoteric surfactants are disclosed by Gieske et al., U.S. Pat. No. 4,051,234, issued Sep. 27, 1977, incorporated herein by reference in its entirety. The present composition typically comprises one or more surfactants each at a level of from about 0.1% to about 25%, preferably from about 0.5% to about 8%, and most preferably from about 1% to about 6%, by weight of the composition.

Source of Hydrogen Peroxide

It may be preferred for the composition to comprise a source of hydrogen peroxide. Sources of hydrogen peroxide include, for example, inorganic perhydrate salts, including alkali metal salts such as sodium salts of perborate (usually mono- or tetra-hydrate), percarbonate, persulphate, perphosphate, persilicate salts and mixtures thereof. In one aspect of the invention the inorganic perhydrate salts are selected from the group consisting of sodium salts of perborate, percarbonate and mixtures thereof. In some compositions, percarbonate salts are preferred. When employed, inorganic perhydrate salts are typically present in amounts of from 0.05 to 40 wt %, or 1 to 30 wt % of the overall cleaning composition and are typically incorporated into such compositions as a crystalline solid that may be coated. Suitable coatings include, inorganic salts such as alkali metal silicate, carbonate or borate salts or mixtures thereof, or organic materials such as water-soluble or dispersible polymers, waxes, oils or fatty soaps. These may be present in combination with bleach activators and/or bleach catalysts. In other compositions, hydrogen peroxide is preferred. When employed, hydrogen peroxide is typically present in amounts of from 0.05 to 40 wt %, or 1 to 30 wt % of the overall cleaning composition.

Suitable bleach activators are those having R—(C═O)-L wherein R is an alkyl group, optionally branched, having, when the bleach activator is hydrophobic, from 6 to 14 carbon atoms, or from 8 to 12 carbon atoms and, when the bleach activator is hydrophilic, less than 6 carbon atoms or even less than 4 carbon atoms; and L is leaving group. Examples of suitable leaving groups are benzoic acid and derivatives thereof—especially benzene sulphonate. Suitable bleach activators include dodecanoyl oxybenzene sulphonate, decanoyl oxybenzene sulphonate, decanoyl oxybenzoic acid or salts thereof, 3,5,5-trimethyl hexanoyloxybenzene sulphonate, tetraacetyl ethylene diamine (TAED) and nonanoyloxybenzene sulphonate (NOBS). While any suitable bleach activator may be employed, it may be preferred if the subject composition comprises NOBS, TAED or mixtures thereof.

Suitable bleach catalysts include one or more bleach catalysts capable of accepting an oxygen atom from a peroxyacid and/or salt thereof and transferring the oxygen atom to an oxidizable substrate. Suitable bleach catalysts include, but are not limited to: iminium cations and polyions; iminium zwitterions; modified amines; modified amine oxides; N-sulphonyl imines; N-phosphonyl imines; N-acyl imines; thiadiazole dioxides; perfluoroimines; cyclic sugar ketones and alpha amino-ketones and mixtures thereof.

Suitable bleach catalysts include oxaziridinium bleach catalysts, transition metal bleach catalysts, especially manganese and iron bleach catalysts. A suitable bleach catalyst has a structure corresponding to general formula below:

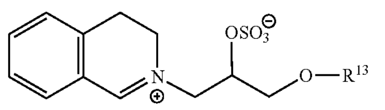

wherein $R^{13}$ is selected from the group consisting of 2-ethylhexyl, 2-propylheptyl, 2-butyloctyl, 2-pentylnonyl, 2-hexyldecyl, n-dodecyl, n-tetradecyl, n-hexadecyl, n-octadecyl, iso-nonyl, iso-decyl, iso-tridecyl and iso-pentadecyl.

Another suitable source of hydrogen peroxide includes pre-formed peracids. Suitable preformed peracids include, but are not limited to compounds selected from the group consisting of pre-formed peroxyacids or salts thereof typically a percarboxylic acids and salts, percarbonic acids and salts, perimidic acids and salts, peroxymonosulfuric acids and salts, for example, Oxone®, and mixtures thereof. Suitable examples include peroxycarboxylic acids or salts thereof, or peroxysulphonic acids or salts thereof. Typical peroxycarboxylic acid salts suitable for use herein have a chemical structure corresponding to the following chemical formula:

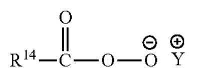

wherein: $R^{14}$ is selected from alkyl, aralkyl, cycloalkyl, aryl or heterocyclic groups; the $R^{14}$ group can be linear or branched, substituted or unsubstituted; having, when the peracid is hydrophobic, from 6 to 14 carbon atoms, or from 8 to 12 carbon atoms and, when the peracid is hydrophilic, less than 6 carbon atoms or even less than 4 carbon atoms and Y is any suitable counter-ion that achieves electric charge neutrality, preferably Y is selected from hydrogen, sodium or potassium. $R^{14}$ may be a linear or branched, substituted or unsubstituted $C_{6-9}$ alkyl. The peroxyacid or salt thereof may be selected from peroxyhexanoic acid, peroxyheptanoic acid, peroxyoctanoic acid, peroxynonanoic acid, peroxydecanoic acid, any salt thereof, or any combination thereof. Peroxyacids that may be used include phthalimido-peroxy-alkanoic acids, in particular F-phthalimido peroxy hexanoic acid (PAP). The peroxyacid or salt thereof may have a melting point in the range of from 30° C. to 60° C.

The pre-formed peroxyacid or salt thereof can also be a peroxysulphonic acid or salt thereof, typically having a chemical structure corresponding to the following chemical formula:

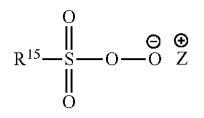

wherein: $R^{15}$ is selected from alkyl, aralkyl, cycloalkyl, aryl or heterocyclic groups; the $R^{15}$ group can be linear or branched, substituted or unsubstituted; and Z is any suitable counter-ion that achieves electric charge neutrality, preferably Z is selected from hydrogen, sodium or potassium. Preferably $R^{15}$ is a linear or branched, substituted or unsubstituted $C_{4-14}$, preferably $C_{6-14}$ alkyl. Preferably such bleach components may be present in the compositions of the invention in an amount from 0.01 to 50%, most preferably from 0.1% to 20%.

Hydrogen peroxide may also be provided by the incorporation of one or more hydrogen peroxide producing enzymes such as alcohol oxidoreductases, aldehyde oxidoreductases, amino acid oxidoreductases, and monoamine oxidases. These enzymes can convert in situ (e.g. in the washing process) substrates such as carbohydrates, proteins, amino acids, alcohols, amines, or other substrates either from a soil or from a material also present in the composition, to generate hydrogen peroxide. Since this will tend to generate low levels of hydrogen peroxide this may be preferred. Non-limiting examples of hydrogen peroxide producing enzymes are: glycolate oxidases (EC 1.1.3.1), L-lactate oxidases (EC 1.1.3.2), malate oxidases (EC 1.1.3.3), glucose oxidases (EC 1.1.3.4), glycerol oxidases (EC 1.1.3.B4), hexose oxidases (EC 1.1.3.5), cholesterol oxidases (EC 1.1.3.6), aryl-alcohol oxidases (EC 1.1.3.7), L-gulonolactone oxidases (EC 1.1.3.8), galactose oxidases (EC 1.1.3.9), pyranose oxidases (EC 1.1.3.10), L-sorbose oxidases (EC 1.1.3.11), alcohol oxidases (EC 1.1.3.13), (S)-2-hydroxy-acid oxidases (EC 1.1.3.15), chlorine oxidases (EC 1.1.3.17), secondary-alcohol oxidases (EC 1.1.3.18), long-chain-alcohol oxidases (EC 1.1.3.20), thiamine oxidases (EC 1.1.3.23), nucleoside oxidases (EC 1.1.3.28, EC 1.1.3.39), polyvinyl-alcohol oxidases (EC 1.1.3.30), vanillyl-alcohol oxidases (EC 1.1.3.38), D-mannitol oxidase ((EC 1.1.3.40), alditol oxidases (EC 1.1.3.41), glucooligosaccharide oxidases (EC 1.1.99.B3), cellobiose dehydrogenase (EC 1.1.99.18), aldehyde oxidases (EC 1.2.3.1), pyruvate oxidases (EC 1.2.3.3), oxalate oxidases (EC 1.2.3.4), glyoxylate oxidases (EC 1.2.3.5), D-aspartate oxidases (EC 1.4.3.1), L-amino acid oxidases (EC 1.4.3.2), D-amino acid oxidases (EC 1.4.3.3), monoamine oxidases (EC 1.4.3.4), D-glutamate oxidases (EC 1.4.3.7), ethanolamine oxidases (EC 1.4.3.8), protein-lysine 6-oxidases (EC 1.4.3.13), L-lysine oxidases (EC 1.4.3.14), D-glutamate (D-aspartate) oxidases (EC 1.4.3.15), L-aspartate oxidases (EC 1.4.3.16), glycine oxidases (EC 1.4.3.19), L-lysine 6-oxidases (EC 1.4.3.20), primary-amine oxidases (EC 1.4.3.21), diamine oxidases (EC 1.4.3.22), L-arginine oxidases (EC 1.4.3.25), non-specific polyamine oxidases (EC 1.5.3.17), other alcohol oxidoreductases (EC 1.1.X.X), other aldehyde oxidoreductases (EC 1.2.X.X), other amino acid oxidoreductases or monoamine oxidases (EC 1.3.X.X), and other amine oxidoreductases (EC 1.5.X.X). The hydrogen peroxide producing enzyme can be fused to the fatty acid alpha-dioxygenase to form a single polypeptide or can be independent enzymes.

In some embodiments, the hydrogen peroxide source can be substituted by: a) a source of nicotinamide adenine dinucleotide (NADH) or nicotinamide adenine dinucleotide phosphate (NADPH) and b) an enzymatic redox system. Non-limiting examples of enzymatic redox systems are: the reductase domain of *Bacillus megaterium* CYP102A1 (P450BM3), the RhFred reductase domain from *Rhodococcus* sp. NCIMB 9784, the flavodoxin (Fld)/ferrodoxin reductase (FdR, EC 1.18.1.2 and EC 1.18.1.3) redox system, the putidaredoxin (Pd)/putidaredoxin reductase (PdR, EC 1.18.1.5) system, the rubredoxin/rubredoxin reductase (EC 1.18.1.1 and EC 1.18.1.4) system, and the adrenoxin/adrenodoxin reductase (EC 1.18.1.6) system. In some embodiments, the composition may also comprise a dehydrogenase-based NADH or NADPH regeneration system, such as the phosphonate/phosphonate dehydrogenase (EC 1.20.1.1) system.

Method of Using the Cleaning Composition

The present invention relates to methods of cleaning a surface having disposed thereon a soil comprising one or more fatty acids, said method comprising the steps of: a) contacting said soil disposed on said surface with a cleaning composition comprising an engineered fatty acid alpha-dioxygenase; wherein said engineered fatty acid alpha-dioxygenase comprises a polypeptide sequence having at least about 70% identity to SEQ ID NO: 1 and its functional fragments thereof; wherein said polypeptide sequence comprises at least one amino acid substitution at positions selected from the group consisting of: L53, N54, R57, S72, G74, D117, S121, Q153, V156, H157, D158, M160, D199, G200, T210, W212, D214, S216, E224, R225, K232, K248, E249, E285, E286, T316, L319, L320, K323, M325, A328, M329, N332, T344, L356, H382, E399, A400, F453, S508, K510, K540, F549, F552, I553, S557, and mixtures thereof; wherein said positions are numbered with reference to SEQ ID NO: 1; and wherein said engineered fatty acid alpha-dioxygenase catalyzes the conversion of at least one fatty acid selected from the group consisting of: stearic acid, oleic acid, linoleic acid, linolenic acid, and mixtures thereof; and b) converting said one or more fatty acids of said soil on said surface into one or more materials selected from the group consisting of 2-hydroperoxy fatty acids, 2-hydroperoxy fatty acid derivatives, and mixtures thereof. Suitable examples of 2-hydroperoxy fatty acid derivatives are 2-hydroxy fatty acid and terminal aldehydes.

The method can further comprise the step of removing the cleaning composition from the surface, e.g. by rinsing the composition from the surface (e.g. with water) or mechanically removing the composition from the surface (e.g. by wiping composition from the surface).

The method can further include the step of diluting the cleaning composition with water to form a diluted cleaning composition and then contacting the surface with the diluted cleaning composition.

Preferred surfaces treated with the cleaning composition of the present invention include surfaces selected from the group consisting of hair, skin, fabric, dishware, tableware, and household hard surfaces.

The present invention further relates to methods of cleaning a surface including a method of manually washing soiled articles, preferably dishware, comprising the step of: delivering a composition of the invention into a volume of water to form a wash solution and immersing the soiled articles in the wash solution, wherein the soil on the soiled articles comprise at least one fatty acid selected from the group consisting of: stearic acid, oleic acid, linoleic acid, linolenic acid, and mixtures thereof.

The engineered fatty acid alpha-dioxygenase may be present at a concentration of from 0.005 ppm to 15 ppm, preferably from 0.01 ppm to 5 ppm, more preferably from 0.02 ppm to 0.5 ppm, in an aqueous wash liquor during the washing process. As such, the composition herein will be applied in its diluted form to the soiled surface. Soiled surfaces e.g. dishes are contacted with an effective amount, typically from 0.5 mL to 20 mL (per 25 dishes being treated), preferably from 3 mL to 10 mL, of the cleaning composition of the present invention, preferably in liquid form, diluted in water. The actual amount of cleaning composition used will be based on the judgment of user, and will typically depend upon factors such as the particular product formulation of the composition, including the concentration of active ingredients in the composition, the number of soiled surfaces to be cleaned, the degree of soiling on the surfaces, and the like.

The present invention also includes the use of engineered fatty acid alpha-dioxygenases to provide increased suds longevity in an aqueous wash liquor comprising soil, wherein the soil comprises fatty acid. The enzymes are preferably comprised in a detergent composition, especially a detergent composition of the present invention, which is used for manually washing dishes.

Test Methods

The following assays set forth can be used such that the invention described and claimed herein may be more fully understood.

Test Method 1—Glass Vial Suds Mileage Method

The objective of the glass vial suds mileage test method is to measure the evolution of suds volume over time generated by a certain solution of detergent composition in the presence of a greasy soil, e.g., olive oil. The steps of the method are as follows:

1. Test solutions are prepared by subsequently adding aliquots at room temperature of: a) 10 g of an aqueous detergent solution at specified detergent concentration and water hardness, b) 0 or x ppm of enzyme, and c) 0.11 g of olive oil (Bertolli©, Extra Virgin Olive Oil), into a 40 mL glass vial (dimensions: 95 mm H×27.5 mm D).
2. The test solutions are mixed in the closed test vials by stirring at room temperature for two minutes on a magnetic stirring plate (IKA, model #RTC B S001; VWR magnetic stirrer, catalog #58949-012; 500 RPM), followed by manually shaking for 20 seconds with an upwards downwards movement (about two up and down cycles per second, +/−30 cm up and 30 cm down).
3. Following the shaking, the test solutions in the closed vials are further stirred on a magnetic stirring plate (IKA, model #RTC B S001; VWR magnetic stirrer, catalog #58949-012; 500 RPM) for 60 minutes inside a water bath at 46° C. to maintain a constant temperature.

The samples are then shaken manually for another 20 seconds as described above and the initial suds heights (H1) are recorded with a ruler.

4. The samples are incubated for an additional 30 minutes inside the water bath at 46° C. while stirring (IKA, model #RTC B S001; VWR magnetic stirrer, catalog #58949-012; 500 RPM), followed by manual shaking for another 20 seconds as described above. The final suds heights (H2) are recorded.
5. Enzyme solutions that produce larger suds heights (H1 and H2), preferably combined with lower drops in suds height between H1 and H2, are more desirable.

Test Method 2—Small Sink Suds Mileage Method

The evolution of the suds volume generated by a solution of a liquid detergent composition can be determined while adding soil loads periodically as follows. An aliquot of 500 mL of solution of the liquid detergent composition in 15 dH hard water (final concentration of 0.12 w %, initial temperature 46° C.) and 0 or xppm of alpha-dioxygenase is added into a cylindrical container (dimensions: 150 mm D×150 mm H). The container is incubated in a water bath during the test to maintain the temperature of the solution between 40° C. and 46° C. An initial suds volume is generated in the container by mechanical agitation at 135 rpm for 120 seconds with a paddle (dimensions: 50 mm×25 mm) positioned in the middle of the container.

Then, an aliquot of 0.5 mL of greasy soil (composition: see TABLE 1, 0.5 mL) is dosed into the solution using a 20-mL syringe and an automated pump (KDS Legato 110 Single Syringe I/W Pump; KD Scientific Inc., Holliston, MA), while the paddle rotates into the solution at 135 rpm for 14 seconds. After mixing, the solution is incubated for 166 additional seconds before the next cycle. The soil injecting, paddling, and incubation steps are repeated every 180 seconds until the end-point is reached and the amount of soil additions needed is recorded. The end-point occurs when a clear suds-free ring that circles the impeller at least half way around is observed two or more consecutive times. The complete process is repeated a number of times and the average of the number of additions for all the replicates is calculated for each liquid detergent composition.

Finally, the suds mileage index is then calculated as: (average number of soil additions for test liquid detergent composition containing enzyme)/(average number of soil additions for reference liquid detergent composition without enzyme)×100. Pending on the test purpose the skilled person could choose to select an alternative water hardness, solution temperature, product concentration or soil type.

TABLE 1

| Greasy Soil Composition | |
|---|---|
| Ingredient | Weight % |
| Crisco oil | 12.730 |
| Crisco shortening | 27.752 |
| Lard | 7.638 |
| Refined Rendered Edible Beef Tallow | 51.684 |
| Oleic Acid, 90% (Techn) | 0.139 |
| Palmitic Acid, 99+% | 0.036 |
| Stearic Acid, 99+% | 0.021 |

Test Method 3—Screening Assays

The objective of this method is to select for top performing engineered alpha dioxygenase enzymes. For each enzyme reaction, the corresponding cell pellet (Example 1) was added to a reaction solution containing HEPES buffer (final conc. 100 mM, pH 9) and liquid detergent composition (final concentration of 0.12 wt %) with or without 15 dH hard water and incubated at 37° C. for 5 minutes. Reactions were initiated with the addition of one substrate fatty acid (palmitic acid) or four (palmitic, stearic, linoleic and oleic acid) and placed onto a shaking incubator. Following alpha-dioxygenase reactions, 750 μL reaction was extracted by methyl tert-butyl ether (MTBE), mixed vigorously and centrifuged at 4000 rpm for 10 min. 500 μL of the organic top layer was transferred to a gas chromatography vial and made up to 1 mL with MTBE. Vials were loaded onto the GC (GC, Agilent 7890B, 7693 auto-sampler (Agilent Technologies, Inc., Santa Clara, CA). The aldehyde/s produced from alpha-dioxygenase reactions were quantified. The enzyme that produces more aldehyde product (s) is more desirable (Example 2). The fold improvement of the enzymes is calculated as: (total area of the aldehyde(s) produced by the enzyme reaction)/(total area of the aldehyde(s) produced by the comparative enzyme (SEQ ID NO: 3) reaction).

EXAMPLES

The following examples are provided to further illustrate the present invention and are not to be construed as limitations of the present invention, as many variations of the present invention are possible without departing from its spirit or scope. Sequences (SEQ ID NO: 4 to 23) used in the below EXAMPLES included an N-terminal amino acid sequence containing a His-tag (SEQ ID NO: 24) attached to the "N Terminal" for testing.

Comparative Example—Production of *Oryza Sativa* αDOX

*Oryza sativa* αDOX (SEQ ID NO: 1) is a fatty acid alpha-dioxygenase that converts fatty acids into the corresponding 2-hydroperoxy fatty acids and is included as a comparative example of a "naturally occurring," or "wild-type," (WT) sequence. Other comparative examples comprise a codon optimized gene (SEQ ID NO: 2) encoding for an alpha-dioxygenase variant (of *Oryza sativa* αDOX (SEQ ID NO: 3)), including an N-terminal amino acid sequence containing a His-tag (SEQ ID NO: 3) was designed and synthesized (Genscript, Piscataway, NJ). After gene synthesis, the protein was expressed and purified. In brief, the complete synthetic gene sequence was subcloned into a pET30a vector using the NdeI/HindIII cloning sites. For heterologous expression, *Escherichia coli* BL21 (DE3) cells were transformed using the standard methods known in the art, with the recombinant plasmid and a single colony was inoculated into 25 mL LB medium containing kanamycin (50 mg/L). A pre-starter culture was then inoculated into flasks (100 mL-1 L) containing Magic Media (Thermo Fisher, Catalog #K6803) supplemented with kanamycin (50 mg/L) and incubated at 16° C. for 72 h. At an OD600 nm=0.5-1.0, 5-aminolevulinic acid (final concentration 0.5 mM) was added. Cells were harvested by centrifugation at 5000 rpm and 4° C. and the pellet was lysed using a bacterial cell lysis buffer (B-PER-Themo Fisher, Waltham, MA). After centrifugation, the supernatant was collected, and the protein was purified by one-step purification using HisPur™ Ni-NTA Spin Columns (Thermo Scientific, Catalog #88226) and standard protocols known in the art. The protein was concentrated using a 10 kDa MW cutoff Amicon Ultra centrifugal filter unit (Millipore Sigma, Catalog #UFC901024; Millipore Sigma, Burlington, MA), followed by desalting using a disposable PD-10 desalting column (GE Healthcare Life Sciences, Catalog #17085101; GE Healthcare, Chicago, IL) and a buffer containing 50 mM Tris-HCl, 500 mM NaCl, and 10% Glycerol at pH 8.0. The purified enzyme was stored at −80° C. until use.

Example 1—Transformation and Expression of Enzymes

In total, 188 mutants were designed in silico and gene synthesized into the expression vector pET28a(+). The 188 mutants and wildtype vectors were transformed into *E. coli* expression strain BL21(DE3) (New England Biolabs, Ipswich, MA) following the standard protocol well known in the art with kanamycin as the selection marker. 96-well plates were prepared with 1 mL of 2×YT per well supplemented with 50 μg/mL kanamycin. Each well was inoculated with a colony from each transformation and plates were incubated at 37° C. overnight with shaking at 200 rpm in a thermos-shaker MB 100-4A (Allsheng, Hangzhou, CN). Glycerol stocks of clones were prepared on plates by mixing 500 μL of growth culture with 500 μL of sterile 50% glycerol solution. Glycerol stocks were stored at −80° C.

For expression, cultures were induced by addition of IPTG and 5-aminolevulinic acid (5-ALA) to a final concentration of 0.1 mM and 0.25 mM, respectively. Plates were incubated at 16° C. with shaking at 200 rpm overnight. Following 16 hour/overnight expression, plates were centrifuged at 4000 rpm for 30 minutes and frozen at −80° C. After three subsequent freeze-thaw cycles the pellets were used in enzymatic screening assays (Test method 3).

Example 2—Top Performing Enzymes when Tested with Palmitic Acid

Top engineered alpha-dioxygenase enzymes tested with palmitic acid and liquid detergent composition (final concentration of 0.12 wt %) with 15 dH hard water measured by Test Method 3 are shown in TABLE 2.

TABLE 2

Total activity improvement by different alpha-dioxygenases when tested with palmitic acid in liquid detergent and 15 dH hard water as measured by Test Method 3

| Sample | SEQ ID | Activity improvement |
|---|---|---|
| Comparative | 3 | 1.0 |
| G200D | 11 | 9.4 |
| T344S | 17 | 6.7 |
| S508D | 20 | 5.4 |
| S72P_G74P | 21 | 10.1 |
| G74P_D399G_A400P | 23 | 6.9 |

Example 3—Top Performing Enzymes when Tested with a Mixture of Fatty Acids

Top engineered alpha-dioxygenase enzymes tested with a mixture of palmitic, linoleic, stearic and oleic acid in liquid detergent composition (final concentration of 0.12 wt %) measured by Test Method 3 are shown in TABLE 3.

TABLE 3

Total aldehyde production and activity improvement by different alpha-dioxygenases as measured by Test Method 3

| Sample | SEQ ID | Total aldehyde produced | Activity improvement |
|---|---|---|---|
| Comparative | 3 | 58.4 | 1.0 |
| M329L | 15 | 118.2 | 2.0 |
| M160I | 9 | 82.1 | 1.4 |
| V156I/M160T | 22 | 94.3 | 1.6 |
| G200D | 11 | 170.0 | 2.9 |
| K248T | 14 | 163.2 | 2.8 |
| T344N | 16 | 140.9 | 2.4 |
| G74P | 6 | 177.1 | 3.0 |
| D117K | 7 | 109.0 | 1.9 |
| K248S | 13 | 83.7 | 1.4 |
| R225V | 12 | 125.1 | 2.1 |

Example 4—Suds Mileage Performance of Alpha-Dioxygenases

The suds-mileage results of alpha-dioxygenases determined by Test method 2 summarized in Table 4.

TABLE 4

Suds Mileage Index of Different Alpha-Dioxygenases at 1.2 ppm.

| Sample | SEQ ID | Suds Mileage Index |
|---|---|---|
| Comparative | 3 | 125 ± 4 |
| T344S | 17 | 129 ± 0 |
| S72P_G74P | 21 | 140 ± 9 |
| S508D | 20 | 129 ± 0 |
| G74P_D399G_A400P | 23 | 129 ± 0 |

Example 5—Exemplary Manual Dish-Washing Detergent Compositions

Manual dish-washing detergent compositions comprising engineered fatty acids alpha-dioxygenases according to the invention are shown in TABLE 5. The enzymes can be produced following the protocols described in Example 1 or similar procedures described in the art.

TABLE 5

Detergent Compositions

| Ingredient | Wt % | Wt % |
|---|---|---|
| Sodium alkyl ethoxy sulfate (C1213EO0.6S) | 22.91% | 22.91% |
| n-C12-14 Di Methyl Amine Oxide | 7.64% | 7.64% |
| Lutensol ® XP80 (non-ionic surfactant supplied by BASF) | 0.45% | 0.45% |
| Sodium Chloride | 1.2% | 1.2% |
| Poly Propylene Glycol (MW 2000) | 1% | 1% |
| Ethanol | 2% | 2% |
| Sodium Hydroxide | 0.24% | 0.24% |
| Engineered fatty acid αDOX | 0.1% | 0.0% |
| Minors (perfume, preservative, dye) + water | To 100% | To 100% |
| pH (@ 10% solution) | 9 | 9 |

Example 6—Automatic Dishwashing Compositions

The following, as shown in TABLE 5, are non-limited examples of cleaning compositions of the present invention in the form of automatic dishwashing compositions. The amounts of the ingredients are listed as weight percentage.

TABLE 6

| Ingredients | Sample 1 | Sample 2 | Sample 3 | Sample 4 | Sample 5 |
|---|---|---|---|---|---|
| Sodium carbonate | 8.0 | 7.4 | 4.0 | 3.5 | 0 |
| Sodium sulphate | 5.0 | 2.8 | 1 | 5.0 | 5.0 |
| Sodium silicate | 0.2 | 0.2 | 0 | 0.1 | 0.3 |
| MGDA | 1.5 | 2.5 | 5.0 | 2.5 | 5.0 |
| Sodium percarbonate | 1.0 | 1.0 | 2.0 | 1.0 | 2.0 |
| Sulfonated polymer | 0.25 | 0.4 | 1.2 | 0.5 | 0.5 |
| Protease | 0.025 | 0.035 | 0.035 | 0.25 | 0.035 |
| Amylase | 0.0017 | 0.0055 | 0.009 | 0.005 | 0.002 |
| Engineered fatty acid αDOX | 0.1 | 0.1 | 0.1 | 0.1 | 0.001 |
| Bleach Activator | 0.001 | 0.001 | 0.002 | 0.002 | 0.002 |
| SLF180 | 0.5 | 0.5 | 0.75 | 0.5 | 0.75 |
| Lutensol TO7 | 0.5 | 0.5 | 0.9 | 0.9 | 0.5 |
| Liquid polymer | 0.5 | 0.5 | 0 | 0.5 | 0 |
| Miscellaneous | balance to 18 g | balance to 18 g | balance to 18 g | balance to 18 g | balance to 18 g |

Wherein values in the table above are given as gram of active material.

| | |
|---|---|
| Amylase | Stainzyme plus ® supplied by Novozymes |
| Bleach Activator | PAAN by Weylchem |
| Lutensol TO7 | Nonionic surfactant supplied by BASF |
| Liquid polymer | GT 101 supplied by Nippon Shokubi |
| MGDA | Three-sodium Methyl glycine diacetate supplied by BASF |

-continued

| | |
|---|---|
| Protease | Ultimase ® supplied by DuPont |
| Sulfonated polymer | Acusol 588 supplied by Dow Chemicals |
| SLF180 | Nonionic surfactant supplied by BASF |

Example 7—Shampoo Compositions

The following, as shown in TABLES 6 and 7, are non-limited examples of cleaning compositions of the present invention in the form of shampoo compositions for cleaning hair. The amounts of the ingredients are listed as weight percentage.

TABLE 7

| Ingredients | Sample 6 | Sample 7 |
|---|---|---|
| Water Purified | Q.S to 100 | Q.S to 100 |
| Sodium Laureth-3 Sulfate | 21.6 | 21.6 |
| Sodium Lauryl Sulfate | 34.5 | 34.5 |
| Laureth-4 | 0.9 | 0.9 |
| Dimethicone 330M cps | 0.5 | 0.5 |
| Glycol Distearate | 1.5 | 1.5 |
| Polyquaternium-6 | 0.32 | 0.32 |
| Engineered fatty acid αDOX | 0.1 | 0.001 |
| Sodium Benzoate | 0.27 | 0.27 |
| Citric acid 50% Solution | 0.52 | 0.52 |
| Methylchloroisothiazolinone/methylisothiazolinone | 0.035 | 0.035 |
| Sodium chloride | 1.66 | 1.66 |
| Fragrance | 0.65 | 0.65 |
| DL-Panthenol 56% solution | 0.05 | 0.05 |
| Panthenyl Ethyl ether | 0.03 | 0.03 |

TABLE 8

| Ingredient | Sample 8 | Sample 9 | Sample 10 | Sample 11 | Sample 12 | Sample 13 | Sample 14 |
|---|---|---|---|---|---|---|---|
| Sodium lauryl ether sulfate (SLE3S) | | 6 | 10 | 6 | 6 | 9 | |
| Sodium cocoyl isethionate | | | | | | | 8.5 |
| Sodium lauryl sulfate (SLS) | 1.5 | 7 | 1.5 | 7 | 7 | 6 | |
| Sodium lauryl ether sulfate (SLE1S) | 10.5 | | | | | | |
| Disodium laureth sulfosuccinate | | | | | | | 8.5 |
| Sodium lauryl sulfoacetate | | | | | | | 2.5 |
| Sodium Lauroyl Sarcosinate | | | | | | | 0.75 |
| Cocoamidopropyl Hydroxysultaine | | | | | | | 1.5 |
| Cocoamidopropyl Betaine | 1 | 2 | 2 | 2 | 2 | 2 | 2 |
| Coconut monoethanol amide (CMEA) | | 0.85 | | 0.85 | | | |
| Cetyl alcohol | | | 1 | | | | |
| Stearyl alcohol | | | 2 | | | | |
| Dimethicone | 1 | 1 | 1 | 1 | 1 | | 0.5 |
| Ethylene glycol distearate (EGDS) | 1.5 | 1.5 | 1.5 | 1.5 | 1.5 | | |
| Jaguar ® C500[1] | 0.25 | 0.25 | 0.15 | | | | |
| Synthetic Cationic Polymer AMT[2] | | | | 0.1 | | | |
| Polydiallyldimethylammonium chloride (DADMAC) | | | | | 0.1 | | |
| Engineered fatty acid αDOX | 0.01 | 0.1 | 0.001 | 0.01 | 0.001 | 0.1 | 0.01 |
| Excel Guar[3] | | | | | | 0.1 | .15 |
| pH | 6 | 6 | 6 | 6 | 6 | 6 | |
| Water-USP Purified & Minors | Q.S. to 100 | Q.S. to 100 | Q.S. to 100 | Q.S. to 100 | Q.S. to 100 | Q.S. to 100 | Q.S. to 100 |

[1]Cationic polymer derived from a natural gum with low aqueous viscosity

[2]Cationic synthetic copolymer

[3]Cationic plant derived polymer

All percentages and ratios given for enzymes are based on active protein. All percentages and ratios herein are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

What is claimed is:

1. An engineered fatty acid alpha-dioxygenase comprising:

a polypeptide sequence having at least about 98% identity to SEQ ID NO: 1; wherein said polypeptide sequence comprises at least one amino acid substitution of: G74P (SEQ ID NO: 6), G200D (SEQ ID NO: 11), K248T (SEQ ID NO: 14), T344N (SEQ ID NO: 16), or mixtures thereof; wherein said positions are numbered with reference to SEQ ID NO: 1; and wherein said engineered fatty acid alpha-dioxygenase catalyzes the conversion a fatty acid that is at least one of: stearic acid, oleic acid, linoleic acid, linolenic acid, or mixtures thereof.

2. The engineered fatty acid alpha-dioxygenase of claim 1, wherein said polypeptide sequence comprises at least one amino acid substitution of: S72P/G74P (SEQ ID NO: 21), wherein said positions are numbered with reference to SEQ ID NO: 1.

3. A cleaning composition comprising at least one engineered fatty acid alpha-dioxygenase of claim 1.

4. A cleaning composition according to claim 3, further comprising one or more co-enzymes that are at least one of: fatty-acid peroxidases (EC 1.11.1.3), unspecific peroxygenases (EC 1.11.2.1), plant seed peroxygenases (EC 1.11.2.3), fatty acid peroxygenases (EC1.11.2.4), linoleate diol synthases (EC 1.13.11.44), 5,8-linoleate diol synthases (EC 1.13.11.60 and EC 5.4.4.5), 7,8-linoleate diol synthases (EC 1.13.11.60 and EC 5.4.4.6), 9,14-linoleate diol synthases (EC 1.13.11.B1), 8,11-linoleate diol synthases, oleate diol synthases, other linoleate diol synthases, unspecific monooxygenase (EC 1.14.14.1), alkane 1-monooxygenase (EC 1.14.15.3), oleate 12-hydroxylases (EC 1.14.18.4), fatty acid amide hydrolases (EC 3.5.1.99), fatty acid photodecarboxylases (EC 4.1.1.106), oleate hydratases (EC 4.2.1.53), linoleate isomerases (EC 5.2.1.5), linoleate (10E,12Z)-isomerases (EC 5.3.3.B2), P450 fatty acid decarboxylases (OleT-like), non-heme fatty acid decarboxylases (UndA-like), amylases, lipases, proteases, cellulases, and mixtures thereof.

5. A cleaning composition according to claim 3, wherein said one or more engineered fatty acid alpha-dioxygenases are present in an amount of from 0.0001 wt % to 1 wt %, by weight of the cleaning composition, based on active protein.

6. The cleaning composition according to claim 3, further comprising a surfactant.

7. The cleaning composition of claim 6, wherein the surfactant is present in an amount of from 1 wt % to 60 wt %, by weight of the cleaning composition.

8. The cleaning composition of claim 6, wherein said surfactant is at least one of anionic surfactants, nonionic surfactants, zwitterionic surfactants, amphoteric surfactants, cationic surfactants, and mixtures thereof.

9. A method for converting a fatty acid to a material that is at least one of: 2-hydroperoxy fatty acids, 2-hydroperoxy fatty acid derivatives, and mixtures thereof, comprising the steps of contacting at least: a) one or more fatty acids, b) oxygen, and c) one or more engineered fatty acid alpha-dioxygenase of claim 1; wherein said contacting step is performed under conditions such that said fatty acid is transformed by said engineered fatty acid alpha-dioxygenase to provide said material; and wherein said fatty acid is selected from the group consisting of stearic acid, oleic acid, linoleic acid, linolenic acid, or mixtures thereof.

10. A method of producing 2-hydroperoxy fatty acids, 2-hydroperoxy fatty acid Derivatives, or mixtures thereof; wherein said method comprises: a) contacting a host cell expressing one or more engineered fatty acid alpha-dioxygenases of claim 1 with one or more fatty acids, and b) culturing the host cell under conditions such that said one or more engineered fatty acid alpha-dioxygenases catalyze the conversion of said one or more fatty acids to one or more materials that are at least one of 2-hydroperoxy fatty acids, 2-hydroperoxy fatty acid derivatives, or mixtures thereof.

* * * * *

```
                         SEQUENCE LISTING

<160> NUMBER OF SEQ ID NOS: 24

<210> SEQ ID NO 1
<211> LENGTH: 618
<212> TYPE: PRT
<213> ORGANISM: Oryza sativa

<400> SEQUENCE: 1

Met Gly Ser Gly Leu Phe Lys Pro Arg Val His Pro Asp Leu Arg Asp
1               5                   10                  15

Val Phe Ser Lys Met Ser Phe Phe Asp Lys Ile Gly Phe Leu Phe Ile
            20                  25                  30

His Ala Phe Asp Lys Arg Asn Leu Trp His Lys Val Pro Val Pro Ile
        35                  40                  45

Gly Leu Leu Tyr Leu Asn Thr Arg Arg Thr Leu Leu Glu Lys Tyr Asn
    50                  55                  60

Leu Leu Ala Val Gly Arg Ser Ser His Gly Ala Leu Phe Asp Pro Lys
65                  70                  75                  80

Glu Phe Leu Tyr Arg Thr Glu Asp Gly Lys Tyr Asn Asp Pro His Asn
                85                  90                  95

Ala Glu Ala Gly Ser Gln Asn Thr Phe Phe Gly Arg Asn Met Glu Pro
            100                 105                 110

Val Asp Gln Gln Asp Glu Leu Met Ser Pro Asp Pro Phe Val Val Ala
        115                 120                 125

Thr Lys Leu Leu Ala Arg Arg Glu Tyr Lys Asp Thr Gly Lys Gln Phe
    130                 135                 140

Asn Ile Leu Ala Ala Ala Trp Ile Gln Phe Met Val His Asp Trp Met
145                 150                 155                 160

Asp His Met Glu Asp Thr Gly Gln Ile Gly Ile Thr Ala Pro Lys Glu
                165                 170                 175

Val Ala Asn Glu Cys Pro Leu Lys Ser Phe Lys Phe His Pro Thr Lys
            180                 185                 190

Glu Leu Pro Thr Asn Ser Asp Gly Ile Lys Ile Gly His Tyr Asn Ile
        195                 200                 205

Arg Thr Ala Trp Trp Asp Gly Ser Ala Val Tyr Gly Asn Asn Glu Glu
    210                 215                 220

Arg Ala Glu Lys Leu Arg Thr Tyr Val Asp Gly Lys Leu Val Ile Gly
225                 230                 235                 240

Asp Asp Gly Leu Leu Leu His Lys Glu Asn Gly Val Ala Leu Ser Gly
                245                 250                 255

Asp Ile Arg Asn Ser Trp Ala Gly Val Ser Ile Leu Gln Ala Leu Phe
            260                 265                 270

Val Lys Glu His Asn Ala Val Cys Asp Ala Ile Lys Glu Glu His Pro
        275                 280                 285
```

-continued

```
Asn Leu Ser Asp Glu Glu Leu Tyr Arg Tyr Ala Lys Leu Val Thr Ser
    290                 295                 300

Ala Val Ile Ala Lys Val His Thr Ile Asp Trp Thr Val Glu Leu Leu
305                 310                 315                 320

Lys Thr Lys Thr Met Arg Ala Ala Met Arg Ala Asn Trp Tyr Gly Leu
                325                 330                 335

Leu Gly Lys Lys Ile Lys Asp Thr Phe Gly His Ile Gly Gly Pro Ile
            340                 345                 350

Leu Gly Gly Leu Val Gly Leu Lys Lys Pro Asn Asn His Gly Val Pro
        355                 360                 365

Tyr Ser Leu Thr Glu Glu Phe Thr Ser Val Tyr Arg Met His Ser Leu
    370                 375                 380

Ile Pro Ser Thr Leu Lys Leu Arg Asp Pro Thr Gly Gln Pro Asp Ala
385                 390                 395                 400

Asn Asn Ser Pro Pro Cys Leu Glu Asp Ile Asp Ile Gly Glu Met Ile
                405                 410                 415

Gly Leu Lys Gly Glu Glu Gln Leu Ser Lys Ile Gly Phe Glu Lys Gln
            420                 425                 430

Ala Leu Ser Met Gly Tyr Gln Ala Cys Gly Ala Leu Glu Leu Trp Asn
        435                 440                 445

Tyr Pro Ser Phe Phe Arg Asn Leu Ile Pro Gln Asn Leu Asp Gly Thr
    450                 455                 460

Asn Arg Ser Asp Arg Ile Asp Leu Ala Ala Leu Glu Val Tyr Arg Asp
465                 470                 475                 480

Arg Glu Arg Ser Val Pro Arg Tyr Asn Glu Phe Arg Arg Arg Leu Phe
                485                 490                 495

Leu Ile Pro Ile Lys Ser Trp Glu Asp Leu Thr Ser Asp Lys Asp Ala
            500                 505                 510

Ile Glu Thr Ile Arg Ala Ile Tyr Gly Asp Asp Val Glu Lys Leu Asp
        515                 520                 525

Leu Leu Val Gly Leu Met Ala Glu Lys Lys Ile Lys Gly Phe Ala Ile
    530                 535                 540

Ser Glu Thr Ala Phe Asn Ile Phe Ile Leu Met Ala Ser Arg Arg Leu
545                 550                 555                 560

Glu Ala Asp Arg Phe Phe Thr Ser Asn Phe Asn Glu Glu Thr Tyr Thr
                565                 570                 575

Lys Lys Gly Met Gln Trp Val Lys Thr Thr Glu Gly Leu Arg Asp Val
            580                 585                 590

Ile Asn Arg His Tyr Pro Glu Ile Thr Ala Lys Trp Met Lys Ser Ser
        595                 600                 605

Ser Ala Phe Ser Val Trp Asp Ala Asp Tyr
    610                 615
```

<210> SEQ ID NO 2
<211> LENGTH: 1890
<212> TYPE: DNA
<213> ORGANISM: Artificial Sequence
<220> FEATURE:
<223> OTHER INFORMATION: Codon optimized DNA sequence

<400> SEQUENCE: 2

```
catatgcacc accaccacca ccacatggga tcagggctat ttaaacccag ggttcacccg     60

gacctgcgtg atgtgtttag caagatgagc ttctttgaca aaattggttt cctgtttatc    120

cacgcgttcg ataagcgtaa cctgtggcac aaagtgccgg ttccgatcgg cctgctgtac    180
```

-continued

```
ctgaacaccc gtcgtaccct gctggagaaa tataacctgc tggcggttgg tcgtagcagc    240

catggtgcgc tgtttgaccc gaaggagttt ctgtaccgta ccgaagacgg taaatataac    300

gatccgcaca acgcggaagc gggtagccag aacaccttct ttggccgtaa catggagccg    360

gtggaccagc aagatgaact gatgagcccg gacccgtttg tggttgcgac caagctgctg    420

gcgcgtcgtg agtataagga taccggtaaa cagttcaaca ttctggcggc ggcgtggatc    480

caatttatgg ttcacgactg gatggatcac atggaagaca ccggtcaaat cggcattacc    540

gcgccgaaag aggtggcgaa cgaatgcccg ctgaagagct tcaaatttca cccgaccaag    600

gagctgccga ccaacagcga cggtatcaaa attggccact acaacattcg taccgcgtgg    660

tgggatggta gcgcggttta tggcaacaac gaggaacgtg cggagaagct gcgtacctac    720

gttgacggta aactggtgat cggtgacgat ggcctgctgc tgcacaagga aaacggtgtt    780

gcgctgagcg gcgatattcg taacagctgg gcgggcgtga gcatcctgca ggcgctgttc    840

gttaaggagc acaacgcggt gtgcgacgcg atcaaagagg aacacccgaa cctgagcgat    900

gaggaactgt accgttatgc gaagctggtg accagcgcgg ttattgcgaa agtgcacacc    960

atcgactgga ccgttgaact gctgaagacc aaaaccatgc gtgcggcgat gcgtgcgaac   1020

tggtacggtc tgctgggcaa gaaaattaaa gataccttcg gtcacattgg tggcccgatc   1080

ctgggtggcc tggttggtct gaagaaaccg aacaaccacg gcgtgccgta cagcctgacc   1140

gaggaattta ccagcgtgta tcgtatgcac agcctgatcc cgagcaccct gaagctgcgt   1200

gacccgaccg gtcagccgga tgcgaacaac agcccgccgt gcctggagga catcgatatt   1260

ggtgaaatga ttggtctgaa aggcgaggaa caactgagca agatcggctt cgagaaacag   1320

gcgctgagca tgggttacca agcgtgcggc gcgctggaac tgtggaacta tccgagcttc   1380

tttcgtaacc tgattccgca gaacctggac ggtaccaacc gtagcgaccg tatcgatctg   1440

gcggcgctgg aagtgtaccg tgatcgtgaa cgtagcgtgc cgcgttataa cgagttccgt   1500

cgtcgtctgt tcctgatccc gattaagagc tgggaggacc tgaccagcga caaagatgcg   1560

atcgaaacca ttcgtgcgat ctatggtgac gatgttgaaa agctggacct gctggttggt   1620

ctgatggcgg agaagaaaat taaaggcttc gcgatcagcg aaaccgcgtt caacatcttt   1680

attctgatgg cgagccgtcg tctggaagcg gaccgtttct ttaccagcaa ctttaacgag   1740

gaaacctaca ccaagaaagg tatgcaatgg gttaagacca ccgagggcct gcgtgatgtg   1800

attaaccgtc actatccgga aatcaccgcg aagtggatga aagcagcag cgcgttcagc   1860

gtgtgggatg cggattacta atgaaagctt                                    1890
```

<210> SEQ ID NO 3
<211> LENGTH: 625
<212> TYPE: PRT
<213> ORGANISM: Oryza sativa

<400> SEQUENCE: 3

```
Met His His His His His His Met Gly Ser Gly Leu Phe Lys Pro Arg
1               5                   10                  15

Val His Pro Asp Leu Arg Asp Val Phe Ser Lys Met Ser Phe Phe Asp
            20                  25                  30

Lys Ile Gly Phe Leu Phe Ile His Ala Phe Asp Lys Arg Asn Leu Trp
        35                  40                  45

His Lys Val Pro Val Pro Ile Gly Leu Leu Tyr Leu Asn Thr Arg Arg
    50                  55                  60
```

-continued

```
Thr Leu Leu Glu Lys Tyr Asn Leu Leu Ala Val Gly Arg Ser Ser His
65                  70                  75                  80

Gly Ala Leu Phe Asp Pro Lys Glu Phe Leu Tyr Arg Thr Glu Asp Gly
                85                  90                  95

Lys Tyr Asn Asp Pro His Asn Ala Glu Ala Gly Ser Gln Asn Thr Phe
            100                 105                 110

Phe Gly Arg Asn Met Glu Pro Val Asp Gln Gln Asp Glu Leu Met Ser
        115                 120                 125

Pro Asp Pro Phe Val Val Ala Thr Lys Leu Leu Ala Arg Arg Glu Tyr
    130                 135                 140

Lys Asp Thr Gly Lys Gln Phe Asn Ile Leu Ala Ala Ala Trp Ile Gln
145                 150                 155                 160

Phe Met Val His Asp Trp Met Asp His Met Glu Asp Thr Gly Gln Ile
                165                 170                 175

Gly Ile Thr Ala Pro Lys Glu Val Ala Asn Glu Cys Pro Leu Lys Ser
            180                 185                 190

Phe Lys Phe His Pro Thr Lys Glu Leu Pro Thr Asn Ser Asp Gly Ile
        195                 200                 205

Lys Ile Gly His Tyr Asn Ile Arg Thr Ala Trp Trp Asp Gly Ser Ala
    210                 215                 220

Val Tyr Gly Asn Asn Glu Glu Arg Ala Glu Lys Leu Arg Thr Tyr Val
225                 230                 235                 240

Asp Gly Lys Leu Val Ile Gly Asp Asp Gly Leu Leu Leu His Lys Glu
                245                 250                 255

Asn Gly Val Ala Leu Ser Gly Asp Ile Arg Asn Ser Trp Ala Gly Val
            260                 265                 270

Ser Ile Leu Gln Ala Leu Phe Val Lys Glu His Asn Ala Val Cys Asp
        275                 280                 285

Ala Ile Lys Glu Glu His Pro Asn Leu Ser Asp Glu Glu Leu Tyr Arg
    290                 295                 300

Tyr Ala Lys Leu Val Thr Ser Ala Val Ile Ala Lys Val His Thr Ile
305                 310                 315                 320

Asp Trp Thr Val Glu Leu Leu Lys Thr Lys Thr Met Arg Ala Ala Met
                325                 330                 335

Arg Ala Asn Trp Tyr Gly Leu Leu Gly Lys Lys Ile Lys Asp Thr Phe
            340                 345                 350

Gly His Ile Gly Gly Pro Ile Leu Gly Gly Leu Val Gly Leu Lys Lys
        355                 360                 365

Pro Asn Asn His Gly Val Pro Tyr Ser Leu Thr Glu Glu Phe Thr Ser
    370                 375                 380

Val Tyr Arg Met His Ser Leu Ile Pro Ser Thr Leu Lys Leu Arg Asp
385                 390                 395                 400

Pro Thr Gly Gln Pro Asp Ala Asn Asn Ser Pro Pro Cys Leu Glu Asp
                405                 410                 415

Ile Asp Ile Gly Glu Met Ile Gly Leu Lys Gly Glu Glu Gln Leu Ser
            420                 425                 430

Lys Ile Gly Phe Glu Lys Gln Ala Leu Ser Met Gly Tyr Gln Ala Cys
        435                 440                 445

Gly Ala Leu Glu Leu Trp Asn Tyr Pro Ser Phe Phe Arg Asn Leu Ile
    450                 455                 460

Pro Gln Asn Leu Asp Gly Thr Asn Arg Ser Asp Arg Ile Asp Leu Ala
465                 470                 475                 480

Ala Leu Glu Val Tyr Arg Asp Arg Glu Arg Ser Val Pro Arg Tyr Asn
```

-continued

```
                485                 490                 495

Glu Phe Arg Arg Arg Leu Phe Leu Ile Pro Ile Lys Ser Trp Glu Asp
            500                 505                 510

Leu Thr Ser Asp Lys Asp Ala Ile Glu Thr Ile Arg Ala Ile Tyr Gly
        515                 520                 525

Asp Asp Val Glu Lys Leu Asp Leu Leu Val Gly Leu Met Ala Glu Lys
    530                 535                 540

Lys Ile Lys Gly Phe Ala Ile Ser Glu Thr Ala Phe Asn Ile Phe Ile
545                 550                 555                 560

Leu Met Ala Ser Arg Arg Leu Glu Ala Asp Arg Phe Phe Thr Ser Asn
                565                 570                 575

Phe Asn Glu Glu Thr Tyr Thr Lys Lys Gly Met Gln Trp Val Lys Thr
            580                 585                 590

Thr Glu Gly Leu Arg Asp Val Ile Asn Arg His Tyr Pro Glu Ile Thr
        595                 600                 605

Ala Lys Trp Met Lys Ser Ser Ser Ala Phe Ser Val Trp Asp Ala Asp
    610                 615                 620

Tyr
625


<210> SEQ ID NO 4
<211> LENGTH: 618
<212> TYPE: PRT
<213> ORGANISM: Artificial Sequence
<220> FEATURE:
<223> OTHER INFORMATION: N54V substitution

<400> SEQUENCE: 4

Met Gly Ser Gly Leu Phe Lys Pro Arg Val His Pro Asp Leu Arg Asp
1               5                   10                  15

Val Phe Ser Lys Met Ser Phe Phe Asp Lys Ile Gly Phe Leu Phe Ile
            20                  25                  30

His Ala Phe Asp Lys Arg Asn Leu Trp His Lys Val Pro Val Pro Ile
        35                  40                  45

Gly Leu Leu Tyr Leu Val Thr Arg Arg Thr Leu Leu Glu Lys Tyr Asn
    50                  55                  60

Leu Leu Ala Val Gly Arg Ser Ser His Gly Ala Leu Phe Asp Pro Lys
65                  70                  75                  80

Glu Phe Leu Tyr Arg Thr Glu Asp Gly Lys Tyr Asn Asp Pro His Asn
                85                  90                  95

Ala Glu Ala Gly Ser Gln Asn Thr Phe Phe Gly Arg Asn Met Glu Pro
            100                 105                 110

Val Asp Gln Gln Asp Glu Leu Met Ser Pro Asp Pro Phe Val Val Ala
        115                 120                 125

Thr Lys Leu Leu Ala Arg Arg Glu Tyr Lys Asp Thr Gly Lys Gln Phe
    130                 135                 140

Asn Ile Leu Ala Ala Ala Trp Ile Gln Phe Met Val His Asp Trp Met
145                 150                 155                 160

Asp His Met Glu Asp Thr Gly Gln Ile Gly Ile Thr Ala Pro Lys Glu
                165                 170                 175

Val Ala Asn Glu Cys Pro Leu Lys Ser Phe Lys Phe His Pro Thr Lys
            180                 185                 190

Glu Leu Pro Thr Asn Ser Asp Gly Ile Lys Ile Gly His Tyr Asn Ile
        195                 200                 205

Arg Thr Ala Trp Trp Asp Gly Ser Ala Val Tyr Gly Asn Asn Glu Glu
```

-continued

```
    210                 215                 220

Arg Ala Glu Lys Leu Arg Thr Tyr Val Asp Gly Lys Leu Val Ile Gly
225                 230                 235                 240

Asp Asp Gly Leu Leu Leu His Lys Glu Asn Gly Val Ala Leu Ser Gly
                245                 250                 255

Asp Ile Arg Asn Ser Trp Ala Gly Val Ser Ile Leu Gln Ala Leu Phe
            260                 265                 270

Val Lys Glu His Asn Ala Val Cys Asp Ala Ile Lys Glu Glu His Pro
        275                 280                 285

Asn Leu Ser Asp Glu Glu Leu Tyr Arg Tyr Ala Lys Leu Val Thr Ser
    290                 295                 300

Ala Val Ile Ala Lys Val His Thr Ile Asp Trp Thr Val Glu Leu Leu
305                 310                 315                 320

Lys Thr Lys Thr Met Arg Ala Ala Met Arg Ala Asn Trp Tyr Gly Leu
                325                 330                 335

Leu Gly Lys Lys Ile Lys Asp Thr Phe Gly His Ile Gly Gly Pro Ile
            340                 345                 350

Leu Gly Gly Leu Val Gly Leu Lys Lys Pro Asn Asn His Gly Val Pro
        355                 360                 365

Tyr Ser Leu Thr Glu Glu Phe Thr Ser Val Tyr Arg Met His Ser Leu
    370                 375                 380

Ile Pro Ser Thr Leu Lys Leu Arg Asp Pro Thr Gly Gln Pro Asp Ala
385                 390                 395                 400

Asn Asn Ser Pro Pro Cys Leu Glu Asp Ile Asp Ile Gly Glu Met Ile
                405                 410                 415

Gly Leu Lys Gly Glu Glu Gln Leu Ser Lys Ile Gly Phe Glu Lys Gln
            420                 425                 430

Ala Leu Ser Met Gly Tyr Gln Ala Cys Gly Ala Leu Glu Leu Trp Asn
        435                 440                 445

Tyr Pro Ser Phe Phe Arg Asn Leu Ile Pro Gln Asn Leu Asp Gly Thr
    450                 455                 460

Asn Arg Ser Asp Arg Ile Asp Leu Ala Ala Leu Glu Val Tyr Arg Asp
465                 470                 475                 480

Arg Glu Arg Ser Val Pro Arg Tyr Asn Glu Phe Arg Arg Arg Leu Phe
                485                 490                 495

Leu Ile Pro Ile Lys Ser Trp Glu Asp Leu Thr Ser Asp Lys Asp Ala
            500                 505                 510

Ile Glu Thr Ile Arg Ala Ile Tyr Gly Asp Asp Val Glu Lys Leu Asp
        515                 520                 525

Leu Leu Val Gly Leu Met Ala Glu Lys Lys Ile Lys Gly Phe Ala Ile
    530                 535                 540

Ser Glu Thr Ala Phe Asn Ile Phe Ile Leu Met Ala Ser Arg Arg Leu
545                 550                 555                 560

Glu Ala Asp Arg Phe Phe Thr Ser Asn Phe Asn Glu Glu Thr Tyr Thr
                565                 570                 575

Lys Lys Gly Met Gln Trp Val Lys Thr Thr Glu Gly Leu Arg Asp Val
            580                 585                 590

Ile Asn Arg His Tyr Pro Glu Ile Thr Ala Lys Trp Met Lys Ser Ser
        595                 600                 605

Ser Ala Phe Ser Val Trp Asp Ala Asp Tyr
    610                 615
```

<210> SEQ ID NO 5

-continued

<211> LENGTH: 618
<212> TYPE: PRT
<213> ORGANISM: Artificial Sequence
<220> FEATURE:
<223> OTHER INFORMATION: S72P substitution

<400> SEQUENCE: 5

```
Met Gly Ser Gly Leu Phe Lys Pro Arg Val His Pro Asp Leu Arg Asp
1               5                   10                  15

Val Phe Ser Lys Met Ser Phe Phe Asp Lys Ile Gly Phe Leu Phe Ile
            20                  25                  30

His Ala Phe Asp Lys Arg Asn Leu Trp His Lys Val Pro Val Pro Ile
        35                  40                  45

Gly Leu Leu Tyr Leu Asn Thr Arg Arg Thr Leu Leu Glu Lys Tyr Asn
    50                  55                  60

Leu Leu Ala Val Gly Arg Ser Pro His Gly Ala Leu Phe Asp Pro Lys
65                  70                  75                  80

Glu Phe Leu Tyr Arg Thr Glu Asp Gly Lys Tyr Asn Asp Pro His Asn
                85                  90                  95

Ala Glu Ala Gly Ser Gln Asn Thr Phe Phe Gly Arg Asn Met Glu Pro
            100                 105                 110

Val Asp Gln Gln Asp Glu Leu Met Ser Pro Asp Pro Phe Val Val Ala
        115                 120                 125

Thr Lys Leu Leu Ala Arg Arg Glu Tyr Lys Asp Thr Gly Lys Gln Phe
    130                 135                 140

Asn Ile Leu Ala Ala Ala Trp Ile Gln Phe Met Val His Asp Trp Met
145                 150                 155                 160

Asp His Met Glu Asp Thr Gly Gln Ile Gly Ile Thr Ala Pro Lys Glu
                165                 170                 175

Val Ala Asn Glu Cys Pro Leu Lys Ser Phe Lys Phe His Pro Thr Lys
            180                 185                 190

Glu Leu Pro Thr Asn Ser Asp Gly Ile Lys Ile Gly His Tyr Asn Ile
        195                 200                 205

Arg Thr Ala Trp Trp Asp Gly Ser Ala Val Tyr Gly Asn Asn Glu Glu
    210                 215                 220

Arg Ala Glu Lys Leu Arg Thr Tyr Val Asp Gly Lys Leu Val Ile Gly
225                 230                 235                 240

Asp Asp Gly Leu Leu Leu His Lys Glu Asn Gly Val Ala Leu Ser Gly
                245                 250                 255

Asp Ile Arg Asn Ser Trp Ala Gly Val Ser Ile Leu Gln Ala Leu Phe
            260                 265                 270

Val Lys Glu His Asn Ala Val Cys Asp Ala Ile Lys Glu Glu His Pro
        275                 280                 285

Asn Leu Ser Asp Glu Glu Leu Tyr Arg Tyr Ala Lys Leu Val Thr Ser
    290                 295                 300

Ala Val Ile Ala Lys Val His Thr Ile Asp Trp Thr Val Glu Leu Leu
305                 310                 315                 320

Lys Thr Lys Thr Met Arg Ala Ala Met Arg Ala Asn Trp Tyr Gly Leu
                325                 330                 335

Leu Gly Lys Lys Ile Lys Asp Thr Phe Gly His Ile Gly Gly Pro Ile
            340                 345                 350

Leu Gly Gly Leu Val Gly Leu Lys Lys Pro Asn Asn His Gly Val Pro
        355                 360                 365

Tyr Ser Leu Thr Glu Glu Phe Thr Ser Val Tyr Arg Met His Ser Leu
    370                 375                 380
```

Ile Pro Ser Thr Leu Lys Leu Arg Asp Pro Thr Gly Gln Pro Asp Ala
385 390 395 400

Asn Asn Ser Pro Pro Cys Leu Glu Asp Ile Asp Ile Gly Glu Met Ile
405 410 415

Gly Leu Lys Gly Glu Glu Gln Leu Ser Lys Ile Gly Phe Glu Lys Gln
420 425 430

Ala Leu Ser Met Gly Tyr Gln Ala Cys Gly Ala Leu Glu Leu Trp Asn
435 440 445

Tyr Pro Ser Phe Phe Arg Asn Leu Ile Pro Gln Asn Leu Asp Gly Thr
450 455 460

Asn Arg Ser Asp Arg Ile Asp Leu Ala Ala Leu Glu Val Tyr Arg Asp
465 470 475 480

Arg Glu Arg Ser Val Pro Arg Tyr Asn Glu Phe Arg Arg Arg Leu Phe
485 490 495

Leu Ile Pro Ile Lys Ser Trp Glu Asp Leu Thr Ser Asp Lys Asp Ala
500 505 510

Ile Glu Thr Ile Arg Ala Ile Tyr Gly Asp Asp Val Glu Lys Leu Asp
515 520 525

Leu Leu Val Gly Leu Met Ala Glu Lys Lys Ile Lys Gly Phe Ala Ile
530 535 540

Ser Glu Thr Ala Phe Asn Ile Phe Ile Leu Met Ala Ser Arg Arg Leu
545 550 555 560

Glu Ala Asp Arg Phe Phe Thr Ser Asn Phe Asn Glu Glu Thr Tyr Thr
565 570 575

Lys Lys Gly Met Gln Trp Val Lys Thr Thr Glu Gly Leu Arg Asp Val
580 585 590

Ile Asn Arg His Tyr Pro Glu Ile Thr Ala Lys Trp Met Lys Ser Ser
595 600 605

Ser Ala Phe Ser Val Trp Asp Ala Asp Tyr
610 615

<210> SEQ ID NO 6
<211> LENGTH: 618
<212> TYPE: PRT
<213> ORGANISM: Artificial Sequence
<220> FEATURE:
<223> OTHER INFORMATION: G74P Substitution

<400> SEQUENCE: 6

Met Gly Ser Gly Leu Phe Lys Pro Arg Val His Pro Asp Leu Arg Asp
1 5 10 15

Val Phe Ser Lys Met Ser Phe Phe Asp Lys Ile Gly Phe Leu Phe Ile
20 25 30

His Ala Phe Asp Lys Arg Asn Leu Trp His Lys Val Pro Val Pro Ile
35 40 45

Gly Leu Leu Tyr Leu Asn Thr Arg Arg Thr Leu Leu Glu Lys Tyr Asn
50 55 60

Leu Leu Ala Val Gly Arg Ser Ser His Pro Ala Leu Phe Asp Pro Lys
65 70 75 80

Glu Phe Leu Tyr Arg Thr Glu Asp Gly Lys Tyr Asn Asp Pro His Asn
85 90 95

Ala Glu Ala Gly Ser Gln Asn Thr Phe Phe Gly Arg Asn Met Glu Pro
100 105 110

Val Asp Gln Gln Asp Glu Leu Met Ser Pro Asp Pro Phe Val Val Ala
115 120 125

-continued

```
Thr Lys Leu Leu Ala Arg Arg Glu Tyr Lys Asp Thr Gly Lys Gln Phe
    130                 135                 140

Asn Ile Leu Ala Ala Ala Trp Ile Gln Phe Met Val His Asp Trp Met
145                 150                 155                 160

Asp His Met Glu Asp Thr Gly Gln Ile Gly Ile Thr Ala Pro Lys Glu
                165                 170                 175

Val Ala Asn Glu Cys Pro Leu Lys Ser Phe Lys Phe His Pro Thr Lys
            180                 185                 190

Glu Leu Pro Thr Asn Ser Asp Gly Ile Lys Ile Gly His Tyr Asn Ile
        195                 200                 205

Arg Thr Ala Trp Trp Asp Gly Ser Ala Val Tyr Gly Asn Asn Glu Glu
    210                 215                 220

Arg Ala Glu Lys Leu Arg Thr Tyr Val Asp Gly Lys Leu Val Ile Gly
225                 230                 235                 240

Asp Asp Gly Leu Leu Leu His Lys Glu Asn Gly Val Ala Leu Ser Gly
                245                 250                 255

Asp Ile Arg Asn Ser Trp Ala Gly Val Ser Ile Leu Gln Ala Leu Phe
            260                 265                 270

Val Lys Glu His Asn Ala Val Cys Asp Ala Ile Lys Glu Glu His Pro
        275                 280                 285

Asn Leu Ser Asp Glu Glu Leu Tyr Arg Tyr Ala Lys Leu Val Thr Ser
    290                 295                 300

Ala Val Ile Ala Lys Val His Thr Ile Asp Trp Thr Val Glu Leu Leu
305                 310                 315                 320

Lys Thr Lys Thr Met Arg Ala Ala Met Arg Ala Asn Trp Tyr Gly Leu
                325                 330                 335

Leu Gly Lys Lys Ile Lys Asp Thr Phe Gly His Ile Gly Gly Pro Ile
            340                 345                 350

Leu Gly Gly Leu Val Gly Leu Lys Lys Pro Asn Asn His Gly Val Pro
        355                 360                 365

Tyr Ser Leu Thr Glu Glu Phe Thr Ser Val Tyr Arg Met His Ser Leu
    370                 375                 380

Ile Pro Ser Thr Leu Lys Leu Arg Asp Pro Thr Gly Gln Pro Asp Ala
385                 390                 395                 400

Asn Asn Ser Pro Pro Cys Leu Glu Asp Ile Asp Ile Gly Glu Met Ile
                405                 410                 415

Gly Leu Lys Gly Glu Glu Gln Leu Ser Lys Ile Gly Phe Glu Lys Gln
            420                 425                 430

Ala Leu Ser Met Gly Tyr Gln Ala Cys Gly Ala Leu Glu Leu Trp Asn
        435                 440                 445

Tyr Pro Ser Phe Phe Arg Asn Leu Ile Pro Gln Asn Leu Asp Gly Thr
    450                 455                 460

Asn Arg Ser Asp Arg Ile Asp Leu Ala Ala Leu Glu Val Tyr Arg Asp
465                 470                 475                 480

Arg Glu Arg Ser Val Pro Arg Tyr Asn Glu Phe Arg Arg Arg Leu Phe
                485                 490                 495

Leu Ile Pro Ile Lys Ser Trp Glu Asp Leu Thr Ser Asp Lys Asp Ala
            500                 505                 510

Ile Glu Thr Ile Arg Ala Ile Tyr Gly Asp Asp Val Glu Lys Leu Asp
        515                 520                 525

Leu Leu Val Gly Leu Met Ala Glu Lys Lys Ile Lys Gly Phe Ala Ile
    530                 535                 540
```

```
Ser Glu Thr Ala Phe Asn Ile Phe Ile Leu Met Ala Ser Arg Arg Leu
545                 550                 555                 560

Glu Ala Asp Arg Phe Phe Thr Ser Asn Phe Asn Glu Glu Thr Tyr Thr
                565                 570                 575

Lys Lys Gly Met Gln Trp Val Lys Thr Thr Glu Gly Leu Arg Asp Val
            580                 585                 590

Ile Asn Arg His Tyr Pro Glu Ile Thr Ala Lys Trp Met Lys Ser Ser
        595                 600                 605

Ser Ala Phe Ser Val Trp Asp Ala Asp Tyr
    610                 615


<210> SEQ ID NO 7
<211> LENGTH: 618
<212> TYPE: PRT
<213> ORGANISM: Artificial Sequence
<220> FEATURE:
<223> OTHER INFORMATION: D117K Substitution

<400> SEQUENCE: 7

Met Gly Ser Gly Leu Phe Lys Pro Arg Val His Pro Asp Leu Arg Asp
1               5                   10                  15

Val Phe Ser Lys Met Ser Phe Phe Asp Lys Ile Gly Phe Leu Phe Ile
            20                  25                  30

His Ala Phe Asp Lys Arg Asn Leu Trp His Lys Val Pro Val Pro Ile
        35                  40                  45

Gly Leu Leu Tyr Leu Asn Thr Arg Arg Thr Leu Leu Glu Lys Tyr Asn
    50                  55                  60

Leu Leu Ala Val Gly Arg Ser Ser His Gly Ala Leu Phe Asp Pro Lys
65                  70                  75                  80

Glu Phe Leu Tyr Arg Thr Glu Asp Gly Lys Tyr Asn Asp Pro His Asn
                85                  90                  95

Ala Glu Ala Gly Ser Gln Asn Thr Phe Phe Gly Arg Asn Met Glu Pro
            100                 105                 110

Val Asp Gln Gln Lys Glu Leu Met Ser Pro Asp Pro Phe Val Val Ala
        115                 120                 125

Thr Lys Leu Leu Ala Arg Arg Glu Tyr Lys Asp Thr Gly Lys Gln Phe
    130                 135                 140

Asn Ile Leu Ala Ala Ala Trp Ile Gln Phe Met Val His Asp Trp Met
145                 150                 155                 160

Asp His Met Glu Asp Thr Gly Gln Ile Gly Ile Thr Ala Pro Lys Glu
                165                 170                 175

Val Ala Asn Glu Cys Pro Leu Lys Ser Phe Lys Phe His Pro Thr Lys
            180                 185                 190

Glu Leu Pro Thr Asn Ser Asp Gly Ile Lys Ile Gly His Tyr Asn Ile
        195                 200                 205

Arg Thr Ala Trp Trp Asp Gly Ser Ala Val Tyr Gly Asn Asn Glu Glu
    210                 215                 220

Arg Ala Glu Lys Leu Arg Thr Tyr Val Asp Gly Lys Leu Val Ile Gly
225                 230                 235                 240

Asp Asp Gly Leu Leu Leu His Lys Glu Asn Gly Val Ala Leu Ser Gly
                245                 250                 255

Asp Ile Arg Asn Ser Trp Ala Gly Val Ser Ile Leu Gln Ala Leu Phe
            260                 265                 270

Val Lys Glu His Asn Ala Val Cys Asp Ala Ile Lys Glu Glu His Pro
        275                 280                 285
```

-continued

```
Asn Leu Ser Asp Glu Glu Leu Tyr Arg Tyr Ala Lys Leu Val Thr Ser
    290                 295                 300

Ala Val Ile Ala Lys Val His Thr Ile Asp Trp Thr Val Glu Leu Leu
305                 310                 315                 320

Lys Thr Lys Thr Met Arg Ala Ala Met Arg Ala Asn Trp Tyr Gly Leu
                325                 330                 335

Leu Gly Lys Lys Ile Lys Asp Thr Phe Gly His Ile Gly Gly Pro Ile
            340                 345                 350

Leu Gly Gly Leu Val Gly Leu Lys Lys Pro Asn Asn His Gly Val Pro
        355                 360                 365

Tyr Ser Leu Thr Glu Glu Phe Thr Ser Val Tyr Arg Met His Ser Leu
    370                 375                 380

Ile Pro Ser Thr Leu Lys Leu Arg Asp Pro Thr Gly Gln Pro Asp Ala
385                 390                 395                 400

Asn Asn Ser Pro Pro Cys Leu Glu Asp Ile Asp Ile Gly Glu Met Ile
                405                 410                 415

Gly Leu Lys Gly Glu Glu Gln Leu Ser Lys Ile Gly Phe Glu Lys Gln
            420                 425                 430

Ala Leu Ser Met Gly Tyr Gln Ala Cys Gly Ala Leu Glu Leu Trp Asn
        435                 440                 445

Tyr Pro Ser Phe Phe Arg Asn Leu Ile Pro Gln Asn Leu Asp Gly Thr
    450                 455                 460

Asn Arg Ser Asp Arg Ile Asp Leu Ala Ala Leu Glu Val Tyr Arg Asp
465                 470                 475                 480

Arg Glu Arg Ser Val Pro Arg Tyr Asn Glu Phe Arg Arg Arg Leu Phe
                485                 490                 495

Leu Ile Pro Ile Lys Ser Trp Glu Asp Leu Thr Ser Asp Lys Asp Ala
            500                 505                 510

Ile Glu Thr Ile Arg Ala Ile Tyr Gly Asp Asp Val Glu Lys Leu Asp
        515                 520                 525

Leu Leu Val Gly Leu Met Ala Glu Lys Lys Ile Lys Gly Phe Ala Ile
    530                 535                 540

Ser Glu Thr Ala Phe Asn Ile Phe Ile Leu Met Ala Ser Arg Arg Leu
545                 550                 555                 560

Glu Ala Asp Arg Phe Phe Thr Ser Asn Phe Asn Glu Glu Thr Tyr Thr
                565                 570                 575

Lys Lys Gly Met Gln Trp Val Lys Thr Thr Glu Gly Leu Arg Asp Val
            580                 585                 590

Ile Asn Arg His Tyr Pro Glu Ile Thr Ala Lys Trp Met Lys Ser Ser
        595                 600                 605

Ser Ala Phe Ser Val Trp Asp Ala Asp Tyr
    610                 615
```

<210> SEQ ID NO 8
<211> LENGTH: 618
<212> TYPE: PRT
<213> ORGANISM: Artificial Sequence
<220> FEATURE:
<223> OTHER INFORMATION: V156I Substitution

<400> SEQUENCE: 8

```
Met Gly Ser Gly Leu Phe Lys Pro Arg Val His Pro Asp Leu Arg Asp
1               5                   10                  15

Val Phe Ser Lys Met Ser Phe Phe Asp Lys Ile Gly Phe Leu Phe Ile
            20                  25                  30
```

-continued

```
His Ala Phe Asp Lys Arg Asn Leu Trp His Lys Val Pro Val Pro Ile
        35                  40                  45

Gly Leu Leu Tyr Leu Asn Thr Arg Arg Thr Leu Leu Glu Lys Tyr Asn
    50                  55                  60

Leu Leu Ala Val Gly Arg Ser Ser His Gly Ala Leu Phe Asp Pro Lys
65                  70                  75                  80

Glu Phe Leu Tyr Arg Thr Glu Asp Gly Lys Tyr Asn Asp Pro His Asn
                85                  90                  95

Ala Glu Ala Gly Ser Gln Asn Thr Phe Phe Gly Arg Asn Met Glu Pro
            100                 105                 110

Val Asp Gln Gln Asp Glu Leu Met Ser Pro Asp Pro Phe Val Val Ala
        115                 120                 125

Thr Lys Leu Leu Ala Arg Arg Glu Tyr Lys Asp Thr Gly Lys Gln Phe
    130                 135                 140

Asn Ile Leu Ala Ala Ala Trp Ile Gln Phe Met Ile His Asp Trp Met
145                 150                 155                 160

Asp His Met Glu Asp Thr Gly Gln Ile Gly Ile Thr Ala Pro Lys Glu
                165                 170                 175

Val Ala Asn Glu Cys Pro Leu Lys Ser Phe Lys Phe His Pro Thr Lys
            180                 185                 190

Glu Leu Pro Thr Asn Ser Asp Gly Ile Lys Ile Gly His Tyr Asn Ile
        195                 200                 205

Arg Thr Ala Trp Trp Asp Gly Ser Ala Val Tyr Gly Asn Asn Glu Glu
    210                 215                 220

Arg Ala Glu Lys Leu Arg Thr Tyr Val Asp Gly Lys Leu Val Ile Gly
225                 230                 235                 240

Asp Asp Gly Leu Leu Leu His Lys Glu Asn Gly Val Ala Leu Ser Gly
                245                 250                 255

Asp Ile Arg Asn Ser Trp Ala Gly Val Ser Ile Leu Gln Ala Leu Phe
            260                 265                 270

Val Lys Glu His Asn Ala Val Cys Asp Ala Ile Lys Glu Glu His Pro
        275                 280                 285

Asn Leu Ser Asp Glu Glu Leu Tyr Arg Tyr Ala Lys Leu Val Thr Ser
    290                 295                 300

Ala Val Ile Ala Lys Val His Thr Ile Asp Trp Thr Val Glu Leu Leu
305                 310                 315                 320

Lys Thr Lys Thr Met Arg Ala Ala Met Arg Ala Asn Trp Tyr Gly Leu
                325                 330                 335

Leu Gly Lys Lys Ile Lys Asp Thr Phe Gly His Ile Gly Gly Pro Ile
            340                 345                 350

Leu Gly Gly Leu Val Gly Leu Lys Lys Pro Asn Asn His Gly Val Pro
        355                 360                 365

Tyr Ser Leu Thr Glu Glu Phe Thr Ser Val Tyr Arg Met His Ser Leu
    370                 375                 380

Ile Pro Ser Thr Leu Lys Leu Arg Asp Pro Thr Gly Gln Pro Asp Ala
385                 390                 395                 400

Asn Asn Ser Pro Pro Cys Leu Glu Asp Ile Asp Ile Gly Glu Met Ile
                405                 410                 415

Gly Leu Lys Gly Glu Glu Gln Leu Ser Lys Ile Gly Phe Glu Lys Gln
            420                 425                 430

Ala Leu Ser Met Gly Tyr Gln Ala Cys Gly Ala Leu Glu Leu Trp Asn
        435                 440                 445

Tyr Pro Ser Phe Phe Arg Asn Leu Ile Pro Gln Asn Leu Asp Gly Thr
```

-continued

```
    450                 455                 460

Asn Arg Ser Asp Arg Ile Asp Leu Ala Ala Leu Glu Val Tyr Arg Asp
465                 470                 475                 480

Arg Glu Arg Ser Val Pro Arg Tyr Asn Glu Phe Arg Arg Arg Leu Phe
                485                 490                 495

Leu Ile Pro Ile Lys Ser Trp Glu Asp Leu Thr Ser Asp Lys Asp Ala
            500                 505                 510

Ile Glu Thr Ile Arg Ala Ile Tyr Gly Asp Asp Val Glu Lys Leu Asp
        515                 520                 525

Leu Leu Val Gly Leu Met Ala Glu Lys Lys Ile Lys Gly Phe Ala Ile
    530                 535                 540

Ser Glu Thr Ala Phe Asn Ile Phe Ile Leu Met Ala Ser Arg Arg Leu
545                 550                 555                 560

Glu Ala Asp Arg Phe Phe Thr Ser Asn Phe Asn Glu Glu Thr Tyr Thr
                565                 570                 575

Lys Lys Gly Met Gln Trp Val Lys Thr Thr Glu Gly Leu Arg Asp Val
            580                 585                 590

Ile Asn Arg His Tyr Pro Glu Ile Thr Ala Lys Trp Met Lys Ser Ser
        595                 600                 605

Ser Ala Phe Ser Val Trp Asp Ala Asp Tyr
    610                 615
```

<210> SEQ ID NO 9
<211> LENGTH: 618
<212> TYPE: PRT
<213> ORGANISM: Artificial Sequence
<220> FEATURE:
<223> OTHER INFORMATION: M160I Substitution

<400> SEQUENCE: 9

```
Met Gly Ser Gly Leu Phe Lys Pro Arg Val His Pro Asp Leu Arg Asp
1               5                   10                  15

Val Phe Ser Lys Met Ser Phe Phe Asp Lys Ile Gly Phe Leu Phe Ile
            20                  25                  30

His Ala Phe Asp Lys Arg Asn Leu Trp His Lys Val Pro Val Pro Ile
        35                  40                  45

Gly Leu Leu Tyr Leu Asn Thr Arg Arg Thr Leu Leu Glu Lys Tyr Asn
    50                  55                  60

Leu Leu Ala Val Gly Arg Ser Ser His Gly Ala Leu Phe Asp Pro Lys
65                  70                  75                  80

Glu Phe Leu Tyr Arg Thr Glu Asp Gly Lys Tyr Asn Asp Pro His Asn
                85                  90                  95

Ala Glu Ala Gly Ser Gln Asn Thr Phe Phe Gly Arg Asn Met Glu Pro
            100                 105                 110

Val Asp Gln Gln Asp Glu Leu Met Ser Pro Asp Pro Phe Val Val Ala
        115                 120                 125

Thr Lys Leu Leu Ala Arg Arg Glu Tyr Lys Asp Thr Gly Lys Gln Phe
    130                 135                 140

Asn Ile Leu Ala Ala Ala Trp Ile Gln Phe Met Val His Asp Trp Ile
145                 150                 155                 160

Asp His Met Glu Asp Thr Gly Gln Ile Gly Ile Thr Ala Pro Lys Glu
                165                 170                 175

Val Ala Asn Glu Cys Pro Leu Lys Ser Phe Lys Phe His Pro Thr Lys
            180                 185                 190

Glu Leu Pro Thr Asn Ser Asp Gly Ile Lys Ile Gly His Tyr Asn Ile
```

-continued

```
        195                 200                 205

Arg Thr Ala Trp Trp Asp Gly Ser Ala Val Tyr Gly Asn Asn Glu Glu
    210                 215                 220

Arg Ala Glu Lys Leu Arg Thr Tyr Val Asp Gly Lys Leu Val Ile Gly
225                 230                 235                 240

Asp Asp Gly Leu Leu Leu His Lys Glu Asn Gly Val Ala Leu Ser Gly
                245                 250                 255

Asp Ile Arg Asn Ser Trp Ala Gly Val Ser Ile Leu Gln Ala Leu Phe
            260                 265                 270

Val Lys Glu His Asn Ala Val Cys Asp Ala Ile Lys Glu Glu His Pro
        275                 280                 285

Asn Leu Ser Asp Glu Glu Leu Tyr Arg Tyr Ala Lys Leu Val Thr Ser
    290                 295                 300

Ala Val Ile Ala Lys Val His Thr Ile Asp Trp Thr Val Glu Leu Leu
305                 310                 315                 320

Lys Thr Lys Thr Met Arg Ala Ala Met Arg Ala Asn Trp Tyr Gly Leu
                325                 330                 335

Leu Gly Lys Lys Ile Lys Asp Thr Phe Gly His Ile Gly Gly Pro Ile
            340                 345                 350

Leu Gly Gly Leu Val Gly Leu Lys Lys Pro Asn Asn His Gly Val Pro
        355                 360                 365

Tyr Ser Leu Thr Glu Glu Phe Thr Ser Val Tyr Arg Met His Ser Leu
    370                 375                 380

Ile Pro Ser Thr Leu Lys Leu Arg Asp Pro Thr Gly Gln Pro Asp Ala
385                 390                 395                 400

Asn Asn Ser Pro Pro Cys Leu Glu Asp Ile Asp Ile Gly Glu Met Ile
                405                 410                 415

Gly Leu Lys Gly Glu Glu Gln Leu Ser Lys Ile Gly Phe Glu Lys Gln
            420                 425                 430

Ala Leu Ser Met Gly Tyr Gln Ala Cys Gly Ala Leu Glu Leu Trp Asn
        435                 440                 445

Tyr Pro Ser Phe Phe Arg Asn Leu Ile Pro Gln Asn Leu Asp Gly Thr
    450                 455                 460

Asn Arg Ser Asp Arg Ile Asp Leu Ala Ala Leu Glu Val Tyr Arg Asp
465                 470                 475                 480

Arg Glu Arg Ser Val Pro Arg Tyr Asn Glu Phe Arg Arg Arg Leu Phe
                485                 490                 495

Leu Ile Pro Ile Lys Ser Trp Glu Asp Leu Thr Ser Asp Lys Asp Ala
            500                 505                 510

Ile Glu Thr Ile Arg Ala Ile Tyr Gly Asp Asp Val Glu Lys Leu Asp
        515                 520                 525

Leu Leu Val Gly Leu Met Ala Glu Lys Lys Ile Lys Gly Phe Ala Ile
    530                 535                 540

Ser Glu Thr Ala Phe Asn Ile Phe Ile Leu Met Ala Ser Arg Arg Leu
545                 550                 555                 560

Glu Ala Asp Arg Phe Phe Thr Ser Asn Phe Asn Glu Glu Thr Tyr Thr
                565                 570                 575

Lys Lys Gly Met Gln Trp Val Lys Thr Thr Glu Gly Leu Arg Asp Val
            580                 585                 590

Ile Asn Arg His Tyr Pro Glu Ile Thr Ala Lys Trp Met Lys Ser Ser
        595                 600                 605

Ser Ala Phe Ser Val Trp Asp Ala Asp Tyr
    610                 615
```

<210> SEQ ID NO 10
<211> LENGTH: 618
<212> TYPE: PRT
<213> ORGANISM: Artificial Sequence
<220> FEATURE:
<223> OTHER INFORMATION: M160T Substitution

<400> SEQUENCE: 10

Met Gly Ser Gly Leu Phe Lys Pro Arg Val His Pro Asp Leu Arg Asp
1 5 10 15

Val Phe Ser Lys Met Ser Phe Phe Asp Lys Ile Gly Phe Leu Phe Ile
20 25 30

His Ala Phe Asp Lys Arg Asn Leu Trp His Lys Val Pro Val Pro Ile
35 40 45

Gly Leu Leu Tyr Leu Asn Thr Arg Arg Thr Leu Leu Glu Lys Tyr Asn
50 55 60

Leu Leu Ala Val Gly Arg Ser Ser His Gly Ala Leu Phe Asp Pro Lys
65 70 75 80

Glu Phe Leu Tyr Arg Thr Glu Asp Gly Lys Tyr Asn Asp Pro His Asn
85 90 95

Ala Glu Ala Gly Ser Gln Asn Thr Phe Phe Gly Arg Asn Met Glu Pro
100 105 110

Val Asp Gln Gln Asp Glu Leu Met Ser Pro Asp Pro Phe Val Val Ala
115 120 125

Thr Lys Leu Leu Ala Arg Arg Glu Tyr Lys Asp Thr Gly Lys Gln Phe
130 135 140

Asn Ile Leu Ala Ala Ala Trp Ile Gln Phe Met Val His Asp Trp Thr
145 150 155 160

Asp His Met Glu Asp Thr Gly Gln Ile Gly Ile Thr Ala Pro Lys Glu
165 170 175

Val Ala Asn Glu Cys Pro Leu Lys Ser Phe Lys Phe His Pro Thr Lys
180 185 190

Glu Leu Pro Thr Asn Ser Asp Gly Ile Lys Ile Gly His Tyr Asn Ile
195 200 205

Arg Thr Ala Trp Trp Asp Gly Ser Ala Val Tyr Gly Asn Asn Glu Glu
210 215 220

Arg Ala Glu Lys Leu Arg Thr Tyr Val Asp Gly Lys Leu Val Ile Gly
225 230 235 240

Asp Asp Gly Leu Leu Leu His Lys Glu Asn Gly Val Ala Leu Ser Gly
245 250 255

Asp Ile Arg Asn Ser Trp Ala Gly Val Ser Ile Leu Gln Ala Leu Phe
260 265 270

Val Lys Glu His Asn Ala Val Cys Asp Ala Ile Lys Glu Glu His Pro
275 280 285

Asn Leu Ser Asp Glu Glu Leu Tyr Arg Tyr Ala Lys Leu Val Thr Ser
290 295 300

Ala Val Ile Ala Lys Val His Thr Ile Asp Trp Thr Val Glu Leu Leu
305 310 315 320

Lys Thr Lys Thr Met Arg Ala Ala Met Arg Ala Asn Trp Tyr Gly Leu
325 330 335

Leu Gly Lys Lys Ile Lys Asp Thr Phe Gly His Ile Gly Gly Pro Ile
340 345 350

Leu Gly Gly Leu Val Gly Leu Lys Lys Pro Asn Asn His Gly Val Pro
355 360 365

Tyr Ser Leu Thr Glu Glu Phe Thr Ser Val Tyr Arg Met His Ser Leu
370 375 380

Ile Pro Ser Thr Leu Lys Leu Arg Asp Pro Thr Gly Gln Pro Asp Ala
385 390 395 400

Asn Asn Ser Pro Pro Cys Leu Glu Asp Ile Asp Ile Gly Glu Met Ile
405 410 415

Gly Leu Lys Gly Glu Glu Gln Leu Ser Lys Ile Gly Phe Glu Lys Gln
420 425 430

Ala Leu Ser Met Gly Tyr Gln Ala Cys Gly Ala Leu Glu Leu Trp Asn
435 440 445

Tyr Pro Ser Phe Phe Arg Asn Leu Ile Pro Gln Asn Leu Asp Gly Thr
450 455 460

Asn Arg Ser Asp Arg Ile Asp Leu Ala Ala Leu Glu Val Tyr Arg Asp
465 470 475 480

Arg Glu Arg Ser Val Pro Arg Tyr Asn Glu Phe Arg Arg Arg Leu Phe
485 490 495

Leu Ile Pro Ile Lys Ser Trp Glu Asp Leu Thr Ser Asp Lys Asp Ala
500 505 510

Ile Glu Thr Ile Arg Ala Ile Tyr Gly Asp Asp Val Glu Lys Leu Asp
515 520 525

Leu Leu Val Gly Leu Met Ala Glu Lys Lys Ile Lys Gly Phe Ala Ile
530 535 540

Ser Glu Thr Ala Phe Asn Ile Phe Ile Leu Met Ala Ser Arg Arg Leu
545 550 555 560

Glu Ala Asp Arg Phe Phe Thr Ser Asn Phe Asn Glu Glu Thr Tyr Thr
565 570 575

Lys Lys Gly Met Gln Trp Val Lys Thr Thr Glu Gly Leu Arg Asp Val
580 585 590

Ile Asn Arg His Tyr Pro Glu Ile Thr Ala Lys Trp Met Lys Ser Ser
595 600 605

Ser Ala Phe Ser Val Trp Asp Ala Asp Tyr
610 615

<210> SEQ ID NO 11
<211> LENGTH: 618
<212> TYPE: PRT
<213> ORGANISM: Artificial Sequence
<220> FEATURE:
<223> OTHER INFORMATION: G200D Substitution

<400> SEQUENCE: 11

Met Gly Ser Gly Leu Phe Lys Pro Arg Val His Pro Asp Leu Arg Asp
1 5 10 15

Val Phe Ser Lys Met Ser Phe Phe Asp Lys Ile Gly Phe Leu Phe Ile
20 25 30

His Ala Phe Asp Lys Arg Asn Leu Trp His Lys Val Pro Val Pro Ile
35 40 45

Gly Leu Leu Tyr Leu Asn Thr Arg Arg Thr Leu Leu Glu Lys Tyr Asn
50 55 60

Leu Leu Ala Val Gly Arg Ser Ser His Gly Ala Leu Phe Asp Pro Lys
65 70 75 80

Glu Phe Leu Tyr Arg Thr Glu Asp Gly Lys Tyr Asn Asp Pro His Asn
85 90 95

Ala Glu Ala Gly Ser Gln Asn Thr Phe Phe Gly Arg Asn Met Glu Pro
100 105 110

-continued

```
Val Asp Gln Gln Asp Glu Leu Met Ser Pro Asp Pro Phe Val Val Ala
        115                 120                 125

Thr Lys Leu Leu Ala Arg Arg Glu Tyr Lys Asp Thr Gly Lys Gln Phe
    130                 135                 140

Asn Ile Leu Ala Ala Ala Trp Ile Gln Phe Met Val His Asp Trp Met
145                 150                 155                 160

Asp His Met Glu Asp Thr Gly Gln Ile Gly Ile Thr Ala Pro Lys Glu
                165                 170                 175

Val Ala Asn Glu Cys Pro Leu Lys Ser Phe Lys Phe His Pro Thr Lys
            180                 185                 190

Glu Leu Pro Thr Asn Ser Asp Asp Ile Lys Ile Gly His Tyr Asn Ile
        195                 200                 205

Arg Thr Ala Trp Trp Asp Gly Ser Ala Val Tyr Gly Asn Asn Glu Glu
    210                 215                 220

Arg Ala Glu Lys Leu Arg Thr Tyr Val Asp Gly Lys Leu Val Ile Gly
225                 230                 235                 240

Asp Asp Gly Leu Leu Leu His Lys Glu Asn Gly Val Ala Leu Ser Gly
                245                 250                 255

Asp Ile Arg Asn Ser Trp Ala Gly Val Ser Ile Leu Gln Ala Leu Phe
            260                 265                 270

Val Lys Glu His Asn Ala Val Cys Asp Ala Ile Lys Glu Glu His Pro
        275                 280                 285

Asn Leu Ser Asp Glu Glu Leu Tyr Arg Tyr Ala Lys Leu Val Thr Ser
    290                 295                 300

Ala Val Ile Ala Lys Val His Thr Ile Asp Trp Thr Val Glu Leu Leu
305                 310                 315                 320

Lys Thr Lys Thr Met Arg Ala Ala Met Arg Ala Asn Trp Tyr Gly Leu
                325                 330                 335

Leu Gly Lys Lys Ile Lys Asp Thr Phe Gly His Ile Gly Gly Pro Ile
            340                 345                 350

Leu Gly Gly Leu Val Gly Leu Lys Lys Pro Asn Asn His Gly Val Pro
        355                 360                 365

Tyr Ser Leu Thr Glu Glu Phe Thr Ser Val Tyr Arg Met His Ser Leu
    370                 375                 380

Ile Pro Ser Thr Leu Lys Leu Arg Asp Pro Thr Gly Gln Pro Asp Ala
385                 390                 395                 400

Asn Asn Ser Pro Pro Cys Leu Glu Asp Ile Asp Ile Gly Glu Met Ile
                405                 410                 415

Gly Leu Lys Gly Glu Glu Gln Leu Ser Lys Ile Gly Phe Glu Lys Gln
            420                 425                 430

Ala Leu Ser Met Gly Tyr Gln Ala Cys Gly Ala Leu Glu Leu Trp Asn
        435                 440                 445

Tyr Pro Ser Phe Phe Arg Asn Leu Ile Pro Gln Asn Leu Asp Gly Thr
    450                 455                 460

Asn Arg Ser Asp Arg Ile Asp Leu Ala Ala Leu Glu Val Tyr Arg Asp
465                 470                 475                 480

Arg Glu Arg Ser Val Pro Arg Tyr Asn Glu Phe Arg Arg Arg Leu Phe
                485                 490                 495

Leu Ile Pro Ile Lys Ser Trp Glu Asp Leu Thr Ser Asp Lys Asp Ala
            500                 505                 510

Ile Glu Thr Ile Arg Ala Ile Tyr Gly Asp Asp Val Glu Lys Leu Asp
        515                 520                 525
```

```
Leu Leu Val Gly Leu Met Ala Glu Lys Lys Ile Lys Gly Phe Ala Ile
    530                 535                 540

Ser Glu Thr Ala Phe Asn Ile Phe Ile Leu Met Ala Ser Arg Arg Leu
545                 550                 555                 560

Glu Ala Asp Arg Phe Phe Thr Ser Asn Phe Asn Glu Glu Thr Tyr Thr
                565                 570                 575

Lys Lys Gly Met Gln Trp Val Lys Thr Thr Glu Gly Leu Arg Asp Val
            580                 585                 590

Ile Asn Arg His Tyr Pro Glu Ile Thr Ala Lys Trp Met Lys Ser Ser
        595                 600                 605

Ser Ala Phe Ser Val Trp Asp Ala Asp Tyr
    610                 615


<210> SEQ ID NO 12
<211> LENGTH: 618
<212> TYPE: PRT
<213> ORGANISM: Artificial Sequence
<220> FEATURE:
<223> OTHER INFORMATION: R225V Substitution

<400> SEQUENCE: 12

Met Gly Ser Gly Leu Phe Lys Pro Arg Val His Pro Asp Leu Arg Asp
1               5                   10                  15

Val Phe Ser Lys Met Ser Phe Phe Asp Lys Ile Gly Phe Leu Phe Ile
            20                  25                  30

His Ala Phe Asp Lys Arg Asn Leu Trp His Lys Val Pro Val Pro Ile
        35                  40                  45

Gly Leu Leu Tyr Leu Asn Thr Arg Arg Thr Leu Leu Glu Lys Tyr Asn
    50                  55                  60

Leu Leu Ala Val Gly Arg Ser Ser His Gly Ala Leu Phe Asp Pro Lys
65                  70                  75                  80

Glu Phe Leu Tyr Arg Thr Glu Asp Gly Lys Tyr Asn Asp Pro His Asn
                85                  90                  95

Ala Glu Ala Gly Ser Gln Asn Thr Phe Phe Gly Arg Asn Met Glu Pro
            100                 105                 110

Val Asp Gln Gln Asp Glu Leu Met Ser Pro Asp Pro Phe Val Val Ala
        115                 120                 125

Thr Lys Leu Leu Ala Arg Arg Glu Tyr Lys Asp Thr Gly Lys Gln Phe
    130                 135                 140

Asn Ile Leu Ala Ala Ala Trp Ile Gln Phe Met Val His Asp Trp Met
145                 150                 155                 160

Asp His Met Glu Asp Thr Gly Gln Ile Gly Ile Thr Ala Pro Lys Glu
                165                 170                 175

Val Ala Asn Glu Cys Pro Leu Lys Ser Phe Lys Phe His Pro Thr Lys
            180                 185                 190

Glu Leu Pro Thr Asn Ser Asp Gly Ile Lys Ile Gly His Tyr Asn Ile
        195                 200                 205

Arg Thr Ala Trp Trp Asp Gly Ser Ala Val Tyr Gly Asn Asn Glu Glu
    210                 215                 220

Val Ala Glu Lys Leu Arg Thr Tyr Val Asp Gly Lys Leu Val Ile Gly
225                 230                 235                 240

Asp Asp Gly Leu Leu Leu His Lys Glu Asn Gly Val Ala Leu Ser Gly
                245                 250                 255

Asp Ile Arg Asn Ser Trp Ala Gly Val Ser Ile Leu Gln Ala Leu Phe
            260                 265                 270
```

-continued

```
Val Lys Glu His Asn Ala Val Cys Asp Ala Ile Lys Glu Glu His Pro
        275                 280                 285

Asn Leu Ser Asp Glu Glu Leu Tyr Arg Tyr Ala Lys Leu Val Thr Ser
    290                 295                 300

Ala Val Ile Ala Lys Val His Thr Ile Asp Trp Thr Val Glu Leu Leu
305                 310                 315                 320

Lys Thr Lys Thr Met Arg Ala Ala Met Arg Ala Asn Trp Tyr Gly Leu
                325                 330                 335

Leu Gly Lys Lys Ile Lys Asp Thr Phe Gly His Ile Gly Gly Pro Ile
            340                 345                 350

Leu Gly Gly Leu Val Gly Leu Lys Lys Pro Asn Asn His Gly Val Pro
        355                 360                 365

Tyr Ser Leu Thr Glu Glu Phe Thr Ser Val Tyr Arg Met His Ser Leu
    370                 375                 380

Ile Pro Ser Thr Leu Lys Leu Arg Asp Pro Thr Gly Gln Pro Asp Ala
385                 390                 395                 400

Asn Asn Ser Pro Pro Cys Leu Glu Asp Ile Asp Ile Gly Glu Met Ile
                405                 410                 415

Gly Leu Lys Gly Glu Glu Gln Leu Ser Lys Ile Gly Phe Glu Lys Gln
            420                 425                 430

Ala Leu Ser Met Gly Tyr Gln Ala Cys Gly Ala Leu Glu Leu Trp Asn
        435                 440                 445

Tyr Pro Ser Phe Phe Arg Asn Leu Ile Pro Gln Asn Leu Asp Gly Thr
    450                 455                 460

Asn Arg Ser Asp Arg Ile Asp Leu Ala Ala Leu Glu Val Tyr Arg Asp
465                 470                 475                 480

Arg Glu Arg Ser Val Pro Arg Tyr Asn Glu Phe Arg Arg Arg Leu Phe
                485                 490                 495

Leu Ile Pro Ile Lys Ser Trp Glu Asp Leu Thr Ser Asp Lys Asp Ala
            500                 505                 510

Ile Glu Thr Ile Arg Ala Ile Tyr Gly Asp Asp Val Glu Lys Leu Asp
        515                 520                 525

Leu Leu Val Gly Leu Met Ala Glu Lys Lys Ile Lys Gly Phe Ala Ile
    530                 535                 540

Ser Glu Thr Ala Phe Asn Ile Phe Ile Leu Met Ala Ser Arg Arg Leu
545                 550                 555                 560

Glu Ala Asp Arg Phe Phe Thr Ser Asn Phe Asn Glu Glu Thr Tyr Thr
                565                 570                 575

Lys Lys Gly Met Gln Trp Val Lys Thr Thr Glu Gly Leu Arg Asp Val
            580                 585                 590

Ile Asn Arg His Tyr Pro Glu Ile Thr Ala Lys Trp Met Lys Ser Ser
        595                 600                 605

Ser Ala Phe Ser Val Trp Asp Ala Asp Tyr
    610                 615
```

<210> SEQ ID NO 13
<211> LENGTH: 618
<212> TYPE: PRT
<213> ORGANISM: Artificial Sequence
<220> FEATURE:
<223> OTHER INFORMATION: K248S Substitution

<400> SEQUENCE: 13

```
Met Gly Ser Gly Leu Phe Lys Pro Arg Val His Pro Asp Leu Arg Asp
1               5                   10                  15
```

-continued

```
Val Phe Ser Lys Met Ser Phe Phe Asp Lys Ile Gly Phe Leu Phe Ile
            20                  25                  30

His Ala Phe Asp Lys Arg Asn Leu Trp His Lys Val Pro Val Pro Ile
        35                  40                  45

Gly Leu Leu Tyr Leu Asn Thr Arg Arg Thr Leu Leu Glu Lys Tyr Asn
    50                  55                  60

Leu Leu Ala Val Gly Arg Ser Ser His Gly Ala Leu Phe Asp Pro Lys
65                  70                  75                  80

Glu Phe Leu Tyr Arg Thr Glu Asp Gly Lys Tyr Asn Asp Pro His Asn
                85                  90                  95

Ala Glu Ala Gly Ser Gln Asn Thr Phe Phe Gly Arg Asn Met Glu Pro
            100                 105                 110

Val Asp Gln Gln Asp Glu Leu Met Ser Pro Asp Pro Phe Val Val Ala
        115                 120                 125

Thr Lys Leu Leu Ala Arg Arg Glu Tyr Lys Asp Thr Gly Lys Gln Phe
    130                 135                 140

Asn Ile Leu Ala Ala Ala Trp Ile Gln Phe Met Val His Asp Trp Met
145                 150                 155                 160

Asp His Met Glu Asp Thr Gly Gln Ile Gly Ile Thr Ala Pro Lys Glu
                165                 170                 175

Val Ala Asn Glu Cys Pro Leu Lys Ser Phe Lys Phe His Pro Thr Lys
            180                 185                 190

Glu Leu Pro Thr Asn Ser Asp Gly Ile Lys Ile Gly His Tyr Asn Ile
        195                 200                 205

Arg Thr Ala Trp Trp Asp Gly Ser Ala Val Tyr Gly Asn Asn Glu Glu
    210                 215                 220

Arg Ala Glu Lys Leu Arg Thr Tyr Val Asp Gly Lys Leu Val Ile Gly
225                 230                 235                 240

Asp Asp Gly Leu Leu Leu His Ser Glu Asn Gly Val Ala Leu Ser Gly
                245                 250                 255

Asp Ile Arg Asn Ser Trp Ala Gly Val Ser Ile Leu Gln Ala Leu Phe
            260                 265                 270

Val Lys Glu His Asn Ala Val Cys Asp Ala Ile Lys Glu Glu His Pro
        275                 280                 285

Asn Leu Ser Asp Glu Glu Leu Tyr Arg Tyr Ala Lys Leu Val Thr Ser
    290                 295                 300

Ala Val Ile Ala Lys Val His Thr Ile Asp Trp Thr Val Glu Leu Leu
305                 310                 315                 320

Lys Thr Lys Thr Met Arg Ala Ala Met Arg Ala Asn Trp Tyr Gly Leu
                325                 330                 335

Leu Gly Lys Lys Ile Lys Asp Thr Phe Gly His Ile Gly Gly Pro Ile
            340                 345                 350

Leu Gly Gly Leu Val Gly Leu Lys Lys Pro Asn Asn His Gly Val Pro
        355                 360                 365

Tyr Ser Leu Thr Glu Glu Phe Thr Ser Val Tyr Arg Met His Ser Leu
    370                 375                 380

Ile Pro Ser Thr Leu Lys Leu Arg Asp Pro Thr Gly Gln Pro Asp Ala
385                 390                 395                 400

Asn Asn Ser Pro Pro Cys Leu Glu Asp Ile Asp Ile Gly Glu Met Ile
                405                 410                 415

Gly Leu Lys Gly Glu Glu Gln Leu Ser Lys Ile Gly Phe Glu Lys Gln
            420                 425                 430

Ala Leu Ser Met Gly Tyr Gln Ala Cys Gly Ala Leu Glu Leu Trp Asn
```

```
        435                 440                 445

Tyr Pro Ser Phe Phe Arg Asn Leu Ile Pro Gln Asn Leu Asp Gly Thr
    450                 455                 460

Asn Arg Ser Asp Arg Ile Asp Leu Ala Ala Leu Glu Val Tyr Arg Asp
465                 470                 475                 480

Arg Glu Arg Ser Val Pro Arg Tyr Asn Glu Phe Arg Arg Arg Leu Phe
                485                 490                 495

Leu Ile Pro Ile Lys Ser Trp Glu Asp Leu Thr Ser Asp Lys Asp Ala
            500                 505                 510

Ile Glu Thr Ile Arg Ala Ile Tyr Gly Asp Asp Val Glu Lys Leu Asp
        515                 520                 525

Leu Leu Val Gly Leu Met Ala Glu Lys Lys Ile Lys Gly Phe Ala Ile
    530                 535                 540

Ser Glu Thr Ala Phe Asn Ile Phe Ile Leu Met Ala Ser Arg Arg Leu
545                 550                 555                 560

Glu Ala Asp Arg Phe Phe Thr Ser Asn Phe Asn Glu Glu Thr Tyr Thr
                565                 570                 575

Lys Lys Gly Met Gln Trp Val Lys Thr Thr Glu Gly Leu Arg Asp Val
            580                 585                 590

Ile Asn Arg His Tyr Pro Glu Ile Thr Ala Lys Trp Met Lys Ser Ser
        595                 600                 605

Ser Ala Phe Ser Val Trp Asp Ala Asp Tyr
    610                 615


<210> SEQ ID NO 14
<211> LENGTH: 618
<212> TYPE: PRT
<213> ORGANISM: Artificial Sequence
<220> FEATURE:
<223> OTHER INFORMATION: K248T Substitution

<400> SEQUENCE: 14

Met Gly Ser Gly Leu Phe Lys Pro Arg Val His Pro Asp Leu Arg Asp
1               5                   10                  15

Val Phe Ser Lys Met Ser Phe Phe Asp Lys Ile Gly Phe Leu Phe Ile
            20                  25                  30

His Ala Phe Asp Lys Arg Asn Leu Trp His Lys Val Pro Val Pro Ile
        35                  40                  45

Gly Leu Leu Tyr Leu Asn Thr Arg Arg Thr Leu Leu Glu Lys Tyr Asn
    50                  55                  60

Leu Leu Ala Val Gly Arg Ser Ser His Gly Ala Leu Phe Asp Pro Lys
65                  70                  75                  80

Glu Phe Leu Tyr Arg Thr Glu Asp Gly Lys Tyr Asn Asp Pro His Asn
                85                  90                  95

Ala Glu Ala Gly Ser Gln Asn Thr Phe Phe Gly Arg Asn Met Glu Pro
            100                 105                 110

Val Asp Gln Gln Asp Glu Leu Met Ser Pro Asp Pro Phe Val Val Ala
        115                 120                 125

Thr Lys Leu Leu Ala Arg Arg Glu Tyr Lys Asp Thr Gly Lys Gln Phe
    130                 135                 140

Asn Ile Leu Ala Ala Ala Trp Ile Gln Phe Met Val His Asp Trp Met
145                 150                 155                 160

Asp His Met Glu Asp Thr Gly Gln Ile Gly Ile Thr Ala Pro Lys Glu
                165                 170                 175

Val Ala Asn Glu Cys Pro Leu Lys Ser Phe Lys Phe His Pro Thr Lys
```

-continued

```
            180                 185                 190

Glu Leu Pro Thr Asn Ser Asp Gly Ile Lys Ile Gly His Tyr Asn Ile
        195                 200                 205

Arg Thr Ala Trp Trp Asp Gly Ser Ala Val Tyr Gly Asn Asn Glu Glu
    210                 215                 220

Arg Ala Glu Lys Leu Arg Thr Tyr Val Asp Gly Lys Leu Val Ile Gly
225                 230                 235                 240

Asp Asp Gly Leu Leu Leu His Thr Glu Asn Gly Val Ala Leu Ser Gly
                245                 250                 255

Asp Ile Arg Asn Ser Trp Ala Gly Val Ser Ile Leu Gln Ala Leu Phe
            260                 265                 270

Val Lys Glu His Asn Ala Val Cys Asp Ala Ile Lys Glu Glu His Pro
        275                 280                 285

Asn Leu Ser Asp Glu Glu Leu Tyr Arg Tyr Ala Lys Leu Val Thr Ser
    290                 295                 300

Ala Val Ile Ala Lys Val His Thr Ile Asp Trp Thr Val Glu Leu Leu
305                 310                 315                 320

Lys Thr Lys Thr Met Arg Ala Ala Met Arg Ala Asn Trp Tyr Gly Leu
                325                 330                 335

Leu Gly Lys Lys Ile Lys Asp Thr Phe Gly His Ile Gly Gly Pro Ile
            340                 345                 350

Leu Gly Gly Leu Val Gly Leu Lys Lys Pro Asn Asn His Gly Val Pro
        355                 360                 365

Tyr Ser Leu Thr Glu Glu Phe Thr Ser Val Tyr Arg Met His Ser Leu
    370                 375                 380

Ile Pro Ser Thr Leu Lys Leu Arg Asp Pro Thr Gly Gln Pro Asp Ala
385                 390                 395                 400

Asn Asn Ser Pro Pro Cys Leu Glu Asp Ile Asp Ile Gly Glu Met Ile
                405                 410                 415

Gly Leu Lys Gly Glu Glu Gln Leu Ser Lys Ile Gly Phe Glu Lys Gln
            420                 425                 430

Ala Leu Ser Met Gly Tyr Gln Ala Cys Gly Ala Leu Glu Leu Trp Asn
        435                 440                 445

Tyr Pro Ser Phe Phe Arg Asn Leu Ile Pro Gln Asn Leu Asp Gly Thr
    450                 455                 460

Asn Arg Ser Asp Arg Ile Asp Leu Ala Ala Leu Glu Val Tyr Arg Asp
465                 470                 475                 480

Arg Glu Arg Ser Val Pro Arg Tyr Asn Glu Phe Arg Arg Arg Leu Phe
                485                 490                 495

Leu Ile Pro Ile Lys Ser Trp Glu Asp Leu Thr Ser Asp Lys Asp Ala
            500                 505                 510

Ile Glu Thr Ile Arg Ala Ile Tyr Gly Asp Asp Val Glu Lys Leu Asp
        515                 520                 525

Leu Leu Val Gly Leu Met Ala Glu Lys Lys Ile Lys Gly Phe Ala Ile
    530                 535                 540

Ser Glu Thr Ala Phe Asn Ile Phe Ile Leu Met Ala Ser Arg Arg Leu
545                 550                 555                 560

Glu Ala Asp Arg Phe Phe Thr Ser Asn Phe Asn Glu Glu Thr Tyr Thr
                565                 570                 575

Lys Lys Gly Met Gln Trp Val Lys Thr Thr Glu Gly Leu Arg Asp Val
            580                 585                 590

Ile Asn Arg His Tyr Pro Glu Ile Thr Ala Lys Trp Met Lys Ser Ser
        595                 600                 605
```

Ser Ala Phe Ser Val Trp Asp Ala Asp Tyr
610 615

<210> SEQ ID NO 15
<211> LENGTH: 618
<212> TYPE: PRT
<213> ORGANISM: Artificial Sequence
<220> FEATURE:
<223> OTHER INFORMATION: M329L Substitution

<400> SEQUENCE: 15

Met Gly Ser Gly Leu Phe Lys Pro Arg Val His Pro Asp Leu Arg Asp
1 5 10 15

Val Phe Ser Lys Met Ser Phe Phe Asp Lys Ile Gly Phe Leu Phe Ile
20 25 30

His Ala Phe Asp Lys Arg Asn Leu Trp His Lys Val Pro Val Pro Ile
35 40 45

Gly Leu Leu Tyr Leu Asn Thr Arg Arg Thr Leu Leu Glu Lys Tyr Asn
50 55 60

Leu Leu Ala Val Gly Arg Ser Ser His Gly Ala Leu Phe Asp Pro Lys
65 70 75 80

Glu Phe Leu Tyr Arg Thr Glu Asp Gly Lys Tyr Asn Asp Pro His Asn
85 90 95

Ala Glu Ala Gly Ser Gln Asn Thr Phe Phe Gly Arg Asn Met Glu Pro
100 105 110

Val Asp Gln Gln Asp Glu Leu Met Ser Pro Asp Pro Phe Val Val Ala
115 120 125

Thr Lys Leu Leu Ala Arg Arg Glu Tyr Lys Asp Thr Gly Lys Gln Phe
130 135 140

Asn Ile Leu Ala Ala Ala Trp Ile Gln Phe Met Val His Asp Trp Met
145 150 155 160

Asp His Met Glu Asp Thr Gly Gln Ile Gly Ile Thr Ala Pro Lys Glu
165 170 175

Val Ala Asn Glu Cys Pro Leu Lys Ser Phe Lys Phe His Pro Thr Lys
180 185 190

Glu Leu Pro Thr Asn Ser Asp Gly Ile Lys Ile Gly His Tyr Asn Ile
195 200 205

Arg Thr Ala Trp Trp Asp Gly Ser Ala Val Tyr Gly Asn Asn Glu Glu
210 215 220

Arg Ala Glu Lys Leu Arg Thr Tyr Val Asp Gly Lys Leu Val Ile Gly
225 230 235 240

Asp Asp Gly Leu Leu Leu His Lys Glu Asn Gly Val Ala Leu Ser Gly
245 250 255

Asp Ile Arg Asn Ser Trp Ala Gly Val Ser Ile Leu Gln Ala Leu Phe
260 265 270

Val Lys Glu His Asn Ala Val Cys Asp Ala Ile Lys Glu Glu His Pro
275 280 285

Asn Leu Ser Asp Glu Glu Leu Tyr Arg Tyr Ala Lys Leu Val Thr Ser
290 295 300

Ala Val Ile Ala Lys Val His Thr Ile Asp Trp Thr Val Glu Leu Leu
305 310 315 320

Lys Thr Lys Thr Met Arg Ala Ala Leu Arg Ala Asn Trp Tyr Gly Leu
325 330 335

Leu Gly Lys Lys Ile Lys Asp Thr Phe Gly His Ile Gly Gly Pro Ile
340 345 350

```
Leu Gly Gly Leu Val Gly Leu Lys Lys Pro Asn Asn His Gly Val Pro
        355                 360                 365

Tyr Ser Leu Thr Glu Glu Phe Thr Ser Val Tyr Arg Met His Ser Leu
    370                 375                 380

Ile Pro Ser Thr Leu Lys Leu Arg Asp Pro Thr Gly Gln Pro Asp Ala
385                 390                 395                 400

Asn Asn Ser Pro Pro Cys Leu Glu Asp Ile Asp Ile Gly Glu Met Ile
                405                 410                 415

Gly Leu Lys Gly Glu Glu Gln Leu Ser Lys Ile Gly Phe Glu Lys Gln
            420                 425                 430

Ala Leu Ser Met Gly Tyr Gln Ala Cys Gly Ala Leu Glu Leu Trp Asn
        435                 440                 445

Tyr Pro Ser Phe Phe Arg Asn Leu Ile Pro Gln Asn Leu Asp Gly Thr
    450                 455                 460

Asn Arg Ser Asp Arg Ile Asp Leu Ala Ala Leu Glu Val Tyr Arg Asp
465                 470                 475                 480

Arg Glu Arg Ser Val Pro Arg Tyr Asn Glu Phe Arg Arg Arg Leu Phe
                485                 490                 495

Leu Ile Pro Ile Lys Ser Trp Glu Asp Leu Thr Ser Asp Lys Asp Ala
            500                 505                 510

Ile Glu Thr Ile Arg Ala Ile Tyr Gly Asp Asp Val Glu Lys Leu Asp
        515                 520                 525

Leu Leu Val Gly Leu Met Ala Glu Lys Lys Ile Lys Gly Phe Ala Ile
    530                 535                 540

Ser Glu Thr Ala Phe Asn Ile Phe Ile Leu Met Ala Ser Arg Arg Leu
545                 550                 555                 560

Glu Ala Asp Arg Phe Phe Thr Ser Asn Phe Asn Glu Glu Thr Tyr Thr
                565                 570                 575

Lys Lys Gly Met Gln Trp Val Lys Thr Thr Glu Gly Leu Arg Asp Val
            580                 585                 590

Ile Asn Arg His Tyr Pro Glu Ile Thr Ala Lys Trp Met Lys Ser Ser
        595                 600                 605

Ser Ala Phe Ser Val Trp Asp Ala Asp Tyr
    610                 615


<210> SEQ ID NO 16
<211> LENGTH: 618
<212> TYPE: PRT
<213> ORGANISM: Artificial Sequence
<220> FEATURE:
<223> OTHER INFORMATION: T344N Substitution

<400> SEQUENCE: 16

Met Gly Ser Gly Leu Phe Lys Pro Arg Val His Pro Asp Leu Arg Asp
1               5                   10                  15

Val Phe Ser Lys Met Ser Phe Phe Asp Lys Ile Gly Phe Leu Phe Ile
            20                  25                  30

His Ala Phe Asp Lys Arg Asn Leu Trp His Lys Val Pro Val Pro Ile
        35                  40                  45

Gly Leu Leu Tyr Leu Asn Thr Arg Arg Thr Leu Leu Glu Lys Tyr Asn
    50                  55                  60

Leu Leu Ala Val Gly Arg Ser Ser His Gly Ala Leu Phe Asp Pro Lys
65                  70                  75                  80

Glu Phe Leu Tyr Arg Thr Glu Asp Gly Lys Tyr Asn Asp Pro His Asn
                85                  90                  95
```

-continued

```
Ala Glu Ala Gly Ser Gln Asn Thr Phe Phe Gly Arg Asn Met Glu Pro
            100                 105                 110

Val Asp Gln Gln Asp Glu Leu Met Ser Pro Asp Pro Phe Val Val Ala
        115                 120                 125

Thr Lys Leu Leu Ala Arg Arg Glu Tyr Lys Asp Thr Gly Lys Gln Phe
    130                 135                 140

Asn Ile Leu Ala Ala Ala Trp Ile Gln Phe Met Val His Asp Trp Met
145                 150                 155                 160

Asp His Met Glu Asp Thr Gly Gln Ile Gly Ile Thr Ala Pro Lys Glu
                165                 170                 175

Val Ala Asn Glu Cys Pro Leu Lys Ser Phe Lys Phe His Pro Thr Lys
            180                 185                 190

Glu Leu Pro Thr Asn Ser Asp Gly Ile Lys Ile Gly His Tyr Asn Ile
        195                 200                 205

Arg Thr Ala Trp Trp Asp Gly Ser Ala Val Tyr Gly Asn Asn Glu Glu
    210                 215                 220

Arg Ala Glu Lys Leu Arg Thr Tyr Val Asp Gly Lys Leu Val Ile Gly
225                 230                 235                 240

Asp Asp Gly Leu Leu Leu His Lys Glu Asn Gly Val Ala Leu Ser Gly
                245                 250                 255

Asp Ile Arg Asn Ser Trp Ala Gly Val Ser Ile Leu Gln Ala Leu Phe
            260                 265                 270

Val Lys Glu His Asn Ala Val Cys Asp Ala Ile Lys Glu Glu His Pro
        275                 280                 285

Asn Leu Ser Asp Glu Glu Leu Tyr Arg Tyr Ala Lys Leu Val Thr Ser
    290                 295                 300

Ala Val Ile Ala Lys Val His Thr Ile Asp Trp Thr Val Glu Leu Leu
305                 310                 315                 320

Lys Thr Lys Thr Met Arg Ala Ala Met Arg Ala Asn Trp Tyr Gly Leu
                325                 330                 335

Leu Gly Lys Lys Ile Lys Asp Asn Phe Gly His Ile Gly Gly Pro Ile
            340                 345                 350

Leu Gly Gly Leu Val Gly Leu Lys Lys Pro Asn Asn His Gly Val Pro
        355                 360                 365

Tyr Ser Leu Thr Glu Glu Phe Thr Ser Val Tyr Arg Met His Ser Leu
    370                 375                 380

Ile Pro Ser Thr Leu Lys Leu Arg Asp Pro Thr Gly Gln Pro Asp Ala
385                 390                 395                 400

Asn Asn Ser Pro Pro Cys Leu Glu Asp Ile Asp Ile Gly Glu Met Ile
                405                 410                 415

Gly Leu Lys Gly Glu Glu Gln Leu Ser Lys Ile Gly Phe Glu Lys Gln
            420                 425                 430

Ala Leu Ser Met Gly Tyr Gln Ala Cys Gly Ala Leu Glu Leu Trp Asn
        435                 440                 445

Tyr Pro Ser Phe Phe Arg Asn Leu Ile Pro Gln Asn Leu Asp Gly Thr
    450                 455                 460

Asn Arg Ser Asp Arg Ile Asp Leu Ala Ala Leu Glu Val Tyr Arg Asp
465                 470                 475                 480

Arg Glu Arg Ser Val Pro Arg Tyr Asn Glu Phe Arg Arg Arg Leu Phe
                485                 490                 495

Leu Ile Pro Ile Lys Ser Trp Glu Asp Leu Thr Ser Asp Lys Asp Ala
            500                 505                 510
```

```
Ile Glu Thr Ile Arg Ala Ile Tyr Gly Asp Asp Val Glu Lys Leu Asp
        515                 520                 525

Leu Leu Val Gly Leu Met Ala Glu Lys Lys Ile Lys Gly Phe Ala Ile
    530                 535                 540

Ser Glu Thr Ala Phe Asn Ile Phe Ile Leu Met Ala Ser Arg Arg Leu
545                 550                 555                 560

Glu Ala Asp Arg Phe Phe Thr Ser Asn Phe Asn Glu Glu Thr Tyr Thr
                565                 570                 575

Lys Lys Gly Met Gln Trp Val Lys Thr Thr Glu Gly Leu Arg Asp Val
            580                 585                 590

Ile Asn Arg His Tyr Pro Glu Ile Thr Ala Lys Trp Met Lys Ser Ser
        595                 600                 605

Ser Ala Phe Ser Val Trp Asp Ala Asp Tyr
    610                 615


<210> SEQ ID NO 17
<211> LENGTH: 618
<212> TYPE: PRT
<213> ORGANISM: Artificial Sequence
<220> FEATURE:
<223> OTHER INFORMATION: T344S Substitution

<400> SEQUENCE: 17

Met Gly Ser Gly Leu Phe Lys Pro Arg Val His Pro Asp Leu Arg Asp
1               5                   10                  15

Val Phe Ser Lys Met Ser Phe Phe Asp Lys Ile Gly Phe Leu Phe Ile
            20                  25                  30

His Ala Phe Asp Lys Arg Asn Leu Trp His Lys Val Pro Val Pro Ile
        35                  40                  45

Gly Leu Leu Tyr Leu Asn Thr Arg Arg Thr Leu Leu Glu Lys Tyr Asn
    50                  55                  60

Leu Leu Ala Val Gly Arg Ser Ser His Gly Ala Leu Phe Asp Pro Lys
65                  70                  75                  80

Glu Phe Leu Tyr Arg Thr Glu Asp Gly Lys Tyr Asn Asp Pro His Asn
                85                  90                  95

Ala Glu Ala Gly Ser Gln Asn Thr Phe Phe Gly Arg Asn Met Glu Pro
            100                 105                 110

Val Asp Gln Gln Asp Glu Leu Met Ser Pro Asp Pro Phe Val Val Ala
        115                 120                 125

Thr Lys Leu Leu Ala Arg Arg Glu Tyr Lys Asp Thr Gly Lys Gln Phe
    130                 135                 140

Asn Ile Leu Ala Ala Ala Trp Ile Gln Phe Met Val His Asp Trp Met
145                 150                 155                 160

Asp His Met Glu Asp Thr Gly Gln Ile Gly Ile Thr Ala Pro Lys Glu
                165                 170                 175

Val Ala Asn Glu Cys Pro Leu Lys Ser Phe Lys Phe His Pro Thr Lys
            180                 185                 190

Glu Leu Pro Thr Asn Ser Asp Gly Ile Lys Ile Gly His Tyr Asn Ile
        195                 200                 205

Arg Thr Ala Trp Trp Asp Gly Ser Ala Val Tyr Gly Asn Asn Glu Glu
    210                 215                 220

Arg Ala Glu Lys Leu Arg Thr Tyr Val Asp Gly Lys Leu Val Ile Gly
225                 230                 235                 240

Asp Asp Gly Leu Leu Leu His Lys Glu Asn Gly Val Ala Leu Ser Gly
                245                 250                 255
```

```
Asp Ile Arg Asn Ser Trp Ala Gly Val Ser Ile Leu Gln Ala Leu Phe
            260                 265                 270

Val Lys Glu His Asn Ala Val Cys Asp Ala Ile Lys Glu Glu His Pro
        275                 280                 285

Asn Leu Ser Asp Glu Glu Leu Tyr Arg Tyr Ala Lys Leu Val Thr Ser
    290                 295                 300

Ala Val Ile Ala Lys Val His Thr Ile Asp Trp Thr Val Glu Leu Leu
305                 310                 315                 320

Lys Thr Lys Thr Met Arg Ala Ala Met Arg Ala Asn Trp Tyr Gly Leu
                325                 330                 335

Leu Gly Lys Lys Ile Lys Asp Ser Phe Gly His Ile Gly Gly Pro Ile
            340                 345                 350

Leu Gly Gly Leu Val Gly Leu Lys Lys Pro Asn Asn His Gly Val Pro
        355                 360                 365

Tyr Ser Leu Thr Glu Glu Phe Thr Ser Val Tyr Arg Met His Ser Leu
    370                 375                 380

Ile Pro Ser Thr Leu Lys Leu Arg Asp Pro Thr Gly Gln Pro Asp Ala
385                 390                 395                 400

Asn Asn Ser Pro Pro Cys Leu Glu Asp Ile Asp Ile Gly Glu Met Ile
                405                 410                 415

Gly Leu Lys Gly Glu Glu Gln Leu Ser Lys Ile Gly Phe Glu Lys Gln
            420                 425                 430

Ala Leu Ser Met Gly Tyr Gln Ala Cys Gly Ala Leu Glu Leu Trp Asn
        435                 440                 445

Tyr Pro Ser Phe Phe Arg Asn Leu Ile Pro Gln Asn Leu Asp Gly Thr
    450                 455                 460

Asn Arg Ser Asp Arg Ile Asp Leu Ala Ala Leu Glu Val Tyr Arg Asp
465                 470                 475                 480

Arg Glu Arg Ser Val Pro Arg Tyr Asn Glu Phe Arg Arg Arg Leu Phe
                485                 490                 495

Leu Ile Pro Ile Lys Ser Trp Glu Asp Leu Thr Ser Asp Lys Asp Ala
            500                 505                 510

Ile Glu Thr Ile Arg Ala Ile Tyr Gly Asp Asp Val Glu Lys Leu Asp
        515                 520                 525

Leu Leu Val Gly Leu Met Ala Glu Lys Lys Ile Lys Gly Phe Ala Ile
    530                 535                 540

Ser Glu Thr Ala Phe Asn Ile Phe Ile Leu Met Ala Ser Arg Arg Leu
545                 550                 555                 560

Glu Ala Asp Arg Phe Phe Thr Ser Asn Phe Asn Glu Glu Thr Tyr Thr
                565                 570                 575

Lys Lys Gly Met Gln Trp Val Lys Thr Thr Glu Gly Leu Arg Asp Val
            580                 585                 590

Ile Asn Arg His Tyr Pro Glu Ile Thr Ala Lys Trp Met Lys Ser Ser
        595                 600                 605

Ser Ala Phe Ser Val Trp Asp Ala Asp Tyr
    610                 615
```

<210> SEQ ID NO 18
<211> LENGTH: 618
<212> TYPE: PRT
<213> ORGANISM: Artificial Sequence
<220> FEATURE:
<223> OTHER INFORMATION: D399G Substitution

<400> SEQUENCE: 18

-continued

```
Met Gly Ser Gly Leu Phe Lys Pro Arg Val His Pro Asp Leu Arg Asp
1               5                   10                  15

Val Phe Ser Lys Met Ser Phe Phe Asp Lys Ile Gly Phe Leu Phe Ile
            20                  25                  30

His Ala Phe Asp Lys Arg Asn Leu Trp His Lys Val Pro Val Pro Ile
        35                  40                  45

Gly Leu Leu Tyr Leu Asn Thr Arg Arg Thr Leu Leu Glu Lys Tyr Asn
    50                  55                  60

Leu Leu Ala Val Gly Arg Ser Ser His Gly Ala Leu Phe Asp Pro Lys
65                  70                  75                  80

Glu Phe Leu Tyr Arg Thr Glu Asp Gly Lys Tyr Asn Asp Pro His Asn
                85                  90                  95

Ala Glu Ala Gly Ser Gln Asn Thr Phe Phe Gly Arg Asn Met Glu Pro
            100                 105                 110

Val Asp Gln Gln Asp Glu Leu Met Ser Pro Asp Pro Phe Val Val Ala
        115                 120                 125

Thr Lys Leu Leu Ala Arg Arg Glu Tyr Lys Asp Thr Gly Lys Gln Phe
    130                 135                 140

Asn Ile Leu Ala Ala Ala Trp Ile Gln Phe Met Val His Asp Trp Met
145                 150                 155                 160

Asp His Met Glu Asp Thr Gly Gln Ile Gly Ile Thr Ala Pro Lys Glu
                165                 170                 175

Val Ala Asn Glu Cys Pro Leu Lys Ser Phe Lys Phe His Pro Thr Lys
            180                 185                 190

Glu Leu Pro Thr Asn Ser Asp Gly Ile Lys Ile Gly His Tyr Asn Ile
        195                 200                 205

Arg Thr Ala Trp Trp Asp Gly Ser Ala Val Tyr Gly Asn Asn Glu Glu
    210                 215                 220

Arg Ala Glu Lys Leu Arg Thr Tyr Val Asp Gly Lys Leu Val Ile Gly
225                 230                 235                 240

Asp Asp Gly Leu Leu Leu His Lys Glu Asn Gly Val Ala Leu Ser Gly
                245                 250                 255

Asp Ile Arg Asn Ser Trp Ala Gly Val Ser Ile Leu Gln Ala Leu Phe
            260                 265                 270

Val Lys Glu His Asn Ala Val Cys Asp Ala Ile Lys Glu Glu His Pro
        275                 280                 285

Asn Leu Ser Asp Glu Glu Leu Tyr Arg Tyr Ala Lys Leu Val Thr Ser
    290                 295                 300

Ala Val Ile Ala Lys Val His Thr Ile Asp Trp Thr Val Glu Leu Leu
305                 310                 315                 320

Lys Thr Lys Thr Met Arg Ala Ala Met Arg Ala Asn Trp Tyr Gly Leu
                325                 330                 335

Leu Gly Lys Lys Ile Lys Asp Thr Phe Gly His Ile Gly Gly Pro Ile
            340                 345                 350

Leu Gly Gly Leu Val Gly Leu Lys Lys Pro Asn Asn His Gly Val Pro
        355                 360                 365

Tyr Ser Leu Thr Glu Glu Phe Thr Ser Val Tyr Arg Met His Ser Leu
    370                 375                 380

Ile Pro Ser Thr Leu Lys Leu Arg Asp Pro Thr Gly Gln Pro Gly Ala
385                 390                 395                 400

Asn Asn Ser Pro Pro Cys Leu Glu Asp Ile Asp Ile Gly Glu Met Ile
                405                 410                 415

Gly Leu Lys Gly Glu Glu Gln Leu Ser Lys Ile Gly Phe Glu Lys Gln
```

-continued

```
            420                 425                 430

Ala Leu Ser Met Gly Tyr Gln Ala Cys Gly Ala Leu Glu Leu Trp Asn
        435                 440                 445

Tyr Pro Ser Phe Phe Arg Asn Leu Ile Pro Gln Asn Leu Asp Gly Thr
    450                 455                 460

Asn Arg Ser Asp Arg Ile Asp Leu Ala Ala Leu Glu Val Tyr Arg Asp
465                 470                 475                 480

Arg Glu Arg Ser Val Pro Arg Tyr Asn Glu Phe Arg Arg Arg Leu Phe
                485                 490                 495

Leu Ile Pro Ile Lys Ser Trp Glu Asp Leu Thr Ser Asp Lys Asp Ala
            500                 505                 510

Ile Glu Thr Ile Arg Ala Ile Tyr Gly Asp Asp Val Glu Lys Leu Asp
        515                 520                 525

Leu Leu Val Gly Leu Met Ala Glu Lys Lys Ile Lys Gly Phe Ala Ile
    530                 535                 540

Ser Glu Thr Ala Phe Asn Ile Phe Ile Leu Met Ala Ser Arg Arg Leu
545                 550                 555                 560

Glu Ala Asp Arg Phe Phe Thr Ser Asn Phe Asn Glu Glu Thr Tyr Thr
                565                 570                 575

Lys Lys Gly Met Gln Trp Val Lys Thr Thr Glu Gly Leu Arg Asp Val
            580                 585                 590

Ile Asn Arg His Tyr Pro Glu Ile Thr Ala Lys Trp Met Lys Ser Ser
        595                 600                 605

Ser Ala Phe Ser Val Trp Asp Ala Asp Tyr
    610                 615


<210> SEQ ID NO 19
<211> LENGTH: 618
<212> TYPE: PRT
<213> ORGANISM: Artificial Sequence
<220> FEATURE:
<223> OTHER INFORMATION: A400P Substitution

<400> SEQUENCE: 19

Met Gly Ser Gly Leu Phe Lys Pro Arg Val His Pro Asp Leu Arg Asp
1               5                   10                  15

Val Phe Ser Lys Met Ser Phe Phe Asp Lys Ile Gly Phe Leu Phe Ile
            20                  25                  30

His Ala Phe Asp Lys Arg Asn Leu Trp His Lys Val Pro Val Pro Ile
        35                  40                  45

Gly Leu Leu Tyr Leu Asn Thr Arg Arg Thr Leu Leu Glu Lys Tyr Asn
    50                  55                  60

Leu Leu Ala Val Gly Arg Ser Ser His Gly Ala Leu Phe Asp Pro Lys
65                  70                  75                  80

Glu Phe Leu Tyr Arg Thr Glu Asp Gly Lys Tyr Asn Asp Pro His Asn
                85                  90                  95

Ala Glu Ala Gly Ser Gln Asn Thr Phe Phe Gly Arg Asn Met Glu Pro
            100                 105                 110

Val Asp Gln Gln Asp Glu Leu Met Ser Pro Asp Pro Phe Val Val Ala
        115                 120                 125

Thr Lys Leu Leu Ala Arg Arg Glu Tyr Lys Asp Thr Gly Lys Gln Phe
    130                 135                 140

Asn Ile Leu Ala Ala Ala Trp Ile Gln Phe Met Val His Asp Trp Met
145                 150                 155                 160

Asp His Met Glu Asp Thr Gly Gln Ile Gly Ile Thr Ala Pro Lys Glu
```

```
                165                 170                 175

Val Ala Asn Glu Cys Pro Leu Lys Ser Phe Lys Phe His Pro Thr Lys
            180                 185                 190

Glu Leu Pro Thr Asn Ser Asp Gly Ile Lys Ile Gly His Tyr Asn Ile
        195                 200                 205

Arg Thr Ala Trp Trp Asp Gly Ser Ala Val Tyr Gly Asn Asn Glu Glu
    210                 215                 220

Arg Ala Glu Lys Leu Arg Thr Tyr Val Asp Gly Lys Leu Val Ile Gly
225                 230                 235                 240

Asp Asp Gly Leu Leu Leu His Lys Glu Asn Gly Val Ala Leu Ser Gly
                245                 250                 255

Asp Ile Arg Asn Ser Trp Ala Gly Val Ser Ile Leu Gln Ala Leu Phe
            260                 265                 270

Val Lys Glu His Asn Ala Val Cys Asp Ala Ile Lys Glu Glu His Pro
        275                 280                 285

Asn Leu Ser Asp Glu Glu Leu Tyr Arg Tyr Ala Lys Leu Val Thr Ser
    290                 295                 300

Ala Val Ile Ala Lys Val His Thr Ile Asp Trp Thr Val Glu Leu Leu
305                 310                 315                 320

Lys Thr Lys Thr Met Arg Ala Ala Met Arg Ala Asn Trp Tyr Gly Leu
                325                 330                 335

Leu Gly Lys Lys Ile Lys Asp Thr Phe Gly His Ile Gly Gly Pro Ile
            340                 345                 350

Leu Gly Gly Leu Val Gly Leu Lys Lys Pro Asn Asn His Gly Val Pro
        355                 360                 365

Tyr Ser Leu Thr Glu Glu Phe Thr Ser Val Tyr Arg Met His Ser Leu
    370                 375                 380

Ile Pro Ser Thr Leu Lys Leu Arg Asp Pro Thr Gly Gln Pro Asp Pro
385                 390                 395                 400

Asn Asn Ser Pro Pro Cys Leu Glu Asp Ile Asp Ile Gly Glu Met Ile
                405                 410                 415

Gly Leu Lys Gly Glu Glu Gln Leu Ser Lys Ile Gly Phe Glu Lys Gln
            420                 425                 430

Ala Leu Ser Met Gly Tyr Gln Ala Cys Gly Ala Leu Glu Leu Trp Asn
        435                 440                 445

Tyr Pro Ser Phe Phe Arg Asn Leu Ile Pro Gln Asn Leu Asp Gly Thr
    450                 455                 460

Asn Arg Ser Asp Arg Ile Asp Leu Ala Ala Leu Glu Val Tyr Arg Asp
465                 470                 475                 480

Arg Glu Arg Ser Val Pro Arg Tyr Asn Glu Phe Arg Arg Arg Leu Phe
                485                 490                 495

Leu Ile Pro Ile Lys Ser Trp Glu Asp Leu Thr Ser Asp Lys Asp Ala
            500                 505                 510

Ile Glu Thr Ile Arg Ala Ile Tyr Gly Asp Asp Val Glu Lys Leu Asp
        515                 520                 525

Leu Leu Val Gly Leu Met Ala Glu Lys Lys Ile Lys Gly Phe Ala Ile
    530                 535                 540

Ser Glu Thr Ala Phe Asn Ile Phe Ile Leu Met Ala Ser Arg Arg Leu
545                 550                 555                 560

Glu Ala Asp Arg Phe Phe Thr Ser Asn Phe Asn Glu Glu Thr Tyr Thr
                565                 570                 575

Lys Lys Gly Met Gln Trp Val Lys Thr Thr Glu Gly Leu Arg Asp Val
            580                 585                 590
```

Ile Asn Arg His Tyr Pro Glu Ile Thr Ala Lys Trp Met Lys Ser Ser
595 600 605

Ser Ala Phe Ser Val Trp Asp Ala Asp Tyr
610 615

<210> SEQ ID NO 20
<211> LENGTH: 618
<212> TYPE: PRT
<213> ORGANISM: Artificial Sequence
<220> FEATURE:
<223> OTHER INFORMATION: S508D Substitution

<400> SEQUENCE: 20

Met Gly Ser Gly Leu Phe Lys Pro Arg Val His Pro Asp Leu Arg Asp
1 5 10 15

Val Phe Ser Lys Met Ser Phe Phe Asp Lys Ile Gly Phe Leu Phe Ile
20 25 30

His Ala Phe Asp Lys Arg Asn Leu Trp His Lys Val Pro Val Pro Ile
35 40 45

Gly Leu Leu Tyr Leu Asn Thr Arg Arg Thr Leu Leu Glu Lys Tyr Asn
50 55 60

Leu Leu Ala Val Gly Arg Ser Ser His Gly Ala Leu Phe Asp Pro Lys
65 70 75 80

Glu Phe Leu Tyr Arg Thr Glu Asp Gly Lys Tyr Asn Asp Pro His Asn
85 90 95

Ala Glu Ala Gly Ser Gln Asn Thr Phe Phe Gly Arg Asn Met Glu Pro
100 105 110

Val Asp Gln Gln Asp Glu Leu Met Ser Pro Asp Pro Phe Val Val Ala
115 120 125

Thr Lys Leu Leu Ala Arg Arg Glu Tyr Lys Asp Thr Gly Lys Gln Phe
130 135 140

Asn Ile Leu Ala Ala Ala Trp Ile Gln Phe Met Val His Asp Trp Met
145 150 155 160

Asp His Met Glu Asp Thr Gly Gln Ile Gly Ile Thr Ala Pro Lys Glu
165 170 175

Val Ala Asn Glu Cys Pro Leu Lys Ser Phe Lys Phe His Pro Thr Lys
180 185 190

Glu Leu Pro Thr Asn Ser Asp Gly Ile Lys Ile Gly His Tyr Asn Ile
195 200 205

Arg Thr Ala Trp Trp Asp Gly Ser Ala Val Tyr Gly Asn Asn Glu Glu
210 215 220

Arg Ala Glu Lys Leu Arg Thr Tyr Val Asp Gly Lys Leu Val Ile Gly
225 230 235 240

Asp Asp Gly Leu Leu Leu His Lys Glu Asn Gly Val Ala Leu Ser Gly
245 250 255

Asp Ile Arg Asn Ser Trp Ala Gly Val Ser Ile Leu Gln Ala Leu Phe
260 265 270

Val Lys Glu His Asn Ala Val Cys Asp Ala Ile Lys Glu Glu His Pro
275 280 285

Asn Leu Ser Asp Glu Glu Leu Tyr Arg Tyr Ala Lys Leu Val Thr Ser
290 295 300

Ala Val Ile Ala Lys Val His Thr Ile Asp Trp Thr Val Glu Leu Leu
305 310 315 320

Lys Thr Lys Thr Met Arg Ala Ala Met Arg Ala Asn Trp Tyr Gly Leu
325 330 335

Leu Gly Lys Lys Ile Lys Asp Thr Phe Gly His Ile Gly Gly Pro Ile
340 345 350

Leu Gly Gly Leu Val Gly Leu Lys Lys Pro Asn Asn His Gly Val Pro
355 360 365

Tyr Ser Leu Thr Glu Glu Phe Thr Ser Val Tyr Arg Met His Ser Leu
370 375 380

Ile Pro Ser Thr Leu Lys Leu Arg Asp Pro Thr Gly Gln Pro Asp Ala
385 390 395 400

Asn Asn Ser Pro Pro Cys Leu Glu Asp Ile Asp Ile Gly Glu Met Ile
405 410 415

Gly Leu Lys Gly Glu Glu Gln Leu Ser Lys Ile Gly Phe Glu Lys Gln
420 425 430

Ala Leu Ser Met Gly Tyr Gln Ala Cys Gly Ala Leu Glu Leu Trp Asn
435 440 445

Tyr Pro Ser Phe Phe Arg Asn Leu Ile Pro Gln Asn Leu Asp Gly Thr
450 455 460

Asn Arg Ser Asp Arg Ile Asp Leu Ala Ala Leu Glu Val Tyr Arg Asp
465 470 475 480

Arg Glu Arg Ser Val Pro Arg Tyr Asn Glu Phe Arg Arg Arg Leu Phe
485 490 495

Leu Ile Pro Ile Lys Ser Trp Glu Asp Leu Thr Asp Asp Lys Asp Ala
500 505 510

Ile Glu Thr Ile Arg Ala Ile Tyr Gly Asp Asp Val Glu Lys Leu Asp
515 520 525

Leu Leu Val Gly Leu Met Ala Glu Lys Lys Ile Lys Gly Phe Ala Ile
530 535 540

Ser Glu Thr Ala Phe Asn Ile Phe Ile Leu Met Ala Ser Arg Arg Leu
545 550 555 560

Glu Ala Asp Arg Phe Phe Thr Ser Asn Phe Asn Glu Glu Thr Tyr Thr
565 570 575

Lys Lys Gly Met Gln Trp Val Lys Thr Thr Glu Gly Leu Arg Asp Val
580 585 590

Ile Asn Arg His Tyr Pro Glu Ile Thr Ala Lys Trp Met Lys Ser Ser
595 600 605

Ser Ala Phe Ser Val Trp Asp Ala Asp Tyr
610 615

<210> SEQ ID NO 21
<211> LENGTH: 618
<212> TYPE: PRT
<213> ORGANISM: Artificial Sequence
<220> FEATURE:
<223> OTHER INFORMATION: S72P/G74P Substitutions

<400> SEQUENCE: 21

Met Gly Ser Gly Leu Phe Lys Pro Arg Val His Pro Asp Leu Arg Asp
1 5 10 15

Val Phe Ser Lys Met Ser Phe Phe Asp Lys Ile Gly Phe Leu Phe Ile
20 25 30

His Ala Phe Asp Lys Arg Asn Leu Trp His Lys Val Pro Val Pro Ile
35 40 45

Gly Leu Leu Tyr Leu Asn Thr Arg Arg Thr Leu Leu Glu Lys Tyr Asn
50 55 60

Leu Leu Ala Val Gly Arg Ser Pro His Pro Ala Leu Phe Asp Pro Lys
65 70 75 80

-continued

```
Glu Phe Leu Tyr Arg Thr Glu Asp Gly Lys Tyr Asn Asp Pro His Asn
                85                  90                  95

Ala Glu Ala Gly Ser Gln Asn Thr Phe Phe Gly Arg Asn Met Glu Pro
            100                 105                 110

Val Asp Gln Gln Asp Glu Leu Met Ser Pro Asp Pro Phe Val Val Ala
        115                 120                 125

Thr Lys Leu Leu Ala Arg Arg Glu Tyr Lys Asp Thr Gly Lys Gln Phe
    130                 135                 140

Asn Ile Leu Ala Ala Ala Trp Ile Gln Phe Met Val His Asp Trp Met
145                 150                 155                 160

Asp His Met Glu Asp Thr Gly Gln Ile Gly Ile Thr Ala Pro Lys Glu
                165                 170                 175

Val Ala Asn Glu Cys Pro Leu Lys Ser Phe Lys Phe His Pro Thr Lys
            180                 185                 190

Glu Leu Pro Thr Asn Ser Asp Gly Ile Lys Ile Gly His Tyr Asn Ile
        195                 200                 205

Arg Thr Ala Trp Trp Asp Gly Ser Ala Val Tyr Gly Asn Asn Glu Glu
    210                 215                 220

Arg Ala Glu Lys Leu Arg Thr Tyr Val Asp Gly Lys Leu Val Ile Gly
225                 230                 235                 240

Asp Asp Gly Leu Leu Leu His Lys Glu Asn Gly Val Ala Leu Ser Gly
                245                 250                 255

Asp Ile Arg Asn Ser Trp Ala Gly Val Ser Ile Leu Gln Ala Leu Phe
            260                 265                 270

Val Lys Glu His Asn Ala Val Cys Asp Ala Ile Lys Glu Glu His Pro
        275                 280                 285

Asn Leu Ser Asp Glu Glu Leu Tyr Arg Tyr Ala Lys Leu Val Thr Ser
    290                 295                 300

Ala Val Ile Ala Lys Val His Thr Ile Asp Trp Thr Val Glu Leu Leu
305                 310                 315                 320

Lys Thr Lys Thr Met Arg Ala Ala Met Arg Ala Asn Trp Tyr Gly Leu
                325                 330                 335

Leu Gly Lys Lys Ile Lys Asp Thr Phe Gly His Ile Gly Gly Pro Ile
            340                 345                 350

Leu Gly Gly Leu Val Gly Leu Lys Lys Pro Asn Asn His Gly Val Pro
        355                 360                 365

Tyr Ser Leu Thr Glu Glu Phe Thr Ser Val Tyr Arg Met His Ser Leu
    370                 375                 380

Ile Pro Ser Thr Leu Lys Leu Arg Asp Pro Thr Gly Gln Pro Asp Ala
385                 390                 395                 400

Asn Asn Ser Pro Pro Cys Leu Glu Asp Ile Asp Ile Gly Glu Met Ile
                405                 410                 415

Gly Leu Lys Gly Glu Glu Gln Leu Ser Lys Ile Gly Phe Glu Lys Gln
            420                 425                 430

Ala Leu Ser Met Gly Tyr Gln Ala Cys Gly Ala Leu Glu Leu Trp Asn
        435                 440                 445

Tyr Pro Ser Phe Phe Arg Asn Leu Ile Pro Gln Asn Leu Asp Gly Thr
    450                 455                 460

Asn Arg Ser Asp Arg Ile Asp Leu Ala Ala Leu Glu Val Tyr Arg Asp
465                 470                 475                 480

Arg Glu Arg Ser Val Pro Arg Tyr Asn Glu Phe Arg Arg Arg Leu Phe
                485                 490                 495
```

```
Leu Ile Pro Ile Lys Ser Trp Glu Asp Leu Thr Ser Asp Lys Asp Ala
            500                 505                 510

Ile Glu Thr Ile Arg Ala Ile Tyr Gly Asp Asp Val Glu Lys Leu Asp
        515                 520                 525

Leu Leu Val Gly Leu Met Ala Glu Lys Lys Ile Lys Gly Phe Ala Ile
    530                 535                 540

Ser Glu Thr Ala Phe Asn Ile Phe Ile Leu Met Ala Ser Arg Arg Leu
545                 550                 555                 560

Glu Ala Asp Arg Phe Phe Thr Ser Asn Phe Asn Glu Glu Thr Tyr Thr
                565                 570                 575

Lys Lys Gly Met Gln Trp Val Lys Thr Thr Glu Gly Leu Arg Asp Val
            580                 585                 590

Ile Asn Arg His Tyr Pro Glu Ile Thr Ala Lys Trp Met Lys Ser Ser
        595                 600                 605

Ser Ala Phe Ser Val Trp Asp Ala Asp Tyr
    610                 615


<210> SEQ ID NO 22
<211> LENGTH: 618
<212> TYPE: PRT
<213> ORGANISM: Artificial Sequence
<220> FEATURE:
<223> OTHER INFORMATION: V156I/M160T Substitutions

<400> SEQUENCE: 22

Met Gly Ser Gly Leu Phe Lys Pro Arg Val His Pro Asp Leu Arg Asp
1               5                   10                  15

Val Phe Ser Lys Met Ser Phe Phe Asp Lys Ile Gly Phe Leu Phe Ile
            20                  25                  30

His Ala Phe Asp Lys Arg Asn Leu Trp His Lys Val Pro Val Pro Ile
        35                  40                  45

Gly Leu Leu Tyr Leu Asn Thr Arg Arg Thr Leu Leu Glu Lys Tyr Asn
    50                  55                  60

Leu Leu Ala Val Gly Arg Ser Ser His Gly Ala Leu Phe Asp Pro Lys
65                  70                  75                  80

Glu Phe Leu Tyr Arg Thr Glu Asp Gly Lys Tyr Asn Asp Pro His Asn
                85                  90                  95

Ala Glu Ala Gly Ser Gln Asn Thr Phe Phe Gly Arg Asn Met Glu Pro
            100                 105                 110

Val Asp Gln Gln Asp Glu Leu Met Ser Pro Asp Pro Phe Val Val Ala
        115                 120                 125

Thr Lys Leu Leu Ala Arg Arg Glu Tyr Lys Asp Thr Gly Lys Gln Phe
    130                 135                 140

Asn Ile Leu Ala Ala Ala Trp Ile Gln Phe Met Ile His Asp Trp Thr
145                 150                 155                 160

Asp His Met Glu Asp Thr Gly Gln Ile Gly Ile Thr Ala Pro Lys Glu
                165                 170                 175

Val Ala Asn Glu Cys Pro Leu Lys Ser Phe Lys Phe His Pro Thr Lys
            180                 185                 190

Glu Leu Pro Thr Asn Ser Asp Gly Ile Lys Ile Gly His Tyr Asn Ile
        195                 200                 205

Arg Thr Ala Trp Trp Asp Gly Ser Ala Val Tyr Gly Asn Asn Glu Glu
    210                 215                 220

Arg Ala Glu Lys Leu Arg Thr Tyr Val Asp Gly Lys Leu Val Ile Gly
225                 230                 235                 240
```

-continued

```
Asp Asp Gly Leu Leu Leu His Lys Glu Asn Gly Val Ala Leu Ser Gly
                245                 250                 255

Asp Ile Arg Asn Ser Trp Ala Gly Val Ser Ile Leu Gln Ala Leu Phe
            260                 265                 270

Val Lys Glu His Asn Ala Val Cys Asp Ala Ile Lys Glu Glu His Pro
        275                 280                 285

Asn Leu Ser Asp Glu Glu Leu Tyr Arg Tyr Ala Lys Leu Val Thr Ser
    290                 295                 300

Ala Val Ile Ala Lys Val His Thr Ile Asp Trp Thr Val Glu Leu Leu
305                 310                 315                 320

Lys Thr Lys Thr Met Arg Ala Ala Met Arg Ala Asn Trp Tyr Gly Leu
                325                 330                 335

Leu Gly Lys Lys Ile Lys Asp Thr Phe Gly His Ile Gly Gly Pro Ile
            340                 345                 350

Leu Gly Gly Leu Val Gly Leu Lys Lys Pro Asn Asn His Gly Val Pro
        355                 360                 365

Tyr Ser Leu Thr Glu Glu Phe Thr Ser Val Tyr Arg Met His Ser Leu
    370                 375                 380

Ile Pro Ser Thr Leu Lys Leu Arg Asp Pro Thr Gly Gln Pro Asp Ala
385                 390                 395                 400

Asn Asn Ser Pro Pro Cys Leu Glu Asp Ile Asp Ile Gly Glu Met Ile
                405                 410                 415

Gly Leu Lys Gly Glu Glu Gln Leu Ser Lys Ile Gly Phe Glu Lys Gln
            420                 425                 430

Ala Leu Ser Met Gly Tyr Gln Ala Cys Gly Ala Leu Glu Leu Trp Asn
        435                 440                 445

Tyr Pro Ser Phe Phe Arg Asn Leu Ile Pro Gln Asn Leu Asp Gly Thr
    450                 455                 460

Asn Arg Ser Asp Arg Ile Asp Leu Ala Ala Leu Glu Val Tyr Arg Asp
465                 470                 475                 480

Arg Glu Arg Ser Val Pro Arg Tyr Asn Glu Phe Arg Arg Arg Leu Phe
                485                 490                 495

Leu Ile Pro Ile Lys Ser Trp Glu Asp Leu Thr Ser Asp Lys Asp Ala
            500                 505                 510

Ile Glu Thr Ile Arg Ala Ile Tyr Gly Asp Asp Val Glu Lys Leu Asp
        515                 520                 525

Leu Leu Val Gly Leu Met Ala Glu Lys Lys Ile Lys Gly Phe Ala Ile
    530                 535                 540

Ser Glu Thr Ala Phe Asn Ile Phe Ile Leu Met Ala Ser Arg Arg Leu
545                 550                 555                 560

Glu Ala Asp Arg Phe Phe Thr Ser Asn Phe Asn Glu Glu Thr Tyr Thr
                565                 570                 575

Lys Lys Gly Met Gln Trp Val Lys Thr Thr Glu Gly Leu Arg Asp Val
            580                 585                 590

Ile Asn Arg His Tyr Pro Glu Ile Thr Ala Lys Trp Met Lys Ser Ser
        595                 600                 605

Ser Ala Phe Ser Val Trp Asp Ala Asp Tyr
    610                 615
```

<210> SEQ ID NO 23
<211> LENGTH: 618
<212> TYPE: PRT
<213> ORGANISM: Artificial Sequence
<220> FEATURE:
<223> OTHER INFORMATION: G74P/D399G/A400P Substitutions

<400> SEQUENCE: 23

Met Gly Ser Gly Leu Phe Lys Pro Arg Val His Pro Asp Leu Arg Asp
1               5                   10                  15

Val Phe Ser Lys Met Ser Phe Phe Asp Lys Ile Gly Phe Leu Phe Ile
            20                  25                  30

His Ala Phe Asp Lys Arg Asn Leu Trp His Lys Val Pro Val Pro Ile
        35                  40                  45

Gly Leu Leu Tyr Leu Asn Thr Arg Arg Thr Leu Leu Glu Lys Tyr Asn
    50                  55                  60

Leu Leu Ala Val Gly Arg Ser Ser His Pro Ala Leu Phe Asp Pro Lys
65                  70                  75                  80

Glu Phe Leu Tyr Arg Thr Glu Asp Gly Lys Tyr Asn Asp Pro His Asn
                85                  90                  95

Ala Glu Ala Gly Ser Gln Asn Thr Phe Phe Gly Arg Asn Met Glu Pro
            100                 105                 110

Val Asp Gln Gln Asp Glu Leu Met Ser Pro Asp Pro Phe Val Val Ala
        115                 120                 125

Thr Lys Leu Leu Ala Arg Arg Glu Tyr Lys Asp Thr Gly Lys Gln Phe
    130                 135                 140

Asn Ile Leu Ala Ala Ala Trp Ile Gln Phe Met Val His Asp Trp Met
145                 150                 155                 160

Asp His Met Glu Asp Thr Gly Gln Ile Gly Ile Thr Ala Pro Lys Glu
                165                 170                 175

Val Ala Asn Glu Cys Pro Leu Lys Ser Phe Lys Phe His Pro Thr Lys
            180                 185                 190

Glu Leu Pro Thr Asn Ser Asp Gly Ile Lys Ile Gly His Tyr Asn Ile
        195                 200                 205

Arg Thr Ala Trp Trp Asp Gly Ser Ala Val Tyr Gly Asn Asn Glu Glu
    210                 215                 220

Arg Ala Glu Lys Leu Arg Thr Tyr Val Asp Gly Lys Leu Val Ile Gly
225                 230                 235                 240

Asp Asp Gly Leu Leu Leu His Lys Glu Asn Gly Val Ala Leu Ser Gly
                245                 250                 255

Asp Ile Arg Asn Ser Trp Ala Gly Val Ser Ile Leu Gln Ala Leu Phe
            260                 265                 270

Val Lys Glu His Asn Ala Val Cys Asp Ala Ile Lys Glu Glu His Pro
        275                 280                 285

Asn Leu Ser Asp Glu Glu Leu Tyr Arg Tyr Ala Lys Leu Val Thr Ser
    290                 295                 300

Ala Val Ile Ala Lys Val His Thr Ile Asp Trp Thr Val Glu Leu Leu
305                 310                 315                 320

Lys Thr Lys Thr Met Arg Ala Ala Met Arg Ala Asn Trp Tyr Gly Leu
                325                 330                 335

Leu Gly Lys Lys Ile Lys Asp Thr Phe Gly His Ile Gly Gly Pro Ile
            340                 345                 350

Leu Gly Gly Leu Val Gly Leu Lys Lys Pro Asn Asn His Gly Val Pro
        355                 360                 365

Tyr Ser Leu Thr Glu Glu Phe Thr Ser Val Tyr Arg Met His Ser Leu
    370                 375                 380

Ile Pro Ser Thr Leu Lys Leu Arg Asp Pro Thr Gly Gln Pro Gly Pro
385                 390                 395                 400

Asn Asn Ser Pro Pro Cys Leu Glu Asp Ile Asp Ile Gly Glu Met Ile

-continued

```
                405                 410                 415

Gly Leu Lys Gly Glu Glu Gln Leu Ser Lys Ile Gly Phe Glu Lys Gln
            420                 425                 430

Ala Leu Ser Met Gly Tyr Gln Ala Cys Gly Ala Leu Glu Leu Trp Asn
        435                 440                 445

Tyr Pro Ser Phe Phe Arg Asn Leu Ile Pro Gln Asn Leu Asp Gly Thr
    450                 455                 460

Asn Arg Ser Asp Arg Ile Asp Leu Ala Ala Leu Glu Val Tyr Arg Asp
465                 470                 475                 480

Arg Glu Arg Ser Val Pro Arg Tyr Asn Glu Phe Arg Arg Arg Leu Phe
                485                 490                 495

Leu Ile Pro Ile Lys Ser Trp Glu Asp Leu Thr Ser Asp Lys Asp Ala
            500                 505                 510

Ile Glu Thr Ile Arg Ala Ile Tyr Gly Asp Asp Val Glu Lys Leu Asp
        515                 520                 525

Leu Leu Val Gly Leu Met Ala Glu Lys Lys Ile Lys Gly Phe Ala Ile
    530                 535                 540

Ser Glu Thr Ala Phe Asn Ile Phe Ile Leu Met Ala Ser Arg Arg Leu
545                 550                 555                 560

Glu Ala Asp Arg Phe Phe Thr Ser Asn Phe Asn Glu Glu Thr Tyr Thr
                565                 570                 575

Lys Lys Gly Met Gln Trp Val Lys Thr Thr Glu Gly Leu Arg Asp Val
            580                 585                 590

Ile Asn Arg His Tyr Pro Glu Ile Thr Ala Lys Trp Met Lys Ser Ser
        595                 600                 605

Ser Ala Phe Ser Val Trp Asp Ala Asp Tyr
    610                 615


<210> SEQ ID NO 24
<211> LENGTH: 7
<212> TYPE: PRT
<213> ORGANISM: Artificial Sequence
<220> FEATURE:
<223> OTHER INFORMATION: His-tag

<400> SEQUENCE: 24

Met His His His His His His
1               5
```